(12) United States Patent
Platt et al.

(10) Patent No.: US 8,332,160 B1
(45) Date of Patent: Dec. 11, 2012

(54) SYSTEMS AND METHODS FOR ENGINEERING NUCLEIC ACID CONSTRUCTS USING SCORING TECHNIQUES

(75) Inventors: Darren M. Platt, Emeryville, CA (US); Michael W. Bissell, Emeryville, CA (US); Sunil S. Chandran, Emeryville, CA (US); Brian L. Hawthorne, Emeryville, CA (US); Erik Jedediah Dean, Emeryville, CA (US); Christopher Dolan, Emeryville, CA (US)

(73) Assignee: Amyris Biotechnologies, Inc., Emeryville, CA (US)

( * ) Notice: Subject to any disclaimer, the term of this patent is extended or adjusted under 35 U.S.C. 154(b) by 0 days.

(21) Appl. No.: 13/442,625

(22) Filed: Apr. 9, 2012

Related U.S. Application Data

(60) Provisional application No. 61/561,241, filed on Nov. 17, 2011.

(51) Int. Cl.
*G06F 19/00* (2011.01)
*G06F 15/00* (2006.01)
*G11C 17/00* (2006.01)
*G01N 33/48* (2006.01)

(52) U.S. Cl. .................. 702/20; 365/94; 700/1; 702/27

(58) Field of Classification Search .................. None
See application file for complete search history.

(56) References Cited

U.S. PATENT DOCUMENTS

| | | | |
|---|---|---|---|
| 6,143,527 | A | 11/2000 | Pachuk et al. |
| 7,172,886 | B2 | 2/2007 | Keasling et al. |
| 7,192,751 | B2 | 3/2007 | Keasling et al. |
| 7,659,097 | B2 | 2/2010 | Renninger et al. |
| 8,110,360 | B2 | 2/2012 | Serber et al. |
| 2003/0022179 | A1 | 1/2003 | Chestnut et al. |
| 2011/0054654 | A1 | 3/2011 | Phillips et al. |

FOREIGN PATENT DOCUMENTS

| | | |
|---|---|---|
| GB | 2 393 441 A | 3/2004 |
| WO | WO 2007038276 A2 | 4/2007 |
| WO | WO 2008045380 A2 | 3/2008 |
| WO | WO 2008095927 A1 | 8/2008 |
| WO | WO 2010059763 A1 | 5/2010 |

OTHER PUBLICATIONS

Sleight et al. In-Fusion BioBrick assembly and re-engineering Nucleic Acids Research vol. 38, pp. 2624-2636 (2010).*

Database Geneseq, EBI Accession No. GSN: AQY14130, Database Accession No. AQY14130 (Mar. 20, 2008).
Database EMBL: "Sequence 100 from Patent WO 2006077411", EBI Accession No. CS364005, Database Accession No. CS364005 (Aug. 11, 2006).
Database EMBL: "DNA sequence of yeast glyceraldehyde-3-phosphate dehydrage nase promoter-16-25bp." EBI Accession No. E01366, Database Accession No. E01366 (Oct. 7, 1997).
Database EMBL: Sequence 3 from patent US 5,436,136, EBI Accession No. EMBL: AR364858, Database Accession No. AR364858 (Sep. 4, 2003).
Database EMBL: "Sequence 79 from Patent WO 2007050671", EMI Accession No. CS619922, Data base Accession No. CS619922 (Jul. 2, 2007).
Database EBML: "Sequence 239 from Patent WO 2002064766" EBI Accession No. EMBL: AX536638, Database Accession No. AX536638 (Nov. 22, 2002).
Database EMBL: "*Saccharomyces cerevisiae* mRNA, clone Y052_L08_F.abl, 5'-end sequence", EBI accession No. EMBL: DB659207, Database Accession No. DB659207, (Dec. 8, 2006).
Densmore et al., "Algorithms for automated DNA assembly," *Nucleic Acids Res.* 38(8):2607-16 (2010).
Holt, "Synthetic Genomes brought closer to life", *Nature Biotechnology*, 26(3):296-297(Mar. 2008).
Horton, et al., "Engineering hybrid genes without the use of restriction enzymes: gene splicing by overlap extension" *Gene* 77(1):61-68 (Apr. 15, 1989).
Pachuk et al., "Chain reaction cloning: a one-step method for directional ligation of multiple DNA fragments," *Gene* 243:19-25 (2000).
Pedersen et al., "Towards programming languages for genetic engineering of living cells", *J. R. Soc. Interface* 6, S437-S450 (2009).

* cited by examiner

*Primary Examiner* — John S Brusca
(74) *Attorney, Agent, or Firm* — Morgan, Lewis & Bockius LLP

(57) ABSTRACT

Systems and methods are provided for defining a nucleic acid construct for integration at locus L of an organism. Nucleic acid requests are received, each such request specifying a genetic change to L. The request are expanded into component polynucleotides which are then arranged into $\{AR_1, \ldots, AR_m\}$ different arrangements, each $AR_i$ in $\{AR_1, \ldots, AR_m\}$ defining a different arrangement of the component polynucleotides. A score $S_i$ for each $AR_i$ in $\{AR_1, \ldots, AR_m\}$ is determined based on whether source constructs encoding a portion of $AR_i$ are physically present. An $AR_f$ in $\{AR_1, \ldots, AR_m\}$ is selected based on the score for $AR_f$. Primer pairs are calculated to amplify the portions of $AR_f$ not represented in the source constructs. The portions of $AR_f$ amplified by the primer pairs and the portions of $AR_f$ in the source constructs, ordered by $AR_f$, define the nucleic acid construct.

30 Claims, 21 Drawing Sheets

Component polynucleotides for the exemplary plurality of nucleic acid requests: HO^::pFBA>ADH2::pSLN1>ADH1

5' – $LA_1$ – pFBA1 – $LB_1$ – 3'

5' – $LA_2$ – ADH2 – $LB_2$ – 3'

5' – $LA_3$ – pSLN1 – $LB_3$ – 3'

5' – $LA_4$ – ADH1 – $LB_4$ – 3'

Fig. 4A

5' – $LA_1$ – pFBA1 – $LB_1$ – ADH2 – $LB_2$ – pSLN1 – $LB_3$ – ADH1 – $LB_4$ – 3'

5' – $LA_1$ – pFBA1 – $LB_1$ – ADH2 – $LB_2$ – pSLN1 – $LB_3$ – 3'

5' – $LA_2$ – ADH2 – $LB_2$ – pSLN1 – $LB_3$ – ADH1 – $LB_4$ – 3'

5' – $LA_1$ – pFBA1 – $LB_1$ – ADH2 – $LB_2$ – 3'

5' – $LA_3$ – pSLN1 – $LB_3$ – ADH1 – $LB_4$ – 3'

5' – $LA_2$ – ADH2 – $LB_2$ – pSLN1 – $LB_3$ – 3'

Fig. 4B

| | |
|---|---|
| Library of linker nucleic acid sequences | 64 |
|   Category 1 | 702-1 |
|     5' linkers (LA) | 702-1-A |
|     LA Annealable linker nucleic acid sequence ($LA_1$) | 704-1-$LA_1$ |
|     ⋮ | |
|     LA Annealable linker nucleic acid sequence n ($LA_n$) | 704-1-$LA_n$ |
|     3' linkers (LB) | 702-1-B |
|     LB Annealable linker nucleic acid sequence 1 ($LB_1$) | 704-1-$LB_1$ |
|     ⋮ | |
|     LB Annealable linker nucleic acid sequence n ($LB_n$) | 704-1-$LB_n$ |
|   Category 2 | 702-2 |
|     5' linkers (LA) | 702-2-A |
|     LA Annealable linker nucleic acid sequence 1 ($LA_1$) | 704-2-$LA_1$ |
|     ⋮ | |
|     LA Annealable linker nucleic acid sequence m ($LA_m$) | 704-2-$LA_m$ |
|     3' linkers (LB) | 702-2-B |
|     LB Annealable linker nucleic acid sequence 1 ($LB_1$) | 704-2-$LB_1$ |
|     ⋮ | |
|     LB Annealable linker nucleic acid sequence m ($LB_m$) | 704-2-$LB_m$ |
|   ⋮ | |
|   Category Q | 702-Q |
|     5' linkers (LA) | 702-Q-A |
|     LA Annealable linker nucleic acid sequence 1 ($LA_1$) | 704-Q-$LA_1$ |
|     ⋮ | |
|     LB Annealable linker nucleic acid sequence k ($LA_k$) | 704-Q-$LA_k$ |
|     3' linkers (LB) | 702-Q-B |
|     LB Annealable linker nucleic acid sequence 1 ($LB_1$) | 704-Q-$LB_1$ |
|     ⋮ | |
|     LB Annealable linker nucleic acid sequence k ($LB_k$) | 704-Q-$ZB_k$ |

Fig. 7

| | ID ▼ | Name | Linker | Direction | Breed | Source | Insert | Status | Concentration | Votes |
|---|---|---|---|---|---|---|---|---|---|---|
| 602-1 | 699 | 01-0-D-699 | 01 | 0 | 0 | S. cerevisiae s | mjgvbk | requested | | 👍x1👎x0 👍👎 |
| | 698 | 49-1-Gst-698 | 49 | 1 | Gst | S. cerevisiae s | ERG12 | available | | 👍x1👎x1 👍👎 |
| | 697 | 01-0-U-697 | 01 | 0 | U | S. cerevisiae s | IME1 | requested | | 👍x0👎x1 👍👎 |
| | 696 | 49-0-D-696 | 49 | 0 | D | S. cerevisiae s | IME1 | available | | 👍x0👎x0 👍👎 |
| | 695 | 29-0-D-695 | 29 | 0 | D | S. cerevisiae s | IME1 | | | 👍x1👎x0 👍👎 |
| | 694 | 34-0-Gs-694 | 34 | 0 | Gs | L.reuteni | Phosphoketolase | requested | | 👍x2👎x0 👍👎 |
| | 693 | 01-0-U-693 | 01 | 0 | U | S. cerevisiae s | 5' TAL1 | available | | 👍x1👎x0 👍👎 |
| | 692 | 01-0-U-693 | 01 | 0 | U | S. cerevisiae s | 5' MATa | available | | 👍x0👎x0 👍👎 |
| | 691 | 23-0-G-691 | 23 | 0 | U | S. cerevisiae s | Mata | requested | | 👍x0👎x0 👍👎 |
| | 690 | 49-1-Gs-690 | 49 | 1 | Gs | S. cerevisiae s | HMG1 | requested | | 👍x0👎x0 👍👎 |
| | 689 | 01-0-U-689 | 01 | 0 | U | S. cerevisiae s | 5' AC52 | available | 55.00 | 👍x0👎x0 👍👎 |
| | 688 | 39-0-D-699 | 39 | 0 | D | S. cerevisiae s | 3' AC52 | available | 80.00 | 👍x0👎x0 👍👎 |
| | 687 | 39-0-D-687 | 39 | 0 | D | S. cerevisiae s | 3' AC51 | available | 78.00 | 👍x0👎x0 👍👎 |
| | 686 | 34-0-Gs-686 | 34 | 0 | Gs | E. coli | ACS | available | 246.00 | 👍x0👎x0 👍👎 |
| | 685 | 34-0-s-685 | 34 | 0 | s | E. coli | adHE | available | 437.00 | 👍x0👎x0 👍👎 |
| | 684 | 29-0-D-684 | 29 | 0 | D | S. cerevisiae s | 3' 5TE12 | available | 99.00 | 👍x0👎x0 👍👎 |
| | 683 | 34-0-Gs-683 | 34 | 0 | Gs | Pseudomonas | nahO | available | 44.00 | 👍x0👎x0 👍👎 |
| | 682 | 34-0-082 | 34 | 0 | G | B.subtillis | PTA | | | 👍x0👎x0 👍👎 |
| | 680 | 12-0-M-680 | 12 | 0 | M | S. cerevisiae s | HI53 | available | 80.00 | 👍x0👎x0 👍👎 |
| 602-Z | 679 | 01-0-U-679 | 01 | 0 | U | S. cerevisiae s | 5' STE12 | available | 150.00 | 👍x0👎x0 👍👎 |

Fig. 21

SYSTEMS AND METHODS FOR ENGINEERING NUCLEIC ACID CONSTRUCTS USING SCORING TECHNIQUES

This application claims benefit under 35 U.S.C. §119(e) of U.S. Provisional Application No. 61/561,241, filed on Nov. 17, 2011, which is incorporated herein by reference in its entirety for all purposes.

1. FIELD

The present disclosure relates generally to the field of recombinant DNA technology and, more particularly, to improved systems, compositions, and methods for the ordered assembly of component polynucleotides into engineered nucleic acid constructs in a rapid and cost efficient manner using available resources.

2. BACKGROUND

A prominent goal of synthetic biology is to produce novel biological systems that carry out specified desired functions such as the incorporation of biosynthetic pathways into host cells. As such, synthetic biology requires tools for the selection of genetic components that are inserted or removed from host cells, as well as tools for selective mutation of genetic components within host cells.

One application of synthetic biology is the development of novel isoprenoid synthesis pathways in yeast in order to manufacture isoprenoids at reduced costs relative to conventional techniques. Conventional techniques for manufacturing many isoprenoids, a diverse family of over 40,000 individual compounds, requires their extraction from natural sources such as plants, microbes, and animals. The elucidation of the mevalonate-dependent (MEV) and deoxyxylulose-5-phosphate (DXP) metabolic pathways has made biosynthetic production of some isoprenoids feasible. For instance, microbes have been engineered to overexpress a part of or the entire MEV metabolic pathway for production of an isoprenoid named amorpha-4, II-diene. See U.S. Pat. Nos. 7,172,886 and 7,192,751, which are hereby incorporated by reference.

U.S. Pat. No. 7,659,097 discloses how the activity of the MEV and DXP pathways can be altered in a number of ways in order to increase the synthesis of various isoprenoids. Such alterations include, but are not limited to, expressing a modified form of any respective enzyme in the MEV or DXP pathways so that they exhibit increased solubility in the host cell, expression of an altered form of the respective enzyme that lacks a domain through which the activity of the enzyme is inhibited, expressing a modified form of the respective enzyme that has a higher Kcat or a lower Km for its substrate, or expressing an altered form of the respective enzyme that is not affected by feed-back or feed-forward regulation by another molecule in the pathway. Moreover, the nucleic acid sequences encoding the enzymes in such synthetic pathways can be modified to reflect the codon preference of the host cell in order to effect a higher expression of such enzymes in the host cell. Further still, multiple copies of enzymes in such biosynthetic pathways may be introduced into host cells to effect a higher expression of such enzymes. Further still, such enzymes may be placed under the control of powerful promoters in the host cell to effect a higher expression of such enzymes. See U.S. Pat. No. 7,569,097, which is hereby incorporated by reference. The above illustrates just some of the many changes to the locus of a host cell or organism that are made in order to realize a synthetic biology design goal such as the manufacture of isoprenoids.

As the above illustrates, the realization of synthetic biology goals is best achieved through an iterative trial and error approach in which tens, hundreds, or even thousands of different design attempts are tested in vivo in a host cell or organism on a periodic basic (e.g., daily, weekly, monthly) to determine if a design goal has been reached and to improve upon such design goals. As such, it is clear that what is needed in the art are improved platforms for realizing such design goals faster, more efficiently, and in an even more economical fashion.

One facet of a platform for realizing synthetic biology design goals is mechanisms for reducing design goals into a form that is interpretable by a compiler. In one approach, Pedersen and Phillips, 2009, "Towards programming languages for genetic engineering of living cells", J. R. Soc. Interface 6, S437-S450 provide a formal language for genetic engineering of living cells (GEC) in which one or more in silico databases of parts are searched by a compiler for a set of parts that satisfy a design goal. See also, U.S. Patent Application Publication No. 2011/0054654 in which GEC is also described. The work of Pedersen and coworkers provides a satisfactory framework for modeling complex pathways in silico. Such in silico models can then be used to make in silico predictions on what changes to the model would achieve a desired design goal. However, the data that would make such in silico modeling more useful, such as the molecular properties of a number of components of molecular pathways under a number of different reaction conditions, is presently unavailable. Consequently, to date, the work of Pederson and coworkers has not eliminated the need for an iterative trial and error approach to realizing a synthetic biology design goal in which tens, hundreds, or even thousands of different design attempts are tested in vivo on a periodic basic (e.g., daily, weekly, monthly).

The drawbacks of iterative trial and error approaches are the time and costs that such approaches take. It takes extensive resources, including time and money, to make all the constructs necessary for a design attempt and to test the design attempt in vivo. For each design attempt, the constructs, termed engineered nucleic acid constructs, which effect the desired changes to the locus of a host cell or organism, need to be made. This often requires the custom synthesis of oligonucleotide primers in order to subclone desired nucleic acid components from a genomic library and/or to effect desired mutations in existing nucleic acid sequences. Such engineered nucleic acid constructs are then introduced into a host cell or organism where they either recombine with a locus of the host genome or exist in a stable vector form. As such, the design of even a limited number of engineered nucleic acid constructs may require the synthesis of dozens or even hundreds of custom oligonucleotide primers in order to make the needed engineered nucleic acid constructs using existing template nucleic acids, such as existing constructs or nucleic acids in a genomic library.

Thus, despite advances in the field of synthetic biology, there remains a need for improved systems, compositions, and methods that provide for the rapid and ordered assembly of nucleic acid components into engineered nucleic acid constructs. Particularly needed are systems and methods that reduce the cost and increase the speed of the iterative trial and error approach that is used in synthetic biology applications, including the construction of engineered nucleic acid constructs. These and other needs are met by systems, compositions, and methods of the present disclosure.

3. SUMMARY

The present disclosure addresses the shortcomings of known approaches to synthetic biology. In the present disclosure, a robust language is provided for describing nucleic acid requests. These nucleic acid requests are interpreted and expanded into a plurality of component nucleic acids in a contiguous arrangement. A database of physically present component polynucleic acids is searched to see if any of the component nucleic acids in the contiguous arrangement already exist. In some embodiments, and where possible, the order of individual component polynucleic acids in the plurality of component polynucleic acids is rearranged, often several times, to see if such contiguous rearrangements lead to the identification of a larger number of component polynucleic acids in the database of physically present component polynucleic acids. A contiguous arrangement of the plurality of component nucleic acids that is best represented by the database of physically present component polynucleic acids is selected. Primer pairs are generated for the portions of the selected contiguous arrangement not present in the database. The portions of the contiguous arrangement amplified by the one or more primer pairs and the one or more component polynucleotides in the database identified for the selected contiguous arrangement collectively define the engineered nucleic acid construct. These components can be used to rapidly assemble the engineered nucleic acid construct in a faster, more efficient manner than conventional iterative trial and error approaches to pursuing a synthetic biology design goal.

One aspect provides a method of defining an engineered nucleic acid construct for integration into a genomic locus L of a target organism or a host cell. A plurality of nucleic acid requests $\{NR_1, \ldots, NR_n\}$ is received from a requester through a computer interface. Here, n is a positive integer greater than 1. In some embodiments, n is an integer in the range 1 to 100. Each nucleic acid request $NR_i$ in $\{NR_1, \ldots, NR_n\}$ specifies a genetic change to L, for example, a request to insert an exogenous promoter-gene unit at L. Each nucleic request $NR_i$ in the plurality of $\{NR_1, \ldots, NR_n\}$ is expanded into a corresponding component polynucleotide, thereby forming a plurality of component polynucleotides. The type of expansion that is performed in this step depends on the nature of each $NR_i$. In some embodiments, $NR_i$ includes the full nucleic acid sequence of what is to be inserted at L. In such embodiments, since the nucleic acid sequence is fully described, the expansion step does not accomplish any actual expansion of the nucleic acid request. In some embodiments $NR_i$ is a request for a point mutation of a given gene. To ease the work on the request, advantageously, $NR_i$ may use abbreviated notation to identify the gene and the point mutation that is requested. Such abbreviated notation is described more fully below. In this instance, the expansion step validates that the name of the gene identified in $NR_i$ is a valid gene, retrieves the nucleic acid sequence for the gene, and makes the requested point mutation.

Once the expansion step is complete, the plurality of $\{NR_1, \ldots, NR_n\}$ is represented as a plurality of component polynucleotides. The plurality of component polynucleotides is arranged into a contiguous arrangement $AR_i$ using linker nucleic acid sequences from a predetermined library of linker nucleic acid sequences to form the arrangement $AR_i$. This arranging is done a number of times, either in concurrent or sequential arrangement steps, until a set of $\{AR_1, \ldots, AR_m\}$ contiguous arrangements is formed. This is done because, typically, several different arrangements of the component polynucleotides, each of which fully comply with the requirements of $\{NR_1, \ldots, NR_n\}$ exists. Thus, m is a positive integer greater than 1, and, in fact, often much larger than 1. For example, m can be 5 or greater in some embodiments. A score $S_i$ is determined for each respective contiguous arrangement $AR_i$ in $\{AR_1, \ldots, AR_m\}$. In some embodiments, the scoring step is done after each arrangement $AR_i$ is made rather than waiting until the set of $\{AR_1, \ldots, AR_m\}$ has been defined. In such embodiments, the cycle of arranging and scoring is terminated as soon as a satisfactory arrangement is found.

For each respective contiguous arrangement $AR_i$, a contribution to the score $S_i$ for the contiguous arrangement is made when one or more source constructs are identified as being physically present in a freezer store. Each such physically present source construct encodes one or more of the component polynucleotides. Moreover, in some embodiments, a 3' or 5' terminus, or both the 3' and 5' termini, of each respective component polynucleotide of the one or more component polynucleotides encoded by the one or more physically present source constructs is bound to a corresponding linker nucleic acid sequence that was used for the corresponding component polynucleotide in the arranging to form $AR_i$. To illustrate, consider the case where there is a component polynucleotide CP with a 3' linker nucleic acid sequence $LB_2$ (i.e., 5'-CP-$LB_2$-3') in $AR_i$. What is desired is a component polynucleotide CP encoded by the one or more physically present source constructs with a 3' linker nucleic acid sequence $LB_2$ (i.e., 5'-CP-$LB_2$-3').

A final contiguous arrangement $AR_f$ in $\{AR_1, \ldots, AR_m\}$ is selected that has a score $S_i$ that meets a selection criterion. In response to selection of the $AR_f$, one or more primer pairs is calculated based on the $AR_f$, where each primer pair in the one or more primer pairs is capable of amplifying a portion of $AR_f$ not represented in the one or more physically present source constructs identified for $AR_f$. The portions of the contiguous arrangement amplified by the one or more primer pairs and the one or more component polynucleotides in the one or more physically present source constructs identified for $AR_f$, in the order specified in the $AR_f$, collectively define the engineered nucleic acid construct. At least portions of the above-identified method (e.g., the expanding, arranging, repeating, determining, selecting, or calculating described above) is performed using one or more suitably programmed computers.

Another aspect provides an apparatus comprising one or more memories and one or more processors. The one or more memories and the one or more processors are in electronic communication with each other. The one or more memories tangibly encode a set of instructions for defining an engineered nucleic acid construct for integration into a genomic locus L of a target organism or a host cell using the one or more processors. The set of instructions comprise instructions for receiving a plurality of nucleic acid requests $\{NR1, \ldots, NR_n\}$, where n is a positive integer greater than 1, each nucleic acid request $NR_i$ in $\{NR_1, \ldots, NR_n\}$ specifying a genetic change to L. The set of instructions further comprise instructions for expanding each $NR_i$ in $\{NR_1, \ldots, NR_n\}$ into a corresponding component polynucleotide, thereby forming a plurality of component polynucleotides. The set of instructions further comprise instructions for arranging the plurality of component polynucleotides into a contiguous arrangement $AR_i$, where the arranging uses linker nucleic acid sequences from a predetermined library of linker nucleic acid sequences to combine component polynucleotides in the plurality of component polynucleotides into a contiguous arrangement $AR_i$. The set of instructions further comprise instructions for repeating the instructions for arranging until a set of $\{AR_1, \ldots, AR_m\}$ contiguous arrangements are formed, where m is a positive integer greater than 1. The set of $\{AR_1, \ldots, AR_m\}$ contiguous arrangements represent a plurality of different contiguous arrangements of the component polynucleotides in the plurality of component polynucleotides. The set of instructions further comprise instructions for determining a score $S_i$ for each respective contiguous arrangement $AR_i$ in $\{AR_1, \ldots, AR_m\}$. For each respective contiguous arrangement $AR_i$, a contribution to the score $S_i$ is made when one or more source constructs are identified as being physically present in a freezer store, where each of the one or more physically present source constructs encode one or more of the component polynucleotides, and where a 3' or 5' terminus, or both the 3' and 5' termini, of each respective component polynucleotide in the one or more component polynucleotides encoded by the one or more physically present source constructs is bound to a corresponding linker that was used for the corresponding component polynucleotide in the instructions for arranging to form $AR_i$. The set of instructions further comprise instructions for selecting a final contiguous arrangement $AR_f$ in $\{AR_1, \ldots, AR_m\}$ having a score $S_i$ that meets a selection criterion as an optimal contiguous arrangement. The set of instructions further comprise instructions for calculating one or more primer pairs based upon the final contiguous arrangement $AR_f$, where each primer pair in the one or more primer pairs is capable of amplifying a portion of $AR_f$ not represented in the one or more component polynucleotides in the one or more physically present source constructs identified for the $AR_f$. The portions of the contiguous arrangement amplified by the one or more primer pairs and the one or more component polynucleotides in the one or more physically present source constructs identified for $AR_f$, in the order specified in $AR_f$, collectively define the engineered nucleic acid construct.

Another aspect provides a method of defining an engineered nucleic acid construct for integration into a genomic locus L of a target organism or a host cell. The method comprises receiving a plurality of nucleic acid requests $\{NR_1, \ldots, NR_n\}$, where n is a positive integer greater than 1. Each nucleic acid request $NR_i$ in $\{NR_1, \ldots, NR_n\}$ specifies a genetic change to L. Each $NR_i$ in $\{NR_1, \ldots, NR_n\}$ is expanded into a corresponding component polynucleotide, thereby forming a plurality of component polynucleotides. The plurality of component polynucleotides is arranged into a contiguous arrangement $AR_i$. This arranging uses linker nucleic acid sequences from a predetermined library of linker nucleic acid sequences to combine component polynucleotides in the plurality of component polynucleotides into the $AR_i$. In response to the arranging, one or more source constructs from a plurality of source constructs physically present in a freezer store are selected. Each of the one or more physically present source constructs encodes one or more of the component polynucleotides. A 3' or 5' terminus, or both a 3' and 5' termini, of each respective component polynucleotide in the one or more component polynucleotides encoded by the one or more physically present source constructs is bound to a corresponding linker that was used for the corresponding component polynucleotide in the arranging to form $AR_i$. One or more primer pairs are calculated based upon $AR_i$. Each primer pair is capable of amplifying a portion of $AR_i$ not represented in the one or more physically present source constructs identified for $AR_i$. The portions of the contiguous arrangement $AR_i$ amplified by the one or more primer pairs and the one or more component polynucleotides in the one or more physically present source constructs identified for $AR_i$, in the order specified by $AR_i$, collectively define the engineered nucleic acid construct. At least portions of the above-identified method (e.g., the expanding, arranging, selecting, and/or calculating) is performed using one or more suitably programmed computers.

Another aspect of the present disclosure provides an apparatus comprising one or more memories and one or more processors. The one or more memories and the one or more processors are in electronic communication with each other. The one or more memories tangibly encode a set of instructions for defining an engineered nucleic acid construct for integration into a genomic locus L of a target organism or a host cell using the one or more processors. In this aspect of the present disclosure, the set of instructions comprise instructions for receiving a plurality of nucleic acid requests $\{NR_1, \ldots, NR_n\}$, where n is a positive integer greater than 1. Each nucleic acid request $NR_i$ in $\{NR_1, \ldots, NR_n\}$ specifies a genetic change to L. The set of instructions further comprise instructions for expanding each $NR_i$ in $\{NR_1, \ldots, NR_n\}$ into a corresponding component polynucleotide having a nucleic acid sequence, thereby forming a plurality of component polynucleotides. The set of instructions further comprise instructions for arranging the plurality of component polynucleotides into a contiguous arrangement $AR_i$. The arranging uses linker nucleic acid sequences from a predetermined library of linker nucleic acid sequences to combine component polynucleotides in the plurality of component polynucleotides into a contiguous arrangement $AR_i$. The set of instructions further comprise instructions for selecting one or more source constructs from a plurality of source constructs physically present in a freezer store. Each of the one or more physically present source constructs encodes one or more of the component polynucleotides. A 3' or 5' terminus, or both the 3' and 5' termini, of each respective component polynucleotide in the one or more component polynucleotides encoded by the one or more physically present source constructs is bound to a corresponding linker nucleic acid that was used for the respective component polynucleotide in the arranging to form $AR_i$. The set of instructions further comprise instructions for calculating one or more primer pairs based upon the $AR_i$. Each primer pair in the one or more primer pairs is capable of amplifying a portion of the $AR_i$ not represented in the one or more physically present source constructs identified for the $AR_i$, where the portions of the $AR_i$ amplified by the one or more primer pairs and the one or more component polynucleotides in the one or more physically present source constructs identified for the $AR_i$, in the order specified by the $AR_i$, collectively define the engineered nucleic acid construct.

Another aspect of the present disclosure provides a method of defining a plurality of engineered nucleic acid constructs $\{EN_1, \ldots, EN_k\}$, where k is a positive integer greater than 1. Each engineered nucleic acid construct $EN_i$ in $\{EN_1, \ldots, EN_k\}$ is designed to be integrated into a genomic locus L of a target organism or a host cell. The method comprises receiving, for each respective $EN_i$ in $\{EN_1, \ldots, EN_k\}$, a corresponding plurality of $\{NR_{i,1}, \ldots, NR_{i,n}\}$ nucleic acid requests. Each nucleic acid request $NR_{i,j}$ in $\{NR_{i,1}, \ldots, NR_{i,n}\}$ specifies a genetic change to L. For each respective $EN_i$ in $\{EN_1, \ldots, EN_k\}$, n is a positive integer that is the same or different as n for each other $EN_m$ in $\{EN_1, \ldots, EN_k\}$. In the method, for each respective $EN_i$ in $\{EN_1, \ldots, EN_k\}$, each $NR_{i,j}$ in $\{NR_{i,1}, \ldots, NR_{i,n}\}$ is expanded into a corresponding component polynucleotide having a nucleic acid sequence, thereby forming a corresponding plurality of component polynucleotides. For each respective $EN_i$ in $\{EN_1, \ldots, EN_k\}$, the corresponding plurality of component polynucleotides from the expanding is arranged into a contiguous arrangement $AR_i$. This arranging uses linker nucleic acid sequences from a predetermined library of linker nucleic acid sequences to combine component polynucleotides in the corresponding plurality of component polynucleotides into $AR_i$, thereby forming a plurality of contiguous arrangements $\{AR_1, \ldots, AR_m\}$, each $AR_i$ in $\{AR_1, \ldots, AR_m\}$ representing an $EN_i$ in $\{EN_1, \ldots, EN_k\}$. For each respective $EN_i$ in $\{EN_1, \ldots, EN_k\}$, one or more source constructs from a plurality of source constructs physically present in a freezer store is selected. Each of the one or more physically present source constructs for a respective $EN_i$ in $\{EN_1, \ldots, EN_k\}$ encodes one or more of the component polynucleotides in the plurality of component polynucleotides for the respective $EN_i$. Moreover, a 3' or 5' terminus, or both the 3' and 5' termini, of each respective component polynucleotide in the one or more component polynucleotides encoded by the one or more physically present source constructs for a respective $EN_i$ is bound to a corresponding linker nucleic acid that was used for the respective component polynucleotide in the arranging step above that was used to form $AR_i$. For each respective $EN_i$ in $\{EN_1, \ldots, EN_k\}$, one or more primer pairs based upon the $AR_i$ in $\{AR_1, \ldots, AR_m\}$ that represents $EN_i$ is calculated. Each primer pair in the one or more primer pairs for a $AR_i$ is capable of amplifying a portion of $AR_i$ not represented in the one or more physically present source constructs identified for $AR_i$. The portions of the contiguous arrangement $AR_i$ amplified by the one or more primer pairs and the one or more component polynucleotides in the one or more physically present source constructs identified for $AR_i$, in the order specified by $AR_i$, collectively define the engineered nucleic acid construct $EN_i$. In some embodiments, at least one of the aforementioned steps (e.g., the expanding, arranging, selecting, and/or calculating) is performed using one or more suitably programmed computers.

Another aspect provides an apparatus comprising one or more memories and one or more processors. The one or more memories and the one or more processors are in electronic communication with each other. The one or more memories encode a set of instructions for defining a plurality of $\{EN_1, \ldots, EN_k\}$ engineered nucleic acid constructs, where k is a positive integer greater than 1, using the one or more processors. Each engineered nucleic acid construct $EN_i$ in $\{EN_1, \ldots, EN_k\}$ is for integration into a genomic locus L of a target organism or a host cell. The set of instructions comprises instructions for receiving, for each respective $EN_i$ in $\{EN_1, \ldots, EN_k\}$, a corresponding plurality of $\{NR_{i,1}, \ldots, NR_{i,n}\}$ nucleic acid requests. Each nucleic acid request $NR_{i,j}$ in $\{NR_{i,1}, \ldots, NR_{i,n}\}$ specifies a genetic change to L. For each respective $EN_i$ in $\{EN_1, \ldots, EN_k\}$, n is a positive integer that is the same or different as n for each other $EN_m$ in $\{EN_1, \ldots, EN_k\}$. The set of instructions further comprise instructions for expanding, for each respective $EN_i$ in $\{EN_1, \ldots, EN_k\}$, each $NR_{i,j}$ in $\{NR_{i,1}, \ldots, NR_{i,n}\}$ into a corresponding component polynucleotide having a nucleic acid sequence, thereby forming a corresponding plurality of component polynucleotides for each respective $EN_i$ in $\{EN_1, \ldots, EN_k\}$. The set of instructions further comprises instructions for arranging, for each respective $EN_i$ in $\{EN_1, \ldots, EN_k\}$, the corresponding plurality of component polynucleotides from the expanding into a contiguous arrangement $AR_i$, where the arranging uses linker nucleic acid sequences from a predetermined library of linker nucleic acid sequences to combine component polynucleotides in the corresponding plurality of component polynucleotides into $AR_i$, thereby forming a plurality of contiguous arrangements $\{AR_1, \ldots, AR_m\}$, each $AR_i$ in $\{AR_1, \ldots, AR_m\}$ representing a $EN_i$ in $\{EN_1, \ldots, EN_k\}$. The set of instructions further comprises instructions for selecting, for each respective $EN_i$ in $\{EN_1, \ldots, EN_k\}$, one or more source constructs from a plurality of source constructs physically present in a freezer store, where each of the one or more physically present source constructs for a respective $EN_i$ in $\{EN_1, \ldots, EN_k\}$ encode one or more of the component polynucleotides in the plurality of component polynucleotides for the respective $EN_i$, and where a 3' or 5' terminus, or both the 3' and 5' termini, of each respective component polynucleotide in the one or more component polynucleotides encoded by the one or more physically present source constructs for a respective $EN_i$ is bound to a corresponding linker nucleic acid that was used for the respective component polynucleotide in the arranging to form $AR_i$. The set of instructions further comprise instructions for calculating, for each respective $EN_i$ in $\{EN_1, \ldots, EN_k\}$, one or more primer pairs based upon the $AR_i$ in $\{AR_1, \ldots, AR_m\}$ that represents $EN_i$, where each primer pair in the one or more primer pairs is capable of amplifying a portion of $AR_i$ not represented in the one or more physically present source constructs identified for $AR_i$, and where the portions of $AR_i$ amplified by the one or more primer pairs and the one or more component polynucleotides in the one or more physically present source constructs identified for $AR_i$, in the order specified by $AR_i$, collectively define the engineered nucleic acid construct $EN_i$.

Another aspect of the present disclosure provides an apparatus comprising one or more memories and one or more processors. The one or more memories and the one or more processors are in electronic communication with each other. The one or more memories encode a set of instructions for defining a plurality of engineered nucleic acid constructs $\{EN_1, \ldots, EN_k\}$, where k is an integer greater than 1. Each engineered nucleic acid construct $EN_i$ in $\{EN_1, \ldots, EN_k\}$ is for integration into a genomic locus L of a target organism or a host cell. The set of instructions comprise instructions for receiving, for each respective $EN_i$ in $\{EN_1, \ldots, EN_k\}$, a corresponding plurality of nucleic acid requests $\{NR_{i,1}, \ldots, NR_{i,n}\}$ in digital alphanumeric format. Each nucleic acid request $NR_{i,j}$ in $\{NR_{i,1}, \ldots, NR_{i,n}\}$ specifies a genetic change to L, where, for each respective $EN_i$ in $\{EN_1, \ldots, EN_k\}$, n is a positive integer that is the same or different as n for each other $EN_m$ in $\{EN_1, \ldots, EN_k\}$. The set of instructions further comprise instructions for expanding, for each respective $EN_i$ in $\{EN_1, \ldots, EN_k\}$, each $NR_{i,j}$ in $\{NR_{i,1}, \ldots, NR_{i,n}\}$ into a corresponding component polynucleotide having a nucleic acid sequence, thereby forming a corresponding plurality of component polynucleotides for each respective $EN_i$ in $\{EN_1, \ldots, EN_k\}$. The set of instructions further comprise instructions for arranging, for each respective $EN_i$ in $\{EN_1, \ldots, EN_k\}$, the corresponding plurality of component polynucleotides from the instructions for expanding into a contiguous arrangement $AR_i$, where the arranging uses linker nucleic acid sequences from a predetermined library of linker nucleic acid sequences to combine component polynucleotides in the plurality of corresponding component polynucleotides into $AR_i$, thereby forming a plurality of contiguous arrangements $\{AR_1, \ldots, AR_m\}$, each $AR_i$ in $\{AR_1, \ldots, AR_m\}$ representing an $EN_i$ in $\{EN_1, \ldots, EN_k\}$. The set of instructions further comprise instructions for selecting, for each respective $EN_i$ in $\{EN_1, \ldots, EN_k\}$, one or more source constructs from a plurality of source constructs physically present in a freezer store, where each of the one or more physically present source constructs for a respective $EN_i$ in $\{EN_1, \ldots, EN_k\}$ encodes one or more of the component polynucleotides in the plurality of component polynucleotides for the respective $EN_i$, and where a 3' or 5' terminus, or both the 3' and 5' termini, of each respective component polynucleotide in the one or more component polynucleotides encoded by the one or more physically present source constructs for a respective $EN_i$ is bound to a corresponding linker nucleic acid that was used for the respective component polynucleotide in the arranging to form $AR_i$. The set of instructions further includes instructions for calculating, for each respective $EN_i$ in $\{EN_1, \ldots, EN_k\}$, one or more primer pairs based upon the $AR_i$ in $\{AR_1, \ldots, AR_m\}$ that represents $EN_i$, where each primer pair in the one or more primer pairs for an $AR_i$ is capable of amplifying a portion of $AR_i$ not represented in the one or more source constructs identified for $AR_i$, where the portions of $AR_i$ amplified by the one or more primer pairs and the one or more component polynucleotides in the one or more physically present source constructs identified for $AR_i$, in the order specified by $AR_i$, collectively define the engineered nucleic acid construct $EN_i$.

Another aspect of the present disclosure provides a method for defining a plurality of $\{EN_1, \ldots, EN_k\}$ engineered nucleic acid constructs, where k is an integer greater than 1, each engineered nucleic acid construct $EN_i$ in $\{EN_1, \ldots, EN_k\}$ for integration into a genomic locus L of a target organism or a host cell. The method comprises receiving, for each respective $EN_i$ in $\{EN_1, \ldots, EN_k\}$, a corresponding plurality of $\{NR_{i,1}, \ldots, NR_{i,n}\}$ nucleic acid requests in digital alphanumeric format, each nucleic acid request $NR_{i,j}$ in $\{NR_{i,1}, \ldots, NR_{i,n}\}$ specifying a genetic change to L, where, for each respective $EN_i$ in $\{EN_1, \ldots, EN_k\}$, n is a positive integer that is the same or different as n for each other $EN_m$ in $\{EN_1, \ldots, EN_k\}$. The method further comprises expanding, for each respective $EN_i$ in $\{EN_1, \ldots, EN_k\}$, each $NR_{i,j}$ in $\{NR_{i,1}, \ldots, NR_{i,n}\}$ into a corresponding component polynucleotide having a nucleic acid sequence, thereby forming a corresponding plurality of component polynucleotides for each respective $EN_i$ in $\{EN_1, \ldots, EN_k\}$. The method further comprises arranging, for each respective $EN_i$ in $\{EN_1, \ldots, EN_k\}$, the corresponding plurality of component polynucleotides from the expanding into a contiguous arrangement $AR_i$, where the arranging uses linker nucleic acid sequences from a predetermined library of linker nucleic acid sequences to combine component polynucleotides in the plurality of corresponding component polynucleotides into $AR_i$, thereby forming a plurality of contiguous arrangements $\{AR_1, \ldots, AR_k\}$, each $AR_i$ in $\{AR_1, \ldots, AR_k\}$ representing an $EN_i$ in $\{EN_1, \ldots, EN_k\}$. The method further comprises selecting, for each respective $EN_i$ in $\{EN_1, \ldots, EN_k\}$, one or more source constructs from a plurality of source constructs physically present in a freezer store, where the one or more physically present source constructs collectively encode a portion of the $AR_i$ corresponding to $EN_i$. The method further comprises calculating, for each respective $EN_i$ in $\{EN_1, \ldots, EN_k\}$, one or more primer pairs based upon the $AR_i$ in $\{AR_1, \ldots, AR_k\}$ that represents the respective $EN_i$, where each primer pair in the one or more primer pairs is capable of amplifying a portion of $AR_i$ not represented in the one or more physically present source constructs identified for $AR_i$, and where the portions of $AR_i$ amplified by the one or more primer pairs and the one or more component polynucleotides in the one or more physically present source constructs identified for $AR_i$, in the order specified by $AR_i$, collectively define the engineered nucleic acid construct $EN_i$. The method further comprises outputting to a non-transitory computer memory, a persistent data storage, a monitor, or a printer, for each respective $EN_i$ in $\{EN_1, \ldots, EN_k\}$, one or more primer pairs based upon the $AR_i$ in $\{AR_1, \ldots, AR_k\}$ that represents the respective $EN_i$, and the one or more source constructs identified by the instructions for calculating for the respective $EN_i$, where at least a portion of the above-identified method (e.g., the expanding, arranging, selecting, and/or calculating) is performed using a suitably programmed computer.

Another aspect of the present disclosure provides an apparatus comprising one or more memories and one or more processors. The one or more memories and the one or more processors are in electronic communication with each other. The one or more memories encode a set of instructions for defining an engineered nucleic acid construct for integration into a genomic locus L of a target organism or a host cell using the one or more processors. The set of instructions comprise instructions for representing a set of component polynucleotide slots in either (i) a linear or a near linear contiguous arrangement on a display or (ii) a vertical or a near vertical arrangement on the display, where each component polynucleotide slot in the set of component polynucleotide slots is configured to represent a component polynucleotide when populated. The set of component polynucleotide slots collectively define the engineered nucleic acid construct. Moreover, at least a portion of the set of component polynucleotide slots is initially unpopulated. The set of instructions further comprise instructions for receiving a selection of a first component polynucleotide slot in the set of component polynucleotide slots. The set of instructions further comprise instructions for listing, as a table on the display and responsive to receiving the selection of the first component polynucleotide slot, a first plurality of component polynucleotides physically present in a freezer store that are eligible to populate the first component polynucleotide slot. The set of instructions further comprise instructions for permitting a user to populate the first component polynucleotide slot with a component polynucleotide from the table. The set of instructions further comprise instructions for receiving a selection of a second component polynucleotide slot in the set of component polynucleotide slots. The set of instructions further comprise instructions for dynamically updating the table on the display, responsive to receiving the selection of the second component polynucleotide slot, to list a second plurality of component polynucleotides physically present in the freezer store that are eligible to populate the second component polynucleotide slot. The set of instructions further comprise instructions for permitting a user to populate the second component polynucleotide slot with a component polynucleotide from the table where the component polynucleotides used to populate the set of component polynucleotide slots, in the sequential order displayed in the display, define the engineered nucleic acid construct.

Another aspect provides an apparatus comprising one or more memories and one or more processors, where the one or more memories and the one or more processors are in electronic communication with each other, the one or more memories encoding a set of instructions for determining whether a nucleic acid sequence is present in any source construct in a plurality of source constructs physically present in a freezer store, using the one or more processors. The set of instructions comprises instructions for receiving a first nucleic acid sequence in electronic alphanumeric format using a display in electronic communication with the one or more memories. The set of instructions further comprises instructions for receiving a matching threshold criterion using the display. The set of instructions further comprises instructions for comparing the first nucleic acid sequence with a sequence of each respective source construct in the plurality of source constructs, where, when a second nucleic acid sequence that satisfies the matching threshold criterion is found within the sequence of a respective source construct, the instructions for comparing further include instructions for displaying an identity of the respective source construct.

4. BRIEF DESCRIPTION OF THE FIGURES

FIG. 1 shows an exemplary computer system for defining an engineered nucleic acid construct for integration into a genomic locus in accordance with an embodiment of the present disclosure.

FIG. 2 illustrates an exemplary method for defining an engineered nucleic acid construct for integration into a genomic locus, in which individual arrangements of component polynucleotides in a plurality of different arrangements of component polynucleotides, each such individual arrangement encoding a candidate for the engineered nucleic acid construct, are scored based on availability of their component polynucleotides in a freezer store, in accordance with an embodiment of the present disclosure.

FIG. 3 illustrates a graphical user interface for inputting one or more pluralities of nucleic acid requests, where each of the one or more pluralities of nucleic acid requests specifies a set of genetic changes that are to made to a locus, in accordance with an embodiment of the present disclosure.

FIG. 4 provides an exemplary plurality of nucleic acid requests, HOˆ::pFBA1>ADH2::pSLN1>ADH1, in accordance with an embodiment of the present disclosure. FIG. 4A illustrates a complete set of possible component polynucleotides that may be searched in a freezer store database for an exemplary arrangement of the plurality of nucleic acid requests: 5'-$LA_1$-pFBA1-$LB_1$-3',5'-$LA_2$-ADH2-$LB_2$-3',5'-$LA_3$-pSLN1-$LB_3$-3',5'-$LA_4$-ADH1-$LB_4$-3', which encodes the plurality of nucleic acid requests HOˆ::pFBA1>ADH2::pSLN1>ADH1, in accordance with an embodiment of the present disclosure. FIG. 4B illustrates a complete set of possible subsets of an exemplary arrangement in a single source construct.

FIG. 5 illustrates the portions of a final arrangement of component polynucleotides for an engineered nucleic acid construct that are encoded by matching component polynucleotides in a freezer store database and the portions of the final arrangement that are to be built using primer pairs and a nucleic acid library of a target organism or a host cell in accordance with an embodiment of the present disclosure.

FIG. 7 illustrates a library of linker nucleic acid sequences including the category of each linker nucleic acid sequence in accordance with an embodiment of the present disclosure.

FIG. 8 illustrates another exemplary freezer store database detailing source constructs that are physically present in a corresponding freezer store and, for each such source construct, the component polynucleotide (inserts) within the source construct and other information in accordance with an embodiment of the present disclosure.

Figure 9:
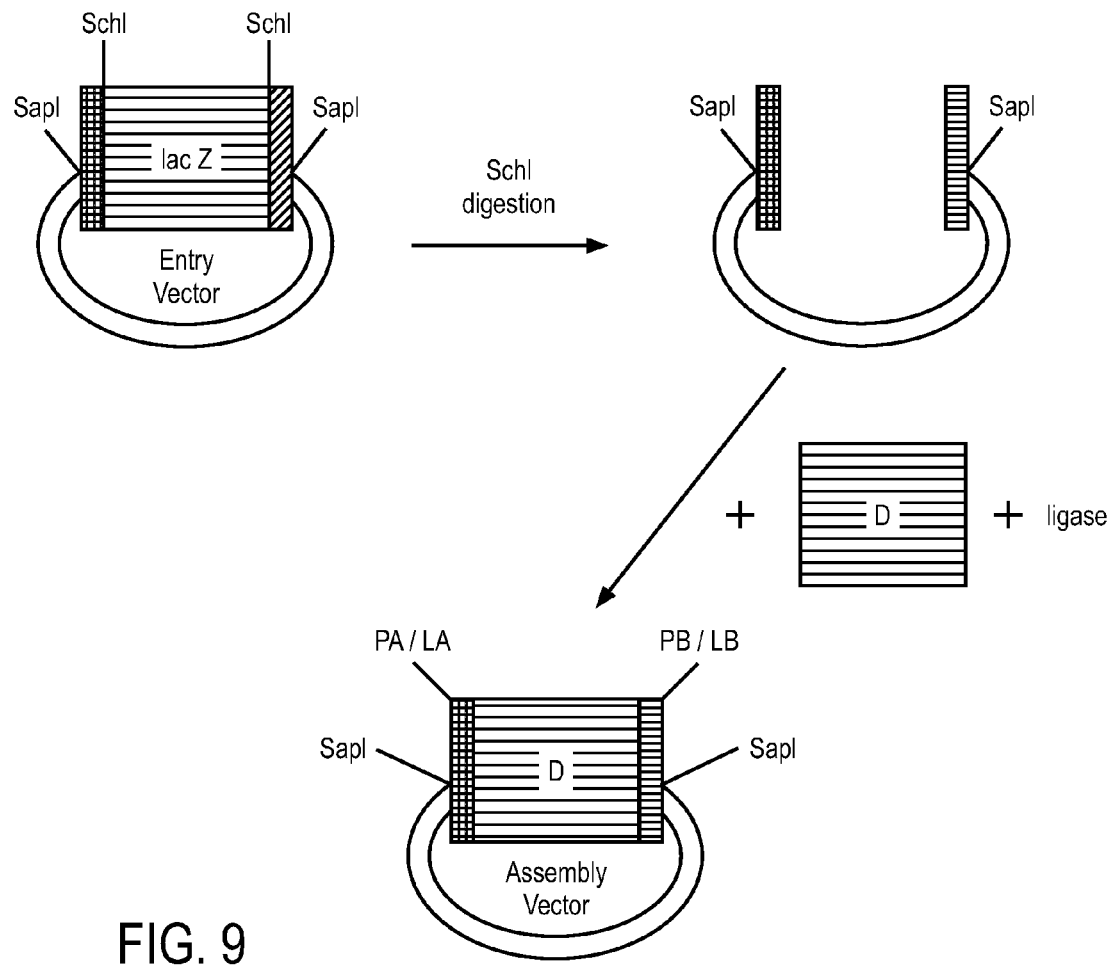

FIG. 9 provides an exemplary method of preparing an entry vector for acceptance of a DNA segment to form an assembly vector. In the exemplary method, RY=RZ=SchI. Digestion with SchI, a Type IIS restriction endonuclease that is capable of producing blunt ends, allows for isolation of the vector with the linker sites open to be fused to the DNA segment (D). Blunt-end ligation of D into the entry vector can be performed by traditional methods using, e.g., T4 DNA ligase.

Figure 10:
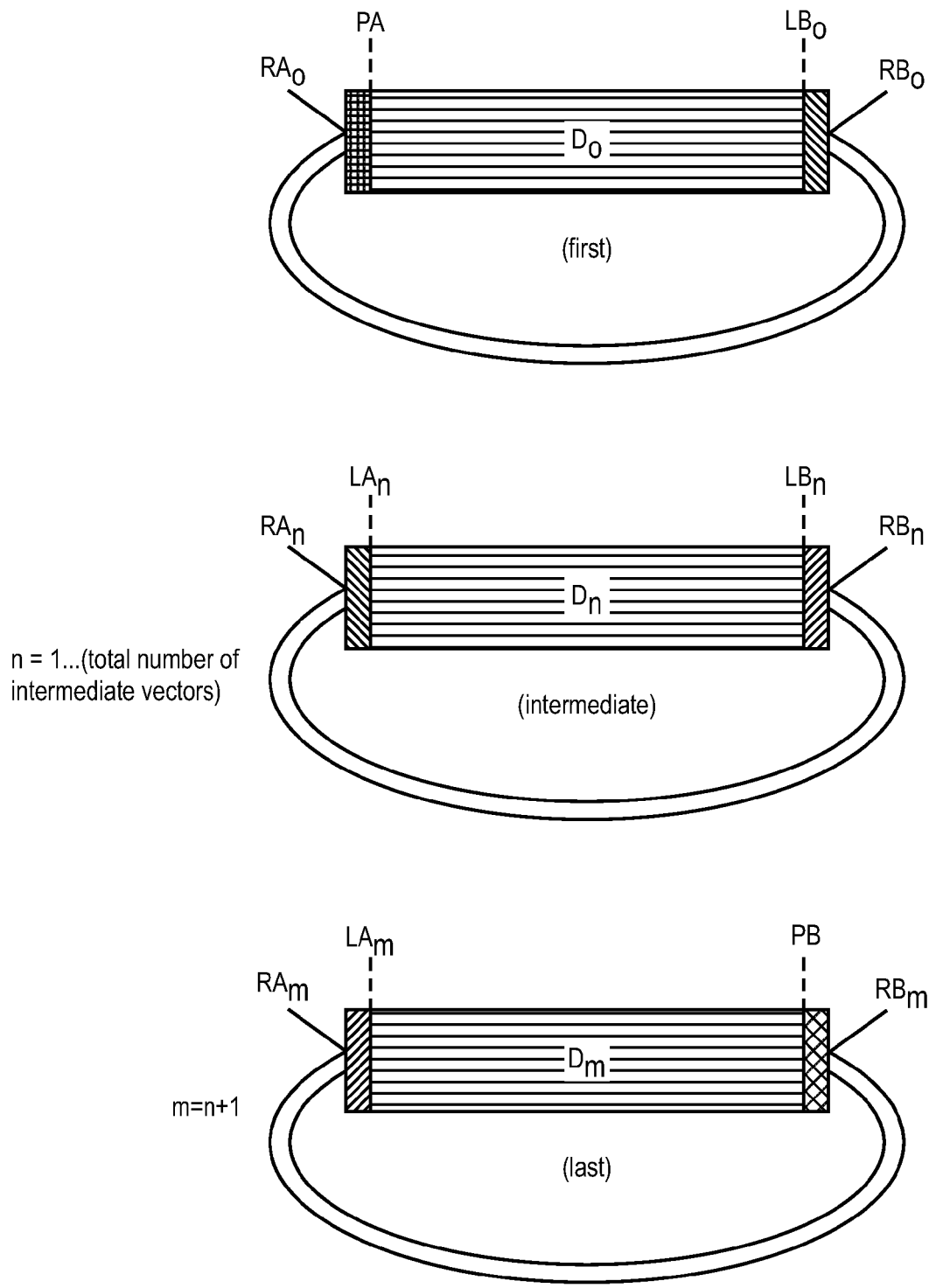

FIG. 10 presents a schematic of an assembly composition comprising a plurality of assembly vectors (first, intermediate, and last), each comprising a DNA segment of interest ($D_0$, $D_n$, $D_m$). The first nucleic acid molecule comprises a first restriction site $RA_0$, a primer binding segment PA, a DNA segment $D_0$, an annealable linker sequence $LB_0$, and a second restriction site $RB_0$. The one or more intermediate nucleic acid molecules comprise a first restriction site $RA_n$, a first annealable linker sequence $LA_n$, a DNA segment $D_n$, a second annealable linker sequence $LB_n$, and a second restriction site $RB_n$ wherein n represents an integer from one to the number of intermediate nucleic acid molecules; and the last nucleic acid molecule comprises a first restriction site $RA_m$, an annealable linker sequence $LA_m$, a DNA segment $D_m$, a primer binding segment PB, a second restriction site $RB_m$ wherein m represents an integer one greater than the number of intermediate nucleic acid molecules.

Figure 11:
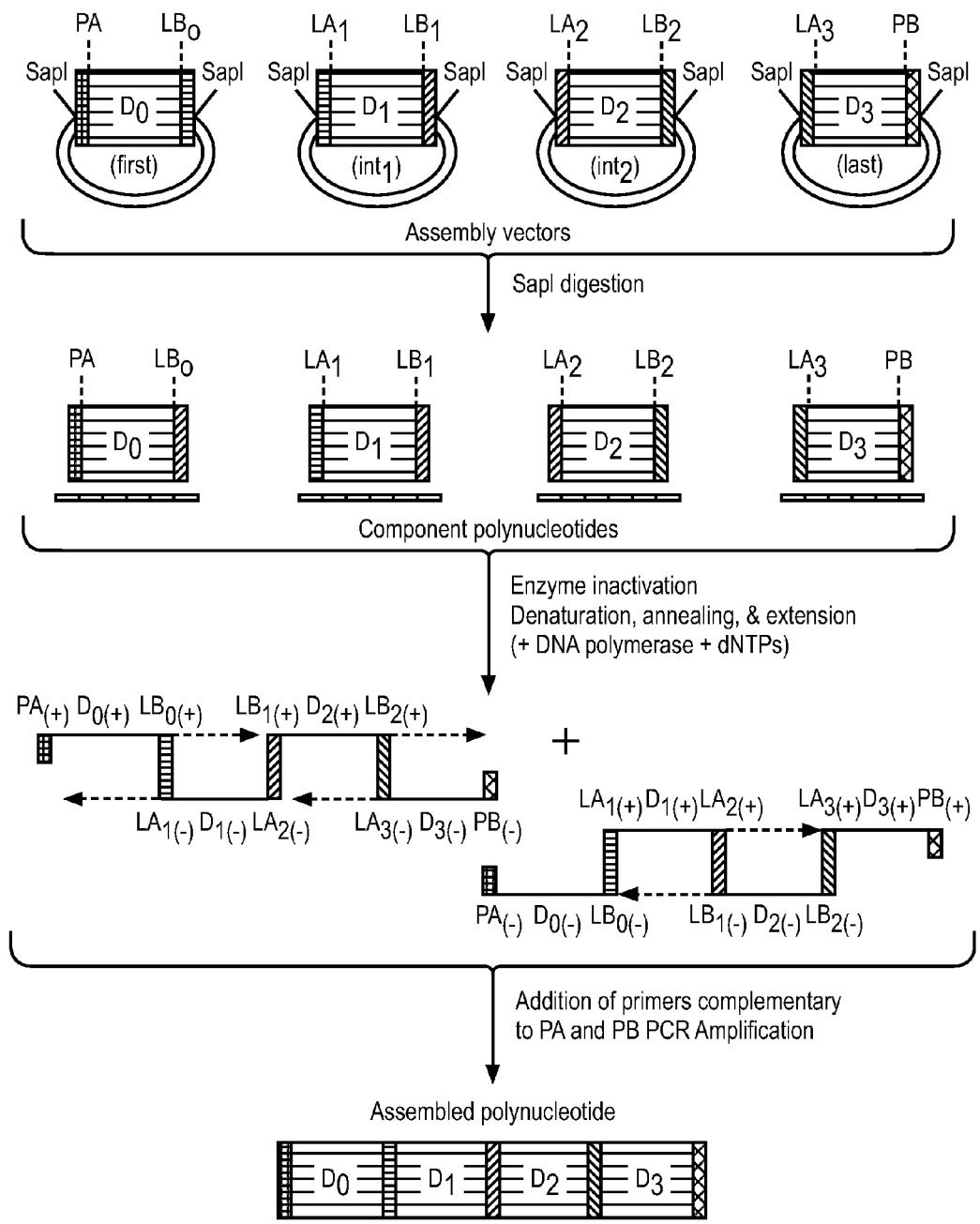

FIG. 11 presents an exemplary method of assembling, i.e., "stitching" a assembled polynucleotide from four (4) component polynucleotides. Assembly vectors comprising DNA segments to be assembled are pooled in a single tube and digested with SapI to release component polynucleotide fragments from the assembly vector backbones. Following heat inactivation of SapI, the component polynucleotide fragments are subjected to denaturing conditions, followed by annealing conditions sufficient for hybridization of the complementary annealable linker pairs. Following primer extension in the presence of DNA polymerase and dNTPs, primers complementary to PA and PB are added, followed by traditional PCR amplification. An assembled polynucleotide comprising component polynucleotides $D_0$, $D_1$, $D_2$, and $D_3$ assembled in a 5' to 3' direction is produced as a result of the assembling reaction.

Figure 12:
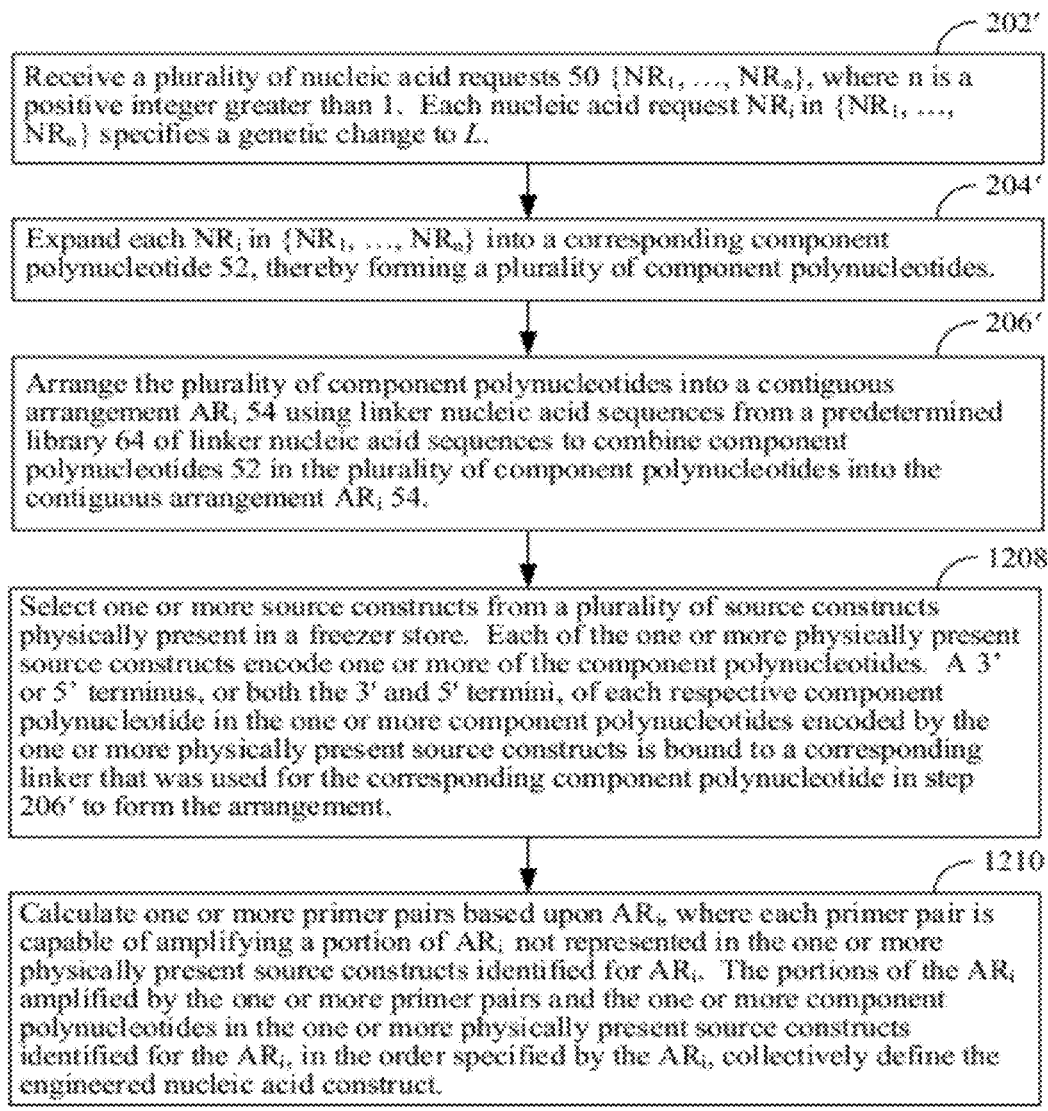

FIG. 12 illustrates an exemplary method for defining an engineered nucleic acid construct for integration into a genomic locus, in which a single arrangement of component polynucleotides that encodes a candidate for the engineered nucleic acid construct is computed and the availability of component polynucleotides in the arrangement in a freezer store is determined, in accordance with an embodiment of the present disclosure.

Figure 13:
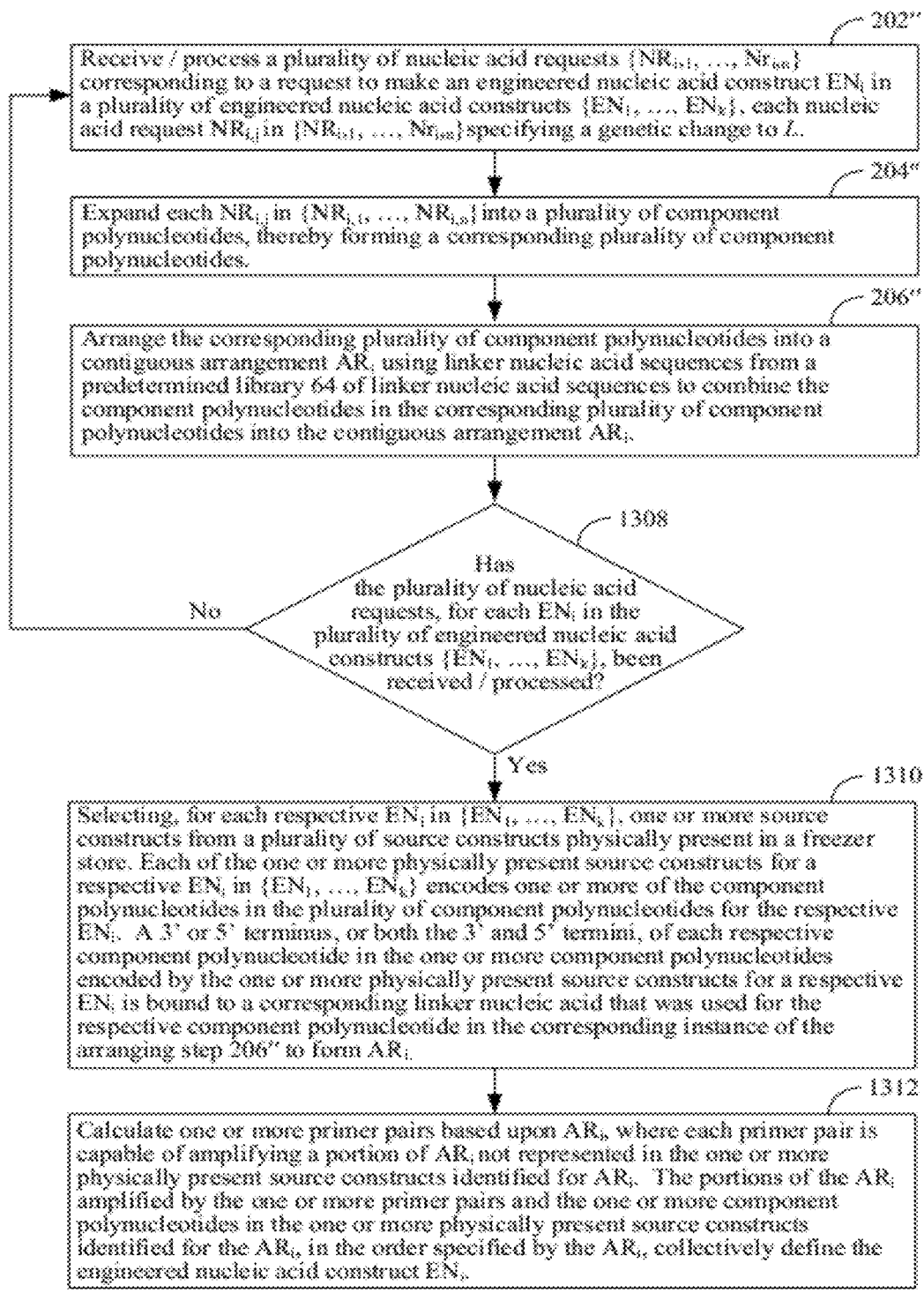

FIG. 13 illustrates an exemplary method for defining a plurality of engineered nucleic acid constructs for integration into a genomic locus, in which several different pluralities of nucleic acid requests {$NR_1$, ..., $NR_n$} are received and, for each respective plurality of nucleic acid requests {$NR_1$, ..., $NR_n$}, an arrangement of component polynucleotides that effect the nucleic acid requests of the respective plurality of nucleic acid requests is formed and the availability of component polynucleotides for the arrangement in a freezer store is determined, in accordance with an embodiment of the present disclosure.

Figure 14:
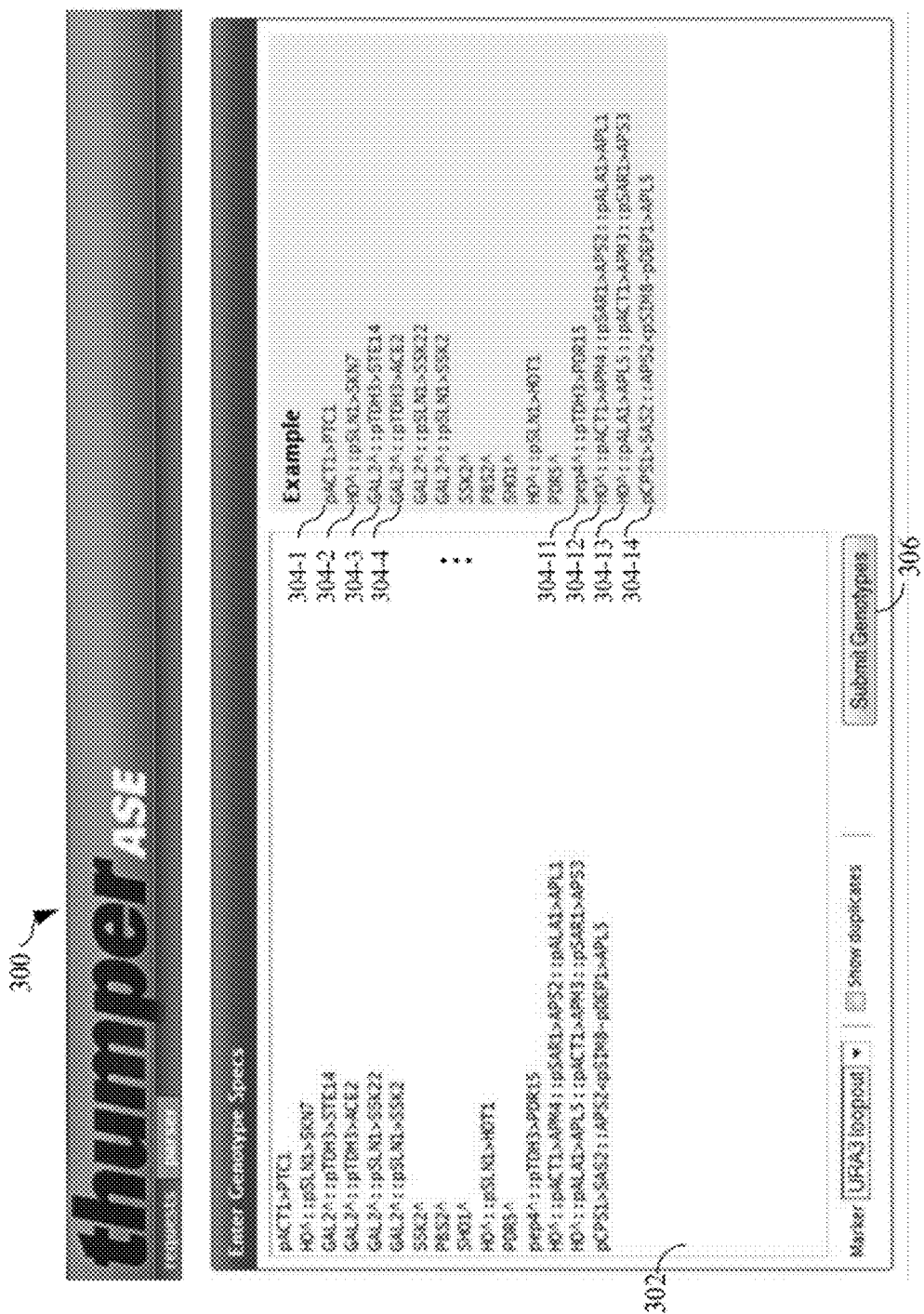

FIG. 14 illustrates a graphical user interface upon inputting one or more pluralities of nucleic acid requests, where each of the one or more pluralities of nucleic acid requests specifies a set of genetic changes that are to be made to a locus, in accordance to an embodiment of the present disclosure.

Figure 15:
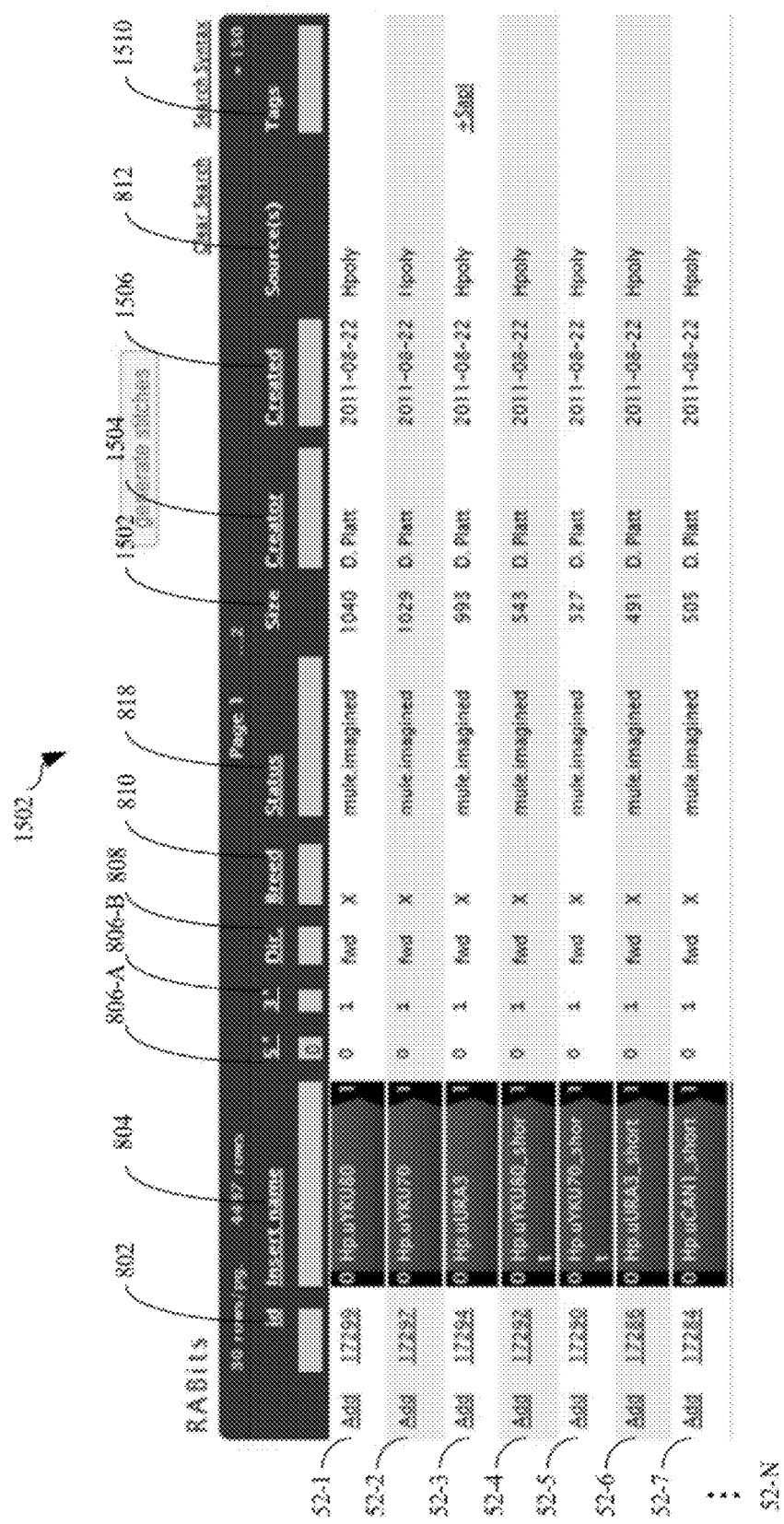

FIG. 15 illustrates a graphical user interface for identifying component polynucleotides in a freezer store in accordance with an embodiment of the present disclosure.

Figure 16:
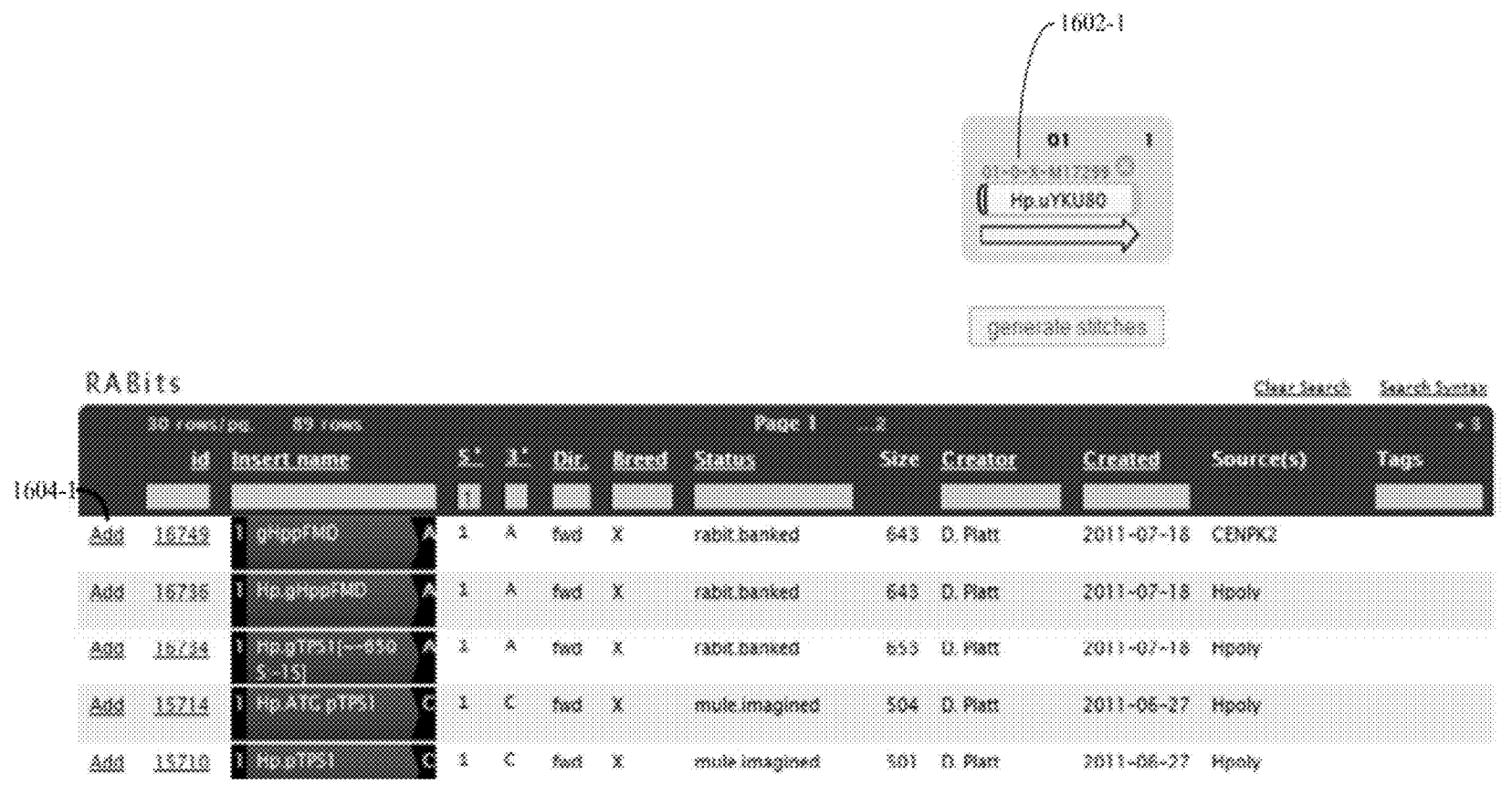

FIG. 16 illustrates a graphical user interface for identifying component polynucleotides in a freezer store, in which a first component polynucleotide has been selected from the freezer store, in accordance with an embodiment of the present disclosure.

Figure 17:
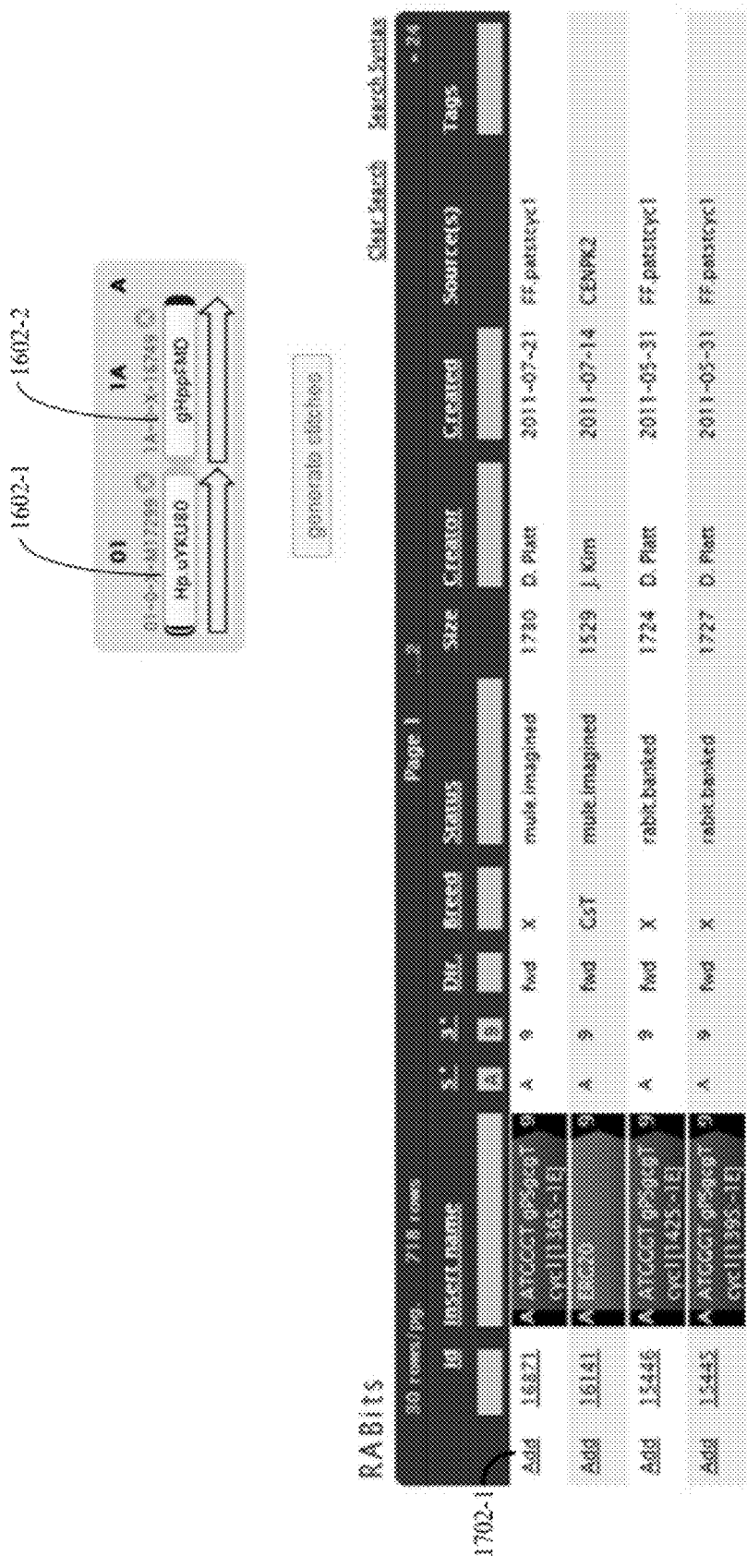

FIG. 17 illustrates a graphical user interface for identifying component polynucleotides in a freezer store, in which a second component polynucleotide has been selected from the freezer store and an icon for the second component polynucleotide is aligned with an icon for a first component polynucleotide, in accordance with an embodiment of the present disclosure.

Figure 18:
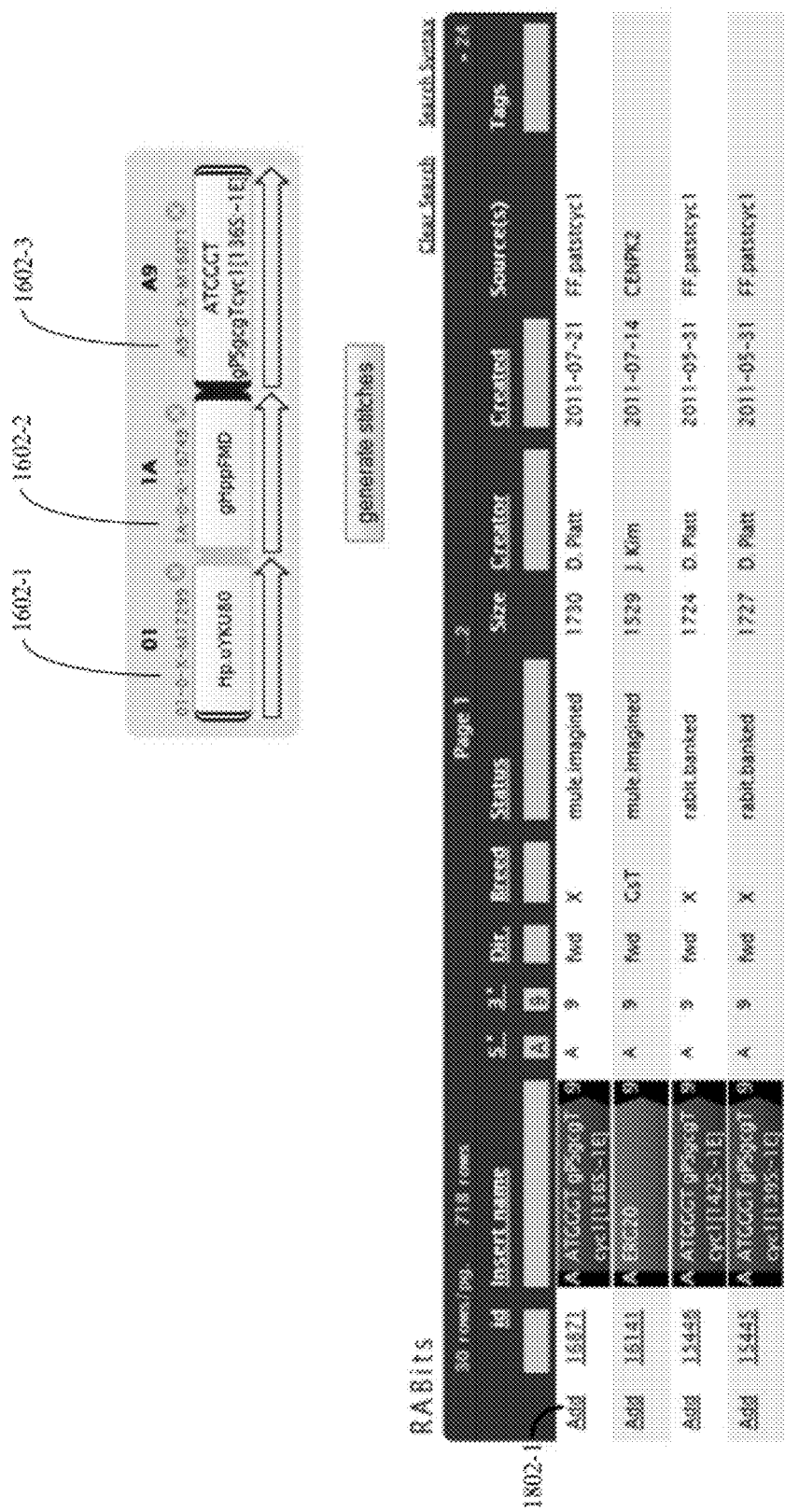

FIG. 18 illustrates a graphical user interface for identifying component polynucleotides in a freezer store, in which a third component polynucleotide has been selected from the freezer store and an icon for the third component polynucleotide is aligned with icons for a first and a second component polynucleotide, in accordance with an embodiment of the present disclosure.

Figure 19:
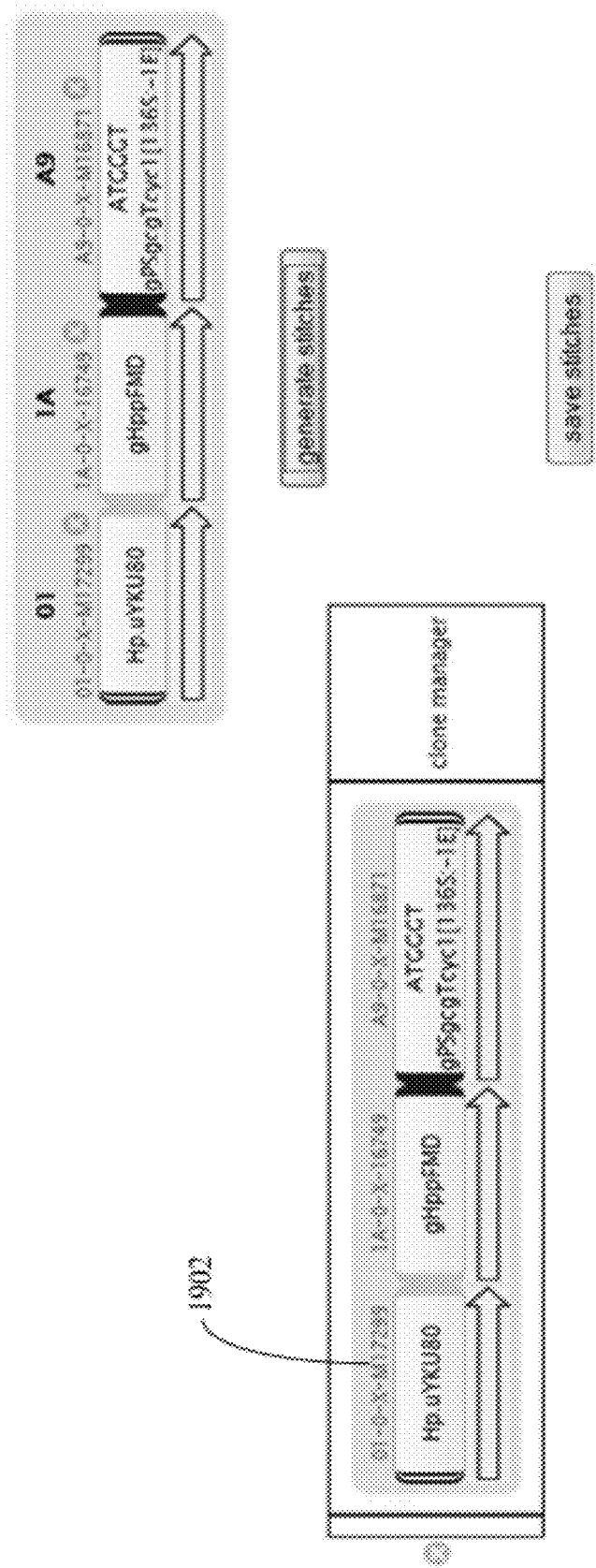

FIG. 19 illustrates a graphical user interface for identifying component polynucleotides in a freezer store, in which selected component polynucleotides are sent to a clone manager as a proposed engineered nucleic acid construct, in accordance with an embodiment of the disclosure.

Figure 20:
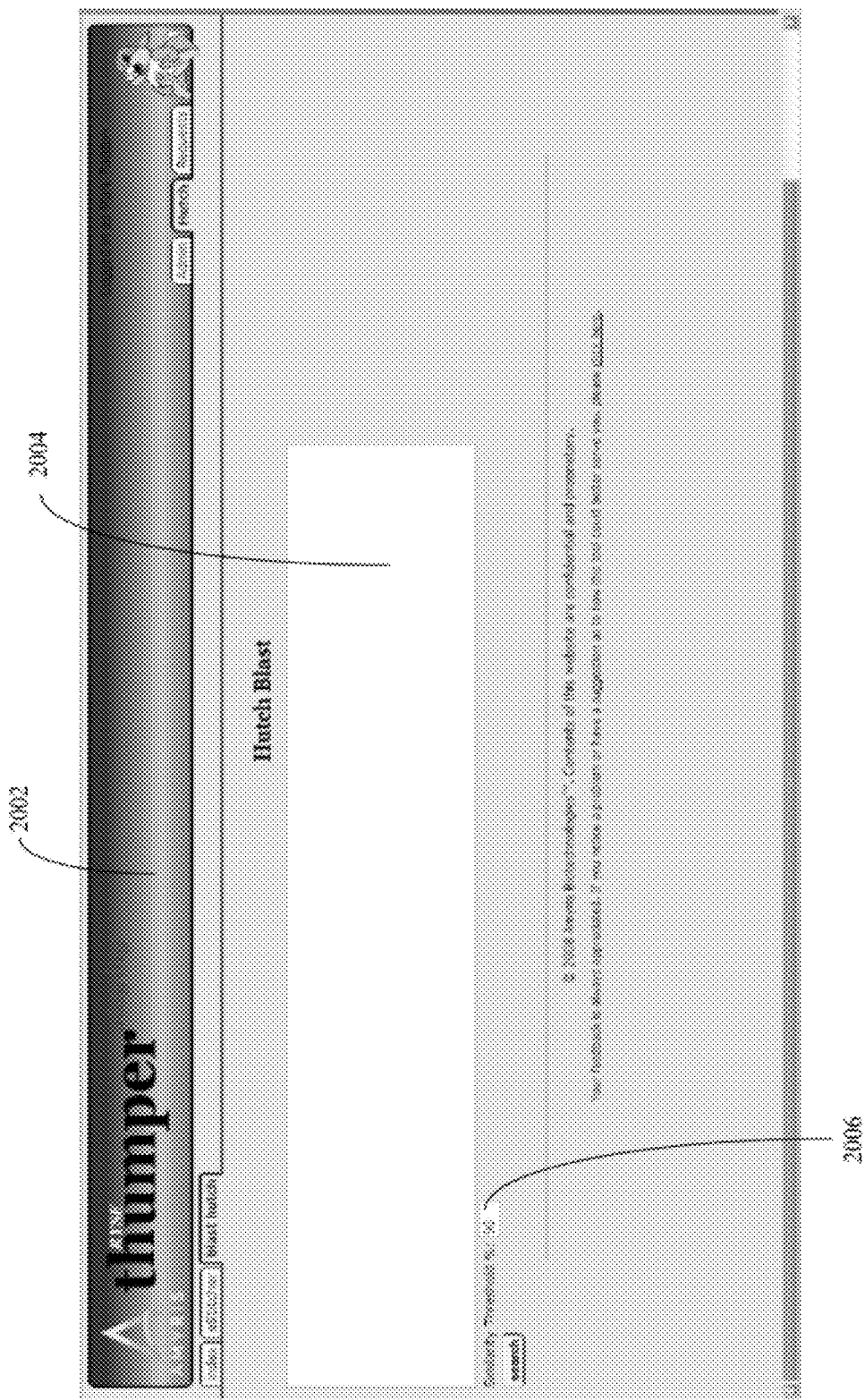

FIG. 20 illustrates a graphical user interface for searching for polynucleic acid sequences in a freezer store database that match a query polynucleic acid sequence. A user pastes or types a polynucleic acid sequence into an interface box and all of the possible matches that exceed a threshold criterion are displayed.

Figure 21:
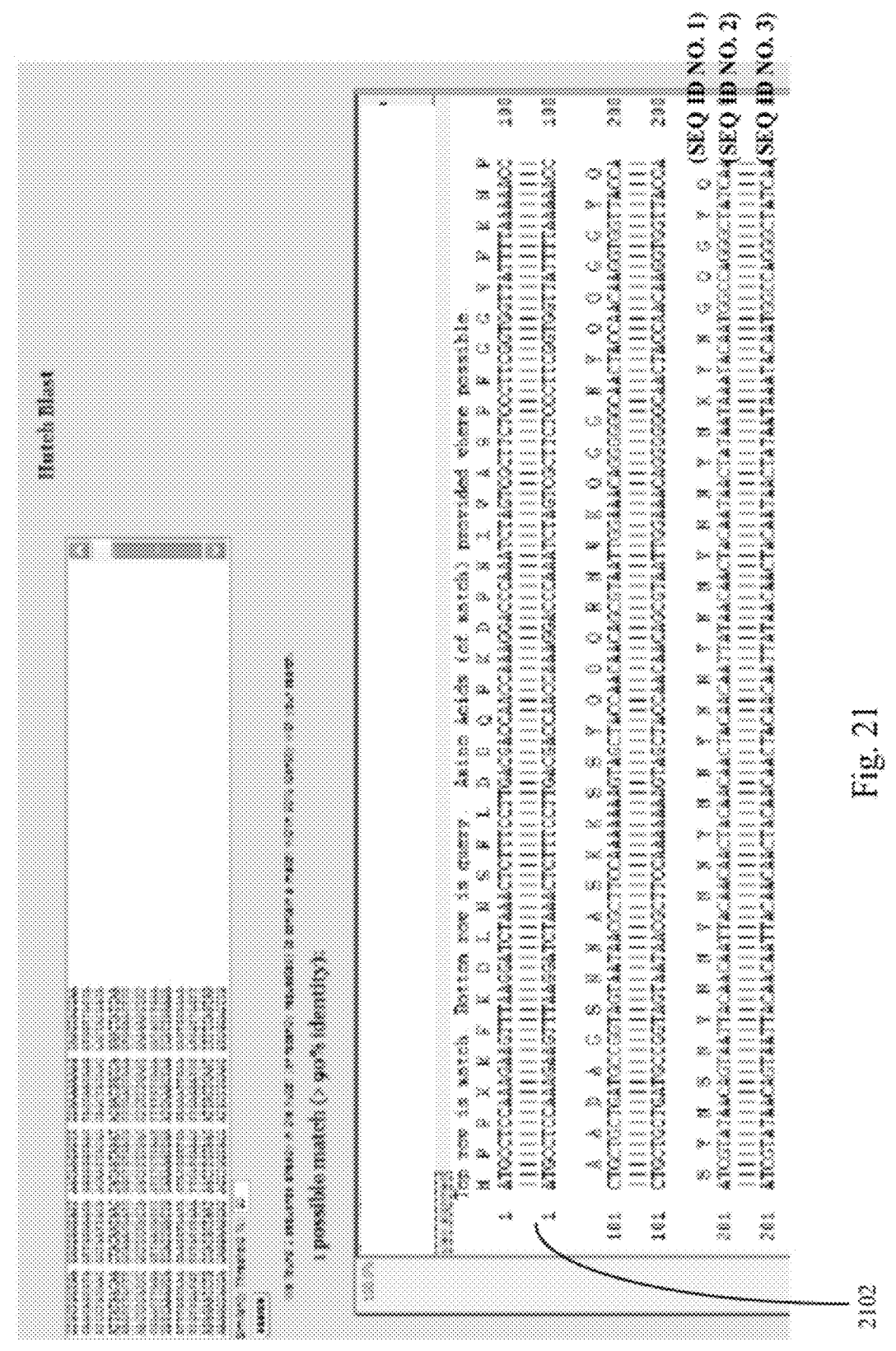

FIG. 21 illustrates a graphical user interface for searching polynucleic acid sequences in a freezer store database that match a query polynucleic acid sequence. After a user pastes or types the query polynucleic acid sequence into an interface box, an alignment of all of the possible matches against the query polynucleic acid sequence that exceed a threshold criterion is displayed.

Like reference numerals refer to corresponding parts throughout the several views of the drawings.

5. DETAILED DESCRIPTION OF THE EMBODIMENTS

5.1 Definitions

As used herein, the term "locus" refers to the chromosomal position at which a gene resides. In addition to the intronic and exonic regions of the gene, a locus can include regions which regulate the expression of the gene product, e.g., promoter sequences, terminators, translational regulatory sequences such as ribosome binding sites and internal ribosome entry sites, enhancers, silencers, insulators, and boundary elements.

As used herein, the term "selectable marker" refers to wide variety of selectable markers that are known in the art (see, for example, Kaufman, *Meth. Enzymol.*, 185:487 (1990); Kaufman, *Meth. Enzymol.*, 185:537 (1990); Srivastava and Schlessinger, *Gene*, 103:53 (1991); Romanos et al., in DNA Cloning 2: Expression Systems, 2$^{nd}$ Edition, pages 123-167 (IRL Press 1995); Markie, *Methods Mol. Biol.*, 54:359 (1996); Pfeifer et al., *Gene*, 188:183 (1997); Tucker and Burke, *Gene*, 199:25 (1997); Hashida-Okado et al., *FEBS Letters*, 425:117 (1998)), each of which is hereby incorporated by reference in their entirety for their teachings on selectable markers. One type of selectable marker is a drug resistant marker. A drug resistant marker enables cells to detoxify an exogenous drug that would otherwise kill the cell. Illustrative examples of drug resistant markers include, but are not limited to, those which confer resistance to antibiotics such as ampicillin, tetracycline, kanamycin, bleomycin, streptomycin, hygromycin, neomycin, ZEOCIN™, and the like. In other embodiments, the selectable marker is an auxotrophic marker. An auxotrophic marker allows cells to synthesize an essential component, usually an amino acid, while grown in media that lacks that essential component. Selectable auxotrophic gene sequences include, for example, hisD, which allows growth in histidine free media in the presence of histidinol. Other selectable markers include a bleomycin-resistance gene, a metallothionein gene, a hygromycin B-phosphotransferase gene, the AURI gene, an adenosine deaminase gene, an aminoglycoside phosphotransferase gene, a dihydrofolate reductase gene, a thymidine kinase gene, a xanthine-guanine phosphoribosyltransferase gene, and the like.

As used herein, the terms "polynucleotide" and "nucleic acid sequence" interchangeably refer to a polymer composed of nucleotide units as would be understood by one of skill in the art. Preferred nucleotide units include but are not limited to those comprising adenine (A), guanine (G), cytosine (C), thymine (T), and uracil (U). Useful modified nucleotide units include but are not limited to those comprising 4-acetylcytidine, 5-(carboxyhydroxylmethyl)uridine, 2-O-methylcytidine, 5-carboxymethylaminomethyl-2-thiouridine, 5-carboxymethylamino-methyluridine, dihydrouridine, 2-O-methylpseudouridine, 2-O-methylguanosine, inosine, N6-isopentyladenosine, 1-methyladenosine, 1-methylpseudouridine, 1-methylguanosine, 1-methylinosine, 2,2-dimethylguanosine, 2-methyladenosine, 2-methylguanosine, 3-methylcytidine, 5-methylcytidine, N6-methyladenosine, 7-methylguanosine, 5-methylaminomethyluridine, 5-methoxyaminomethyl-2-thiouridine, 5-methoxyuridine, 5-methoxycarbonylmethyl-2-thiouridine, 5-methoxycarbonylmethyluridine, 2-methylthio-N6-isopentyladenosine, uridine-5-oxyacetic acid-methylester, uridine-5-oxyacetic acid, wybutoxosine, wybutosine, pseudouridine, queuosine, 2-thiocytidine, 5-methyl-2-thiouridine, 2-thiouridine, 4-thiouridine, 5-methyluridine, 2-O-methyl-5-methyluridine, 2-O-methyluridine, and the like. Polynucleotides include naturally occurring nucleic acids, such as deoxyribonucleic acid ("DNA") and ribonucleic acid ("RNA"), as well as nucleic acid analogs. Nucleic acid analogs include those that include non-naturally occurring bases, nucleotides that engage in linkages with other nucleotides other than the naturally occurring phosphodiester bond or that include bases attached through linkages other than phosphodiester bonds. Thus, nucleotide analogs include, for example and without limitation, phosphorothioates, phosphorodithioates, phosphorotriesters, phosphoramidates, boranophosphates, methylphosphonates, chiral-methyl phosphonates, 2-O-methyl ribonucleotides, peptide-nucleic acids (PNAs), and the like.

As used herein, an "engineered nucleic acid construct" refers to a polynucleotide produced by the methods of polynucleotide assembly described herein. The assembled polynucleotide can be comprised of the two or more component polynucleotides. In some embodiments, the assembled polynucleotide comprises 2, 3, 4, 5, 6, 7, 8, 9, 10, 11, 12, 13, 14, 15 or more component polynucleotides. Assembled polynucleotide length can range from about 100 to about 20,000 nucleotides, or more. In some embodiments, the assembled polynucleotide length ranges from about 200 to about 10,000, about 200 to about 8000, about 200 to about 5000, about 200 to about 3000, or about 200 to about 1000 nucleotides. In other embodiments, the assembled polynucleotide length can range from about 200 to about 2000, about 2000 to about 5000, about 5000 to about 10,000, about 10,000 to about 20,000, or greater than 20,000 nucleotides.

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

As used herein, a "component polynucleotide" refers to a polynucleotide sequence that can be assembled together to form an "engineered nucleic acid construct" using the methods of polynucleotide assembly described herein. A "component polynucleotide", alternately referred to as "bits" herein, refers to any isolated or isolatable molecule of DNA. Useful examples include but are not limited to a protein-coding sequence, reporter gene, fluorescent marker coding sequence, promoter, enhancer, terminator, intron, exon, poly-A tail, multiple cloning site, nuclear localization signal, mRNA stabilization signal, selectable marker, integration loci, epitope tag coding sequence, degradation signal, or any other naturally occurring or synthetic DNA molecule. In some embodiments, the DNA segment can be of natural origin. Alternatively, a DNA segment can be completely of synthetic origin, produced in vitro. Furthermore, a DNA segment can comprise any combination of isolated naturally occurring DNA molecules, or any combination of an isolated naturally occurring DNA molecule and a synthetic DNA molecule. For example, a DNA segment may comprise a heterologous promoter operably linked to a protein coding sequence, a protein coding sequence linked to a poly-A tail, a protein coding sequence linked in-frame with a epitope tag coding sequence, and the like.

As used herein, the term "encode," as used in the context of a construct, for example a physically present source construct "encoding" a component polynucleotide, means that the source construct is a nucleic acid molecule that comprises the nucleic acid sequence which defines the component polynucleotide. For example, where the component polynucleotide is a promoter, the source construct that "encodes" this component polynucleotide comprises the nucleotide sequence of the promoter.

"Complementary" refers to the topological compatibility or matching together of interacting surfaces of two polynucleotides as understood by those of skill in the art. Thus, two sequences are "complementary" to one another if they are capable of hybridizing to one another to form a stable antiparallel, double-stranded nucleic acid structure. A first polynucleotide is complementary to a second polynucleotide if the nucleotide sequence of the first polynucleotide is substantially identical to the nucleotide sequence of the polynucleotide binding partner of the second polynucleotide, or if the first polynucleotide can hybridize to the second polynucleotide under stringent hybridization conditions. Thus, the polynucleotide whose sequence 5'-TATAC-3' is complementary to a polynucleotide whose sequence is 5'-GTATA-3'.

"Primer" refers to a polynucleotide sequence that is capable of specifically hybridizing to a polynucleotide template sequence, e.g., a primer binding segment, and is capable of providing a point of initiation for synthesis of a complementary polynucleotide under conditions suitable for synthesis, i.e., in the presence of nucleotides and an agent that catalyzes the synthesis reaction (e.g., a DNA polymerase). The primer is complementary to the polynucleotide template sequence, but it need not be an exact complement of the polynucleotide template sequence. For example, a primer can be at least about 80, 85, 90, 95, 96, 97, 98, or 99% identical to the complement of the polynucleotide template sequence. A primer can be of variable length but generally is at least 15 bases. In some embodiments, the primer is between 15 and 35 bases long. In some embodiments, the primer is more than 35 bases long. In other embodiments, the primer has a melting temperature ($T_m$), i.e., the temperature at which one half of the DNA duplex will dissociate to become single stranded, of at least 50° C. In other embodiments, the primer has a $T_m$ between about 50° C. and 70° C. In still other embodiments, the primer does not form appreciable DNA or RNA secondary structures so as to not impact the efficiency of hybridization to the polynucleotide template sequence.

As used herein, the term "primer binding segment" is a polynucleotide sequence that binds to a primer so as to provide a point of initiation for synthesis of a complementary polynucleotide under conditions suitable for synthesis. In some embodiments, the primer binding sequence is one of the annealable linkers of the present invention. A sequence is a primer binding sequence instead of an annealable linker by the absence of a complementary linker within a given set of assembly vectors or component polynucleotides within an assembly composition. In some embodiments, the primer binding segment can function as a genomic targeting sequence, e.g., an upstream or downstream genomic targeting sequence.

As used herein, the term "linker nucleic acid sequence" and "annealable linker sequence" are used interchangeably and refer to a polynucleotide sequence that flanks a DNA segment within an entry vector or assembly vector. Upon excision of a component polynucleotide from an assembly vector, and denaturation of the component polynucleotide, an annealable linker is capable of specifically hybridizing to a complementary annealable linker sequence of an adjacent component polynucleotide in a polynucleotide assembly reaction, as described herein. An annealable linker, upon annealing with a complementary linker strand, can provide a point of initiation for synthesis of a complementary polynucleotide.

As used herein, the term "vector" is used in reference to extrachromosomal nucleic acid molecules capable of replication in a cell and to which an insert sequence can be operatively linked so as to bring about replication of the insert sequence. Useful examples include but are not limited to circular DNA molecules such as plasmid constructs, phage constructs, cosmid vectors, etc., as well as linear nucleic acid constructs (e.g., lambda phage constructs, bacterial artificial chromosomes (BACs), yeast artificial chromosomes (YACs), etc.). A vector may include expression signals such as a promoter and/or a terminator, a selectable marker such as a gene conferring resistance to an antibiotic, and one or more restriction sites into which insert sequences can be cloned. Vectors can have other unique features (such as the size of DNA insert they can accommodate).

As used herein, the term "entry vector" refers to a cloning vector plasmid that can serve as a parental vector for the preparation of an assembly vector to be used in the polynucleotide assembly methods provided herein. An entry vector comprises two annealable linker sequences, or an annealable linker sequence and a primer binding segment, which flank restriction sites that can be utilized for the introduction of a DNA segment to form an assembly vector. As used herein, an "assembly vector" refers to an entry vector to which a DNA segment has been introduced. An assembly vector can be used in the polynucleotide assembly methods described herein to provide a component polynucleotide to be assembled into a assembled polynucleotide.

As used herein, the term "assembly vector" refers to a vector comprising one annealable linker sequence, two annealable linker sequences, or an annealable linker sequence and a primer binding segment, and a DNA segment.

As used herein, the term "restriction enzyme" or "restriction endonuclease" refers to a member or members of a classification of catalytic molecules that bind a cognate sequence of DNA and cleave the DNA molecule at a precise location within that sequence. Restriction endonucleases include Type IIS restriction endonucleases. This class of enzymes differs from other restriction endonucleases in that the recognition sequence is separate from the site of cleavage. Some examples of Type IIS restriction enzymes include AlwI, BsaI, BbsI, BbuI, BsmAI, BsrI, BsmI, BspMI, EarI, Esp3I, FokI, HgaI, HphI, LguI, MboII, MnlI, PleI, SapI, SchI, SfaNi, and the like. Many of these restriction endonucleases are available commercially and are well known to those skilled in the art.

As used herein, the term "genomic targeting sequence" refers to a nucleotide sequence that is present in the genome of a host cell at a site at which a polynucleotide of the invention is to be inserted by host cell mediated homologous recombination. The terms "upstream genomic targeting sequence" and "downstream genomic targeting sequence" refer to genomic targeting sequences that are located upstream and downstream of each other in the genome of a host cell. An example of a genomic targeting sequence is a locus.

As used herein, the term "chromosomal targeting sequence" refers to a nucleotide sequence that is present in a chromosome of a host cell at a site at which a polynucleotide of the invention is to be inserted by host cell mediated homologous recombination. The terms "upstream chromosomal targeting sequence" and "downstream chromosomal targeting sequence" refer to chromosomal targeting sequences that are located upstream and downstream of each other in a chromosome of a host cell. An example of a genomic targeting sequence is a locus.

The term "codon substitution" refers to a process of altering a polynucleotide sequence by changing one or more of the codons encoding one or more amino acids within a polypeptide, though without altering the sequence of the encoded polypeptide.

5.2 Methods of Polynucleotide Assembly

In one aspect, the present disclosure provides rapid, robust, and high-throughput methods for the ordered assembly of a plurality of component polynucleotides into one or more assembled polynucleotides, also termed engineered nucleic acid constructs.

The systems, compositions and methods provided herein allow for rapid and ordered assembly, or "stitching," of component polynucleotides into assembled polynucleotides, termed engineered nucleic acid constructs. The disclosed systems, compositions and methods are particularly advantageous because they make use of available resources to reduce the cost of synthesizing new engineered nucleic acid constructs. For instance, if component polynucleotides that form part of a desired engineered nucleic acid construct are already available in a freezer store, an optimal combination of such component polynucleotides are selected and suitable primer pairs are calculated for the missing portions of the engineered nucleic acid construct, i.e., those not already available in a freezer store. This minimizes the design of new primer pairs and subcloning from a genomic library, or other nucleic acid source, that needs to be performed in order to synthesize the desired engineered nucleic acid construct thereby increasing the speed at which such an engineered nucleic acid construct may be made while at the same time reducing costs. Using the disclosed systems, compositions and methods, a high throughput scheme for making engineered nucleic acid constructs is realized.

Thus, in one aspect, provided herein is a user-friendly interface for the computer-implemented design and assembly of nucleic acid constructs. The systems, compositions and methods provided herein enable a synthetic biologist to engineer a desired nucleic acid construct to introduce into a host cell genome. In particular, the systems and methods provide for assembly into a single assembled polynucleotide of a number of functional DNA elements, including but not limited to protein-coding sequences, reporter genes, fluorescent marker coding sequences, promoters, enhancers, terminators, introns, exons, poly-A tails, multiple cloning sites, nuclear localization signals, mRNA stabilization signals, selectable markers, integration loci, epitope tag coding sequences, and degradation signals. The methods can be used for the assembly of any type of assembled polynucleotide, including but not limited to synthetic genes, constructs, cloning vectors, expression vectors, chromosomes, genomic integration constructs, genomes, and DNA libraries. Furthermore, the methods can be used to assemble DNA segments in a single reaction without need for manipulation and characterization of intermediate products.

In some embodiments, the methods include those disclosed in U.S. Pat. No. 8,110,360, which is hereby incorporated by reference in its entirety. In some embodiments, the disclosed methods utilize circular nucleic acid vectors, termed assembly vectors, that each comprise a DNA segment, D, flanked by an annealable linker sequence (e.g., LA or LB), a pair of annealable linker sequences (e.g., LA and LB), or an annealable linker sequence and a primer binding segment (e.g., LA and PB or LB and PA), and a pair of restriction sites, RA and RB (FIG. 9, where the sites SapI illustrates both RA and RB).

Restriction endonuclease digestion of a plurality of assembly vectors at restriction sites RA and RB generates a plurality of component polynucleotides comprising the elements 5'-LA-D-3', 5'-D-LB-3', 5'-LA-D-LB-3', 5'-LA-D-PB-3', or 5'-LB-D-PA-3' (FIG. 10). In the disclosed methods, annealable linker sequences LA and LB provide the component polynucleotides with complementary termini that are utilized in a splice overlap extension assembly reaction followed by polymerase chain reaction (SOE/PCR) to assemble the component polynucleotides into an assembled polynucleotide with an ordered sequence.

In some embodiments, provided herein are methods of assembling a plurality of component polynucleotides into one or more assembled polynucleotides, comprising the steps of:
(a) digesting an assembly composition with one or more restriction endonucleases to generate a components composition, the assembly composition comprising:
  (i) one or more first nucleic acid molecules, wherein each first nucleic acid molecule is circular and comprises, in a 5' to 3' orientation, a first restriction site $RA_0$, any primer binding segment selected from the group PA, any DNA segment selected from the group $D_0$, an annealable linker sequence $LB_0$, and a second restriction site $RB_0$;
  (ii) one or more intermediate nucleic acid molecules wherein each intermediate nucleic acid molecule n is circular and comprises, in a 5' to 3' orientation, a first restriction site $RA_n$, a first annealable linker sequence $LA_n$, any DNA segment selected from the group $D_n$, a second annealable linker sequence $LB_n$, and a second restriction site $RB_n$, and wherein n represents an integer from one to the number of intermediate nucleic acid molecules; and
  (iii) one or more last nucleic acid molecules, wherein each last nucleic acid molecule is circular and comprises, in a 5' to 3' orientation, a first restriction site $RA_m$, an annealable linker sequence $LA_m$, a DNA segment selected from the group $D_m$, any primer binding segment selected from the group PB, a second restriction site $RB_m$ wherein m represents an integer one greater than the number of intermediate nucleic acid molecules; whereupon cleavage of restriction sites $RA_0$ through $RB_m$ and denaturation of the resulting linear nucleic acid molecules, each annealable linker sequence $LB_{(p-1)}$ is capable of hybridizing to the complement of annealable linker sequence $LA_p$, wherein n is an integer that varies from 1 to (m−1), wherein p represents an integer from 1 to m, and wherein each group $D_0, \ldots D_n, \ldots$ and $D_m$ consists of one or more DNA segments;

wherein the one or more restriction endonucleases are capable of cleaving the restriction sites $RA_0$ through $RB_m$; and (b) contacting the components composition with DNA polymerase, deoxyribonucleoside triphosphates and one or more first primers and one or more second primers, under conditions suitable for denaturation of the nucleic acid molecules, annealing of annealable linker sequence $LB_{(p-1)}$ to annealable linker sequence $LA_p$, and extension therefrom; wherein each said first primer is capable of hybridizing to one of said primer binding segments selected from the group PA and each said second primer is capable of hybridizing to one of said primer binding segments selected from the group PB; and subjecting the components composition to polymerase chain reaction, where a polynucleotide is assembled which comprises, in a 5' to 3' orientation, one DNA segment selected from each of the groups $D_0, \ldots D_n, \ldots$ and $D_m$. In the method, p represents the integers from 1 to m.

In the example illustrated in FIG. 11, the assembly composition from which the assembled polynucleotide is generated comprises four input assembly vectors, denoted "first," "intermediate 1 ($int_1$)," "intermediate 2 ($int_2$)," and "last." Each assembly vector comprises a DNA segment flanked either by an annealable linker sequence and a primer binding segment, or by two annealable linker sequences. Specifically, DNA segment $D_0$ is flanked by 5' primer binding segment PA and 3' annealable linker sequence $LB_0$. DNA segment $D_1$ is flanked by 5' and 3' annealable linker sequences $LA_1$ and $LB_1$, and DNA segment $D_2$ is flanked by 5' and 3' annealable linker sequences $LA_2$ and $LB_2$. DNA segment $D_3$ is flanked by 3' primer binding segment PB and 5' annealable linker sequence $LA_3$. The 5'-PA-D-LB-3',5'-LA-D-LB-3', or 5'-LA-D-PB-3' elements in the assembly vectors are further flanked by SapI restriction endonuclease sites.

In the first step of the assembly reaction shown in FIG. 11, the assembly composition is digested with SapI, resulting in the excision of component polynucleotides, comprising the elements 5'-PA-D-LB-3',5'LA-D-LB-3', or 5'-LA-D-PB-3', from the assembly vector backbones into a components composition. Because Sap I is a Type IIS restriction endonuclease, its recognition site is distal to its cleavage site, and cleavage occurs outside of its recognition sequence. This property makes Type IIS restriction endonucleases particularly useful in the assembly of a polynucleotide according to the methods provided herein, since polynucleotides can be assembled which do not comprise a restriction-site scar, which may otherwise result from cleavage of restriction sites RA and RB with a non-TypeIIS restriction endonuclease. Referring to FIG. 10, the Type IIS recognition site is 5' of the corresponding cleavage site for each of $RA_0$, $RA_n$, and $RA_m$, and 3' of its cleavage site $RB_0$, $RA_n$, and $RA_m$. Thus, restriction sites $RA_0$ through $RB_m$ are oriented so that cleavage by one or more Type IIS restriction endonucleases capable of cleaving $RA_0$ through $RB_m$ results in separation of $RA_0$ from $D_0$, $LB_0$ from $RB_0$, $RA_n$, from $LA_n$, $LB_n$, from $RB_n$, $RA_m$ from $LA_m$, and $D_m$ from $RB_m$, wherein resultant linearized nucleic acid molecules comprising $D_0$, $LB_0$, $RA_n$, $LB_n$, $LA_m$ or $D_m$ do not comprise any of $RA_0$ through $RB_m$. As a consequence, the resulting component polynucleotides do not include any trace of either the restriction enzyme's recognition or cleavage sites. As a result, the inventive methods of polynucleotide assembly can be used to transform host cells multiple times without the introduction of sequence repeats which may cause genetic instability.

Subsequently, the restriction endonuclease is optionally inactivated. If inactivation is desired, any method known in the art for inactivating endonuclease enzyme activity may be employed, including column or gel-based purification methods. One convenient method is heat inactivation, e.g., at 65° for 20 minutes, which requires little or no manipulation of the components composition outside of the reaction tube.

Assembly of the component polynucleotides into an assembled polynucleotide is enabled by sequence duplexes formed by overlapping strands of complementary termini among the component polynucleotides. Specifically, the annealable linker sequences are designed such that annealable linker sequence $LB_0$ can hybridize to the complement of annealable linker sequence $LA_1$, annealable linker sequence $LB_1$ can hybridize to the complement of annealable linker sequence $LA_2$, and annealable linker sequence $LB_2$ can hybridize to the complement of annealable linker sequence $LA_3$. Thus, in the second step of the assembly reaction, the component polynucleotides are subjected to denaturing conditions (e.g., heat) to generate single-stranded component polynucleotides, which concomitant with or subsequent to the denaturation step of the assembly reaction are contacted with a thermostable DNA polymerase and deoxyribonucleoside triphosphates.

The thermostable DNA polymerase can be any thermostable DNA polymerase deemed suitable by those of skill in the art. Thermostable DNA polymerases suitable for use in the present methods include but are not limited to *Thermus thermophilus* (Tth) DNA polymerase, *Thermus aquaticus* (Taq) DNA polymerase, *Thermotoga neopolitana* (Tne) DNA polymerase, *Thermotoga maritima* (Tma) DNA polymerase, *Thermococcus litoralis* (Tli or VENT™) DNA polymerase, *Pyrococcus furiosus* (Pfu or DEEPVENT™) DNA polymerase, *Pyrococcus woosii* (Pwo) DNA polymerase, *Bacillus sterothermophilus* (Bst) DNA polymerase, *Sulfolobus acidocaldarius* (SAC) DNA polymerase, *Thermoplasma acidophilum* (Tac) DNA polymerase, *Thermus flavus* (Tfl/Tub) DNA polymerase, *Thermus ruber* (Tru) DNA polymerase, *Thermus brockianus* (DYNAZYME™) DNA polymerase, *Methanobacterium thermoautotrophicum* (Mth) DNA polymerase, and mutants, variants, and derivatives thereof. Thermostable DNA polymerases having high fidelity (e.g., proofreading properties) and low error rates are preferred. In certain embodiments, the DNA polymerase is PHUSION™DNA Polymerase (New England Biolabs, Ipswich, Mass.). In other embodiments, the DNA Polymerase is PFUULTRA™II Fusion DNA Polymerase (Strategene/Agilent, La Jolla, Calif.).

The assembly reaction is then subjected to conditions that allow for strand elongation from the 3'-hydroxyl portions of the overlapping annealable linker sequences, during which the thermostable DNA polymerase fills in the portion between the overlapping annealable linker sequences. The assembly reaction is subjected to a limited number of repeating cycles of denaturation/annealing/extension (e.g., for 5-15 cycles) during which a substantial amount of double-stranded assembled polynucleotides are formed. During this cycling, the component polynucleotides act as both primers and template to generate a full length template for the assembled polynucleotide. In certain embodiments, the annealing and extension steps of the PCR can both be performed at 72° C.

In contrast to the annealable linker sequences LA and LB, the primer binding segments PA and PB are designed to not overlap with each other or any of the annealable linker sequences or DNA segments, but rather serve as binding sites for primers used to amplify the full length assembled polynucleotide. Thus, in steps 4 and 5 of the assembly reaction, primers complementary to primer binding segments PA and PB are added, and the composition is subjected to traditional PCR amplification conditions. The PCR amplification conditions can be any PCR amplification conditions deemed suitable by those of skill in the art, including those described in *PCR Technology: Principles and Applications for DNA Amplification*, ed. H A Erlich, Stockton Press, New York, N.Y. (1989); *PCR Protocols: A Guide to Methods and Applications*, eds. Innis, Gelfland, Snisky, and White, Academic Press, San Diego, Calif. (1990); Mattila et al. (1991) *Nucleic Acids Res.* 19: 4967; Eckert, K. A. and Kunkel, T. A. (1991) PCR Methods and Applications 1: 17; and U.S. Pat. Nos. 4,683,202 and 4,965,188, each of which are incorporated herein by reference. In certain embodiments, the PCR step of the assembly reaction comprises about 35 cycles of denaturation, annealing, and extension in the presence of primers complementary to primer binding segments PA and PB. In certain embodiments, the annealing and extension steps of the PCR can both be performed at 72°. However, one of skill in the art will understand that optimal conditions for successful amplification will depend on the thermostable DNA polymerase and the annealable linker sequences utilized, and these conditions may be adjusted accordingly.

Optionally, the assembled polynucleotide can be purified by any technique apparent to one of skill in the art, e.g., gel electrophoresis purification methods and used for a variety of purposes. For example, the assembled polynucleotide can be inserted into an expression vector backbone for sequence verification.

In other embodiments, the systems and methods also provide for the assembly of an assembled polynucleotide from a plurality of component polynucleotides not originating from a circular assembly vector. For example, linear polynucleotides, including DNA segments obtained by standard procedures known in the art, such as for example, PCR amplification, chemical synthesis, and the like, can be assembled using the aforementioned methods of assembly. In some embodiments, the linear polynucleotides comprise nucleic acid sequences that encode genes or genetic elements of interest (e.g., promoters, terminators, selectable markers, integration loci, epitope tags, localization signals, degradation signals, fluorescent markers, multiple cloning sites). In some embodiments, these nucleic acid sequences are flanked by one or two annealable linker sequences, LA and/or LB, or by an annealable linker sequence and a primer binding segment (e.g., LA and PB or LB and PA).

In some embodiments, the linear polynucleotides may be added to the assembly reaction at any stage prior to the SOE/PCR reaction or host cell mediated homologous recombination for assembly into the assembled polynucleotide. Thus, in some embodiments, the assembly methods can be used to assemble: (1) linear component polynucleotides derived from assembly vectors comprising one or two annealable linker sequences, or an annealable linker sequence and a primer binding segment, and generated by digestion of the assembly vectors; (2) vectorless linear DNA fragments flanked by one or two annealable linker sequences, or by an annealable linker sequence and a primer binding segment; and (3) combinations thereof.

Accordingly, in some embodiments, provided herein are methods of assembling a plurality of component polynucleotides into one or more assembled polynucleotides, comprising the steps of:
(a) providing a components composition comprising:
  (i) one or more first nucleic acid molecules, wherein each first nucleic acid molecule is linear and comprises, in a 5' to 3' orientation, any primer binding segment selected from the group PA, any DNA segment selected from the group $D_0$, and an annealable linker sequence $LB_0$;
  (ii) one or more intermediate nucleic acid molecules wherein each intermediate nucleic acid molecule n is linear and comprises, in a 5' to 3' orientation, a first annealable linker sequence $LA_n$, any DNA segment selected from the group $D_n$, and a second annealable linker sequence $LB_n$, wherein n represents an integer from one to the number of intermediate nucleic acid molecules; and
  (iii) one or more last nucleic acid molecules, wherein each last nucleic acid molecule is linear and comprises, in a 5' to 3' orientation, an annealable linker sequence $LA_m$, a DNA segment selected from the group $D_m$, and any primer binding segment selected from the group PB, wherein m represents an integer one greater than the number of intermediate nucleic acid molecules; whereupon denaturation of the resulting linear nucleic acid molecules, each annealable linker sequence $LB_{(p-1)}$ is capable of hybridizing to the complement of annealable linker sequence $LA_p$, wherein n is an integer that varies from 1 to (m−1), wherein p represents an integer from 1 to m, and wherein each group $D_0, \ldots D_n, \ldots$ and $D_m$ consists of one or more DNA segments;
and
(b) contacting the components composition with DNA polymerase, deoxyribonucleoside triphosphates and one or more first primers and one or more second primers, under conditions suitable for denaturation of the nucleic acid molecules, annealing of annealable linker sequence $LB_{(p-1)}$ to annealable linker sequence $LA_p$, and extension therefrom; wherein each said first primer is capable of hybridizing to one of said primer binding segments selected from the group PA and each said second primer is capable of hybridizing to one of said primer binding segments selected from the group PB; and subjecting the components composition to polymerase chain reaction,
where a polynucleotide is assembled which comprises, in a 5' to 3' orientation, one DNA segment selected from each of the groups $D_0, \ldots D_n, \ldots$ and $D_m$. In the method, p represents the integers from 1 to m.

In other embodiments, the methods of polynucleotide assembly provided herein comprise transforming a host cell with a plurality of linear polynucleotides, for example polynucleotides generated by standard procedures known in the art, such as PCR amplification, chemical synthesis, and the like, or by the methods of polynucleotide assembly described herein, and allowing the host cell to generate one or more assembled polynucleotides in vivo by homologous recombination. In a particular embodiment, the host cell combines the plurality of linear polynucleotides into a single combined polynucleotide by homologous recombination. Host cell transformants comprising the combined polynucleotides are selected by virtue of expressing a selectable marker that is generated in the process of combining the linear polynucleotides.

In some embodiments, one or more linear polynucleotides to be assembled in vivo comprises an annealable linker sequence LB that is homologous to an annealable linker sequence LA of another linear polynucleotide to be assembled, and that is of sufficient length to initiate host mediated homologous recombination. The host cell recombines the component polynucleotides at the regions of homology between the annealable linker sequences to form an assembled polynucleotide. Host cells comprising the assembled polynucleotide can be readily identified based on a selectable marker encoded by a DNA segment of the assembled polynucleotide. In some embodiments, the assembled polynucleotide comprises an upstream chromosomal targeting sequence and a downstream chromosomal targeting sequence, wherein both chromosomal targeting sequences are of sufficient length to initiate host mediated homologous recombination of the assembled polynucleotide with a target loci on a chromosome of the host cell.

The method is particularly useful for inserting relatively large pieces of polynucleotide into a target polynucleotide by homologous recombination. For chromosomal integration to occur, the combined polynucleotide must comprise an upstream genomic targeting sequence located 5' or 3' of the DNA segment and a downstream genomic targeting sequence located 3' or 5' of the coding sequence of the DNA segment, respectively. Genomic integration as used herein includes chromosomal integration, i.e., integration of a polynucleotide into a chromosome of a host cell. Suitable chromosomal integration sites in *Saccharomyces cerevisiae* include but are not limited to the NDT80, HO, GAL2, and GAL1-GAL 10-GAL7 locus. The method can also be useful for generating host cells comprising an extrachromosomally maintained polynucleotide, e.g., vectors and expression plasmids. The stability of either a chromosomally integrated or an extrachromosomally maintained combined polynucleotide is increased when the combined polynucleotide does not comprise identical annealable linker sequences or DNA segments arranged as direct repeats that can otherwise initiate additional homologous recombination events resulting in the excision of segments of the component polynucleotide. Therefore, in some embodiments, the assembled polynucleotides comprise unique annealable linker sequences and DNA segments. In other embodiments, the assembled polynucleotides contain one or more identical annealable linker sequences or DNA segments that upon combination of the assembled polynucleotides are arranged as inverted repeats in the combined polynucleotide.

In other embodiments, the systems, compositions and methods provided herein also provide for the assembly of the component polynucleotides into an assembled polynucleotide via chain reaction cloning using a thermostable ligase, as described for example, in U.S. Pat. No. 6,143,527, and Pachuk et al., *Gene* 243:19-25 (2000), each of which is hereby incorporated by reference in its entirety.

In brief, chain reaction cloning utilizes the specificity of Watson-Crick base pairing and the amplification capability of thermostable DNA ligases such as Ampligase® (Epicentre Technologies, Madison, Wis.). The method involves the use of two or more oligonucleotides called "bridge oligonucleotides." Each bridge oligonucleotide is designed to be complementary to the ends of two DNA molecules to be ligated. The oligonucleotides overlap the ligation junction, for example, by approximately 10-40 bases on each side, and ensure that the two single-stranded nucleic acid molecules are aligned correctly. Individual double-stranded nucleic acid molecules to be ligated can include, for example, component polynucleotides flanked by one or two full or partial annealable linker sequences, LA and/or LB, or by a full or partial annealable linker sequence and a full or partial primer binding segment (e.g., LA and PB or LB and PA). When utilizing chain reaction cloning as a method of polynucleotide assembly, complementarity between LA and LB is not required, and in certain embodiments, such complementarity is avoided so as to reduce competition for hybridization of the annealable linker or primer binding segment to the appropriate bridging oligonucleotides. The DNA molecules to be ligated are incubated with the bridge oligonucleotides and a thermostable DNA ligase, and heated, for example, to 94° C. to denature the double-stranded DNA. The sample is then cooled to a temperature that enables each bridge oligonucleotide to anneal to its two components in the single-stranded DNA molecules. The bridge oligonucleotide acts to bring the two single-stranded DNA termini into close proximity, where they can become a substrate for ligation. The DNA ligase joins the two nucleic acid molecules into a single, larger, composite nucleic acid molecule. To avoid non-specific annealing of oligonucleotides, the annealing temperature is not dropped below the melting temperature ($T_m$) of the oligonucleotides. In some embodiments, all of the oligonucleotides in a reaction are designed to have a similar $T_m$. The temperature is then brought up to 66° C., the optimal temperature for Ampligase®. The nucleic acid molecules are subsequently denatured so that the composite molecule formed by the ligated nucleic acid molecules and the template cease to hybridize to each. Each composite molecule then serves as a template for orienting unligated, single-stranded nucleic acid molecules. In subsequent cycles of the reaction, both the bridge oligonucleotide and product molecules act as templates for hybridization and ligation. After several cycles, composite nucleic acid molecules are generated from smaller nucleic acid molecules.

5.3 Exemplary System for Polynucleotide Assembly

The systems and methods described in Section 5.2 provide for the advantageous construction of engineered nucleic acid constructs. Detailed in this section are advantageous systems for obtaining each of the component polynucleotides necessary to construct such engineered nucleic acid constructs. The disclosed systems are particularly advantageous because they make use of existing component polynucleotides bound to linker nucleic acid sequences in an available freezer store when such existing component polynucleotides are available. The disclosed systems will rearrange the component polynucleotides, in silico, in order to discover a contiguous arrangement of component polynucleotides that will carry out the nucleic acid requests associated with an engineered nucleic acid construct, and the concomitant choice of linker nucleic acid sequences that the arrangement dictates, utilizing component polynucleotides available in the freezer store. Primers for the missing component polynucleotides, i.e., those not available in a freezer store, and their concomitant linker nucleic acid sequences, are then designed for synthesis. In this way, all the component polynucleotides, including the appropriate linker nucleic acid sequences linked to such component polynucleotides are prepared in the most economical fashion by exploiting the resources of the available freezer store. The component polynucleotides bound to linkers in the freezer store that match the component polynucleotides bound to linkers in the arrangement are retrieved from the freezer store while the missing component polynucleotides and their linkers are synthesized using the calculated primer pairs.

Figure 1:
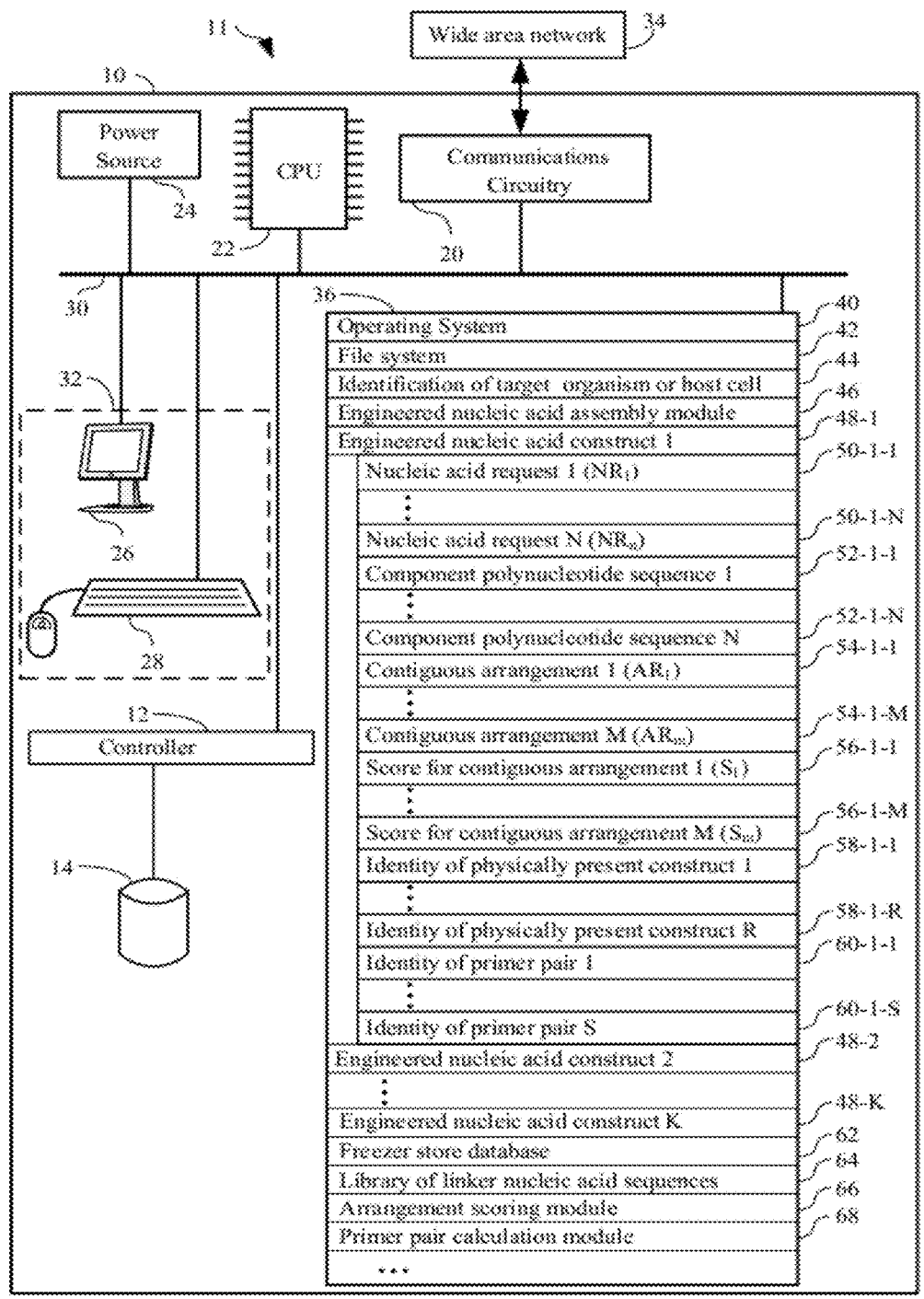

FIG. 1 details just such an exemplary system 11 for use in defining an engineered nucleic acid construct for integration into a genomic locus L of a target organism or a host cell. It will be appreciated that system 11 may be a scientific apparatus or a general purpose computer system. The system preferably comprises a computer system 10 having:

- a central processing unit 22;
- a main non-volatile (non-transitory) storage unit 14, for example a hard disk drive, for storing software and data, the storage unit 14 controlled by storage controller 12;
- a system memory 36, preferably high speed random-access memory (RAM), for storing system control programs, data, and application programs, comprising programs and data loaded from non-volatile storage unit 14; system memory 36 may also include read-only memory (ROM);
- a user interface 32, comprising one or more input devices (e.g., keyboard 28, a mouse) and a display 26 or other output device;
- optionally, a network interface card 20 (communications circuitry) for connecting to any wired or wireless communication network 34 (e.g., a wide area network such as the Internet);
- a power source 24 to power the aforementioned elements; and
- an internal bus 30 for interconnecting the aforementioned elements of the system.

Operation of computer 10 is controlled primarily by operating system 40, which is executed by central processing unit 22. Operating system 40 can be stored in system memory 36. In a typical implementation, system memory 36 also includes:

- a file system 42 for controlling access to the various files and data structures;
- an identification of a target organism or a host cell 44 into which an engineered nucleic acid construct will be integrated;
- an engineered nucleic acid assembly module 46 for assembling one or more engineered nucleic acid constructs in accordance with the present disclosure;
- the sequences of one or more engineered nucleic constructs 48 that have been constructed by engineered nucleic acid assembly module 46 in accordance with the present disclosure;
- a freezer store database 62 that details the source constructs that are physically present in a corresponding freezer store;
- a library of linker nucleic acid sequences 64 that are available for linking component nucleotides in accordance with an embodiment of the present disclosure;
- an arrangement scoring module 66 for scoring an arrangement of component nucleotides in accordance with the present disclosure; and
- a primer pair calculation module 68 for computing primer pairs in accordance with the present disclosure.

As illustrated in FIG. 1, computer 10 comprises data such as engineered nucleic acid constructs 48 as well as associated data for such constructs 48 (e.g., nucleic acid request 50, component polynucleotide sequences 52, scores for contiguous arrangements 56, identity of physically present constructs 58, and identity of primer pairs 60), freezer store database 62, and library of linker nucleic acid sequences 64.

Such data can be stored in any form of data storage system including, but not limited to, a flat file, a relational database (SQL), or an on-line analytical processing (OLAP) database (MDX and/or variants thereof). In some embodiments, engineered nucleic acid constructs 48 as well as associated data for such constructs 48, freezer store database 62, and library of linker nucleic acid sequences 64 is stored in a single database. In other embodiments, engineered nucleic acid constructs 48 as well as associated data for such constructs 48, freezer store database 62, and library of linker nucleic acid sequences 64 in fact are stored in a plurality of databases that may or may not all be hosted by the same computer 10. In such embodiments, some components of engineered nucleic acid constructs 48 as well as associated data for such constructs 48, freezer store database 62, and library of linker nucleic acid sequences 64 are stored on computer systems that are not illustrated by FIG. 1 but that are addressable by wide area network 34.

In some embodiments, computer 10 calculates engineered nucleic acid constructs 48 for at least two engineered nucleic acid constructs 48, at least three engineered nucleic acid constructs 48, at least four engineered nucleic acid constructs 48, at least five engineered nucleic acid constructs 48, at least fifteen engineered nucleic acid constructs 48, or at least fifty engineered nucleic acid constructs 48. In some embodiments, freezer store database 62 includes at least 2, at least 5, at least 8, at least 10, at least twenty-five, at least fifty, at least one hundred, at least two hundred, at least one thousand, at least five thousand, at least twenty-five thousand or at least 50 thousand different source constructs.

In some embodiments, engineered nucleic acid constructs 48 as well as associated data for such constructs 48, freezer store database 62, and library of linker nucleic acid sequences 64 and related software modules illustrated in FIG. 1 (e.g. engineered nucleic acid assembly module 46, arrangement scoring module 6, and primer pair calculation module 68) are on a single computer (e.g., computer 10) and in other embodiments they are hosted by several computers (not shown). In fact, all possible arrangements of engineered nucleic acid constructs 48 as well as associated data for such constructs 48, freezer store database 62, and library of linker nucleic acid sequences 64 and the modules illustrated in FIG. 1 on one or more computers are within the scope of the present disclosure so long as these components are addressable with respect to each other across computer network 34 or by other electronic means. Thus, the present disclosure fully encompasses a broad array of computer systems.

5.4 Exemplary Method for Polynucleotide Assembly—Multiple Arrangements

Methods for polynucleotide assembly are provided. Like the systems of Section 5.3, the methods disclosed in this section allow for the efficient construction of engineered nucleic acid constructs using the resources of a freezer store. More specifically, referring to FIG. 2, a method for defining an engineered nucleic acid construct for integration into a genomic locus L of a target organism or a host cell is disclosed. Exemplary target organisms include, but are not limited to, yeast, *E. coli*, or baculovirus.

Figure 2:
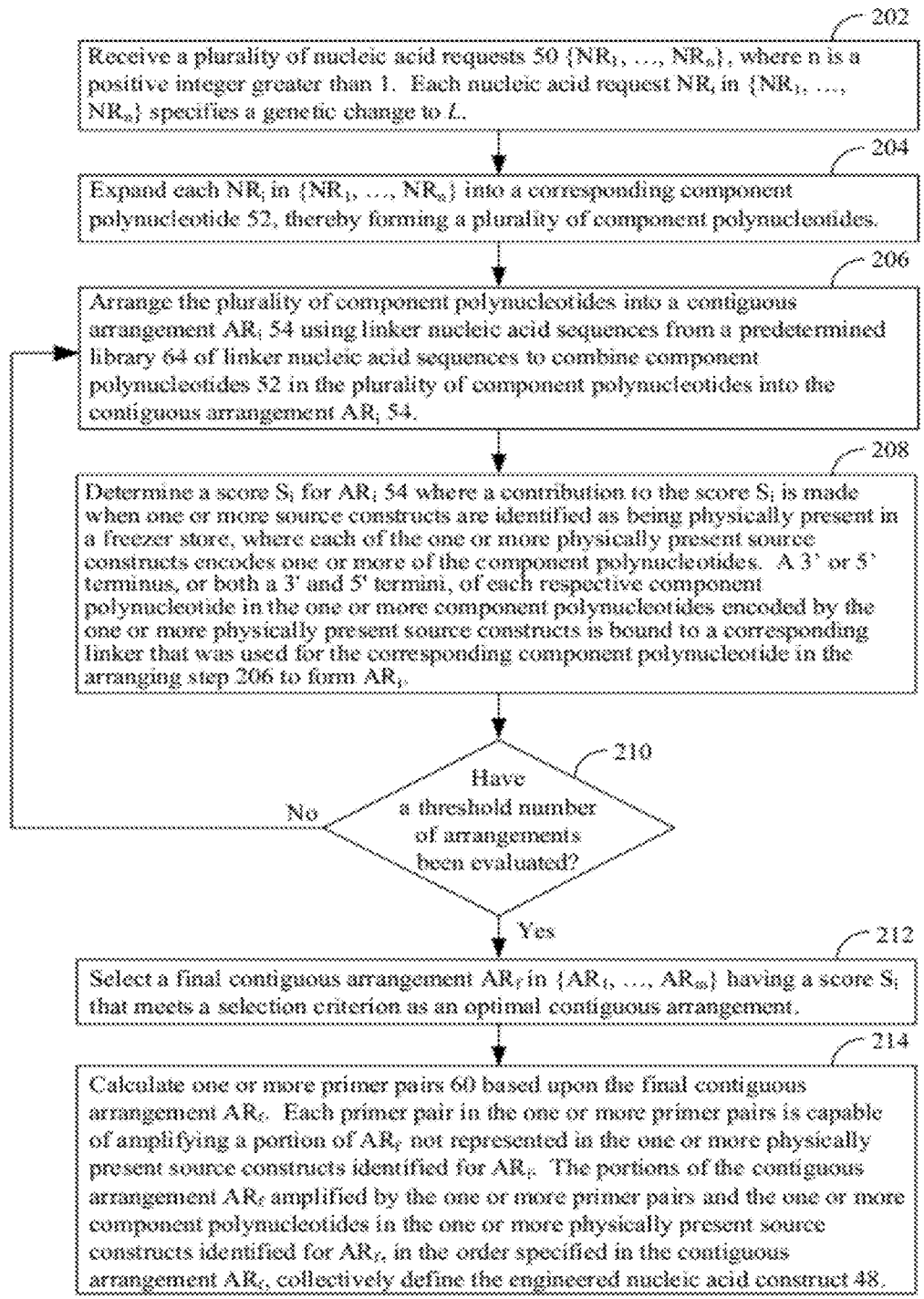

Certain of the steps are performed by various modules in memory 36. For example, in one embodiment, all the steps disclosed in FIG. 2 are directed by an engineered nucleic acid assembly module 46, with specific input for step 208 from an arrangement scoring module 66 and specific input for step 214 from a primer pair calculation module 68. However, it will be appreciated that the steps described in FIG. 2 can be encoded in a single module or any combination of modules.

Step 202.

Figure 3:
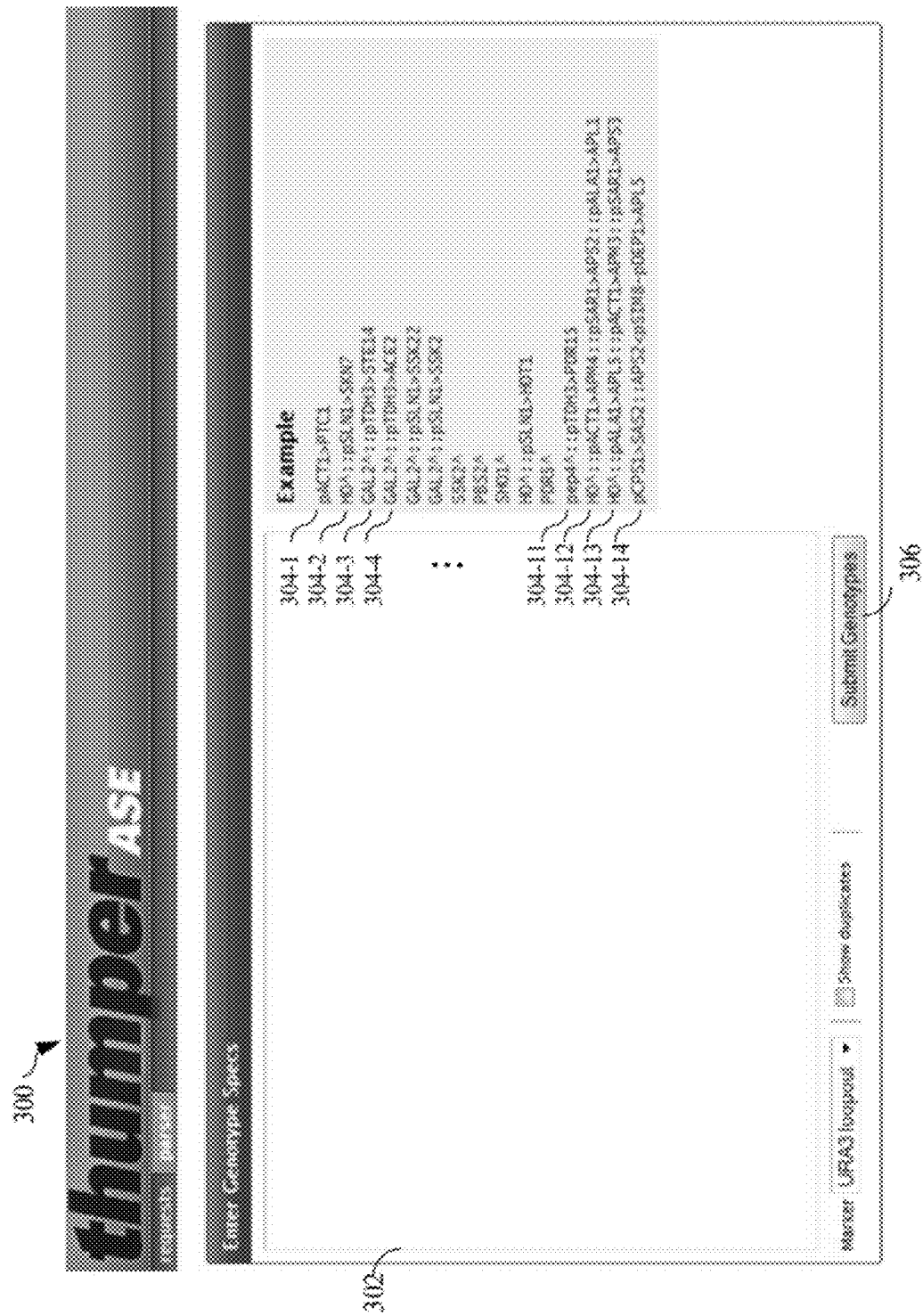

In step 202, a plurality of nucleic acid requests $\{NR_1, \ldots, NR_n\}$ are received, where n is a positive integer greater than 1. Each nucleic acid request $NR_i$ in $\{NR_1, \ldots, NR_n\}$ specifies a genetic change to locus L of a target organism or a host cell. In some embodiments, engineered nucleic acid assembly module 46 provides an input screen, such as input screen 302 for the input of $\{NR_1, \ldots, NR_n\}$. Examples of $\{NR_1, \ldots, NR_n\}$ are illustrated in FIG. 3. For example, the $\{NR_1, \ldots, NR_n\}$ "HO^::pSLN1>SKN7" for the target organism yeast specifies the insertion of an exogenous copy of SKN7 under the SLN1 promoter at the yeast HO locus.

Similarly, the $\{NR_1, \ldots, NR_n\}$ "GAL2^::pTDH3>STE14" for the target organism yeast specifies the insertion of an exogenous copy of STE14 under the pTDH3 promoter at the GAL2 locus and the $\{NR_1, \ldots, NR_n\}$ "GAL2^::pTDH3>ACE2" for the target organism yeast specifies the insertion of an exogenous copy of ACE2 under the pTDH3 promoter at the GAL2 locus.

The plurality of nucleic acid requests $\{NR_1, \ldots, NR_n\}$ may place more than one component polynucleotide at a locus. This is denoted herein by "::" to separate the elements. For example, "HO^::pSLN1>ADH1::pFBA1>ADH2" specifies that two different genes, ADH1 and ADH2, are placed at the HO locus under different promoters. In some embodiments, $\{NR_1, \ldots, NR_n\}$ specifies one or more genetic changes to locus L, two or more genetic changes to locus L, three or more genetic changes to locus L, four or more genetic changes to locus L, five or more genetic changes to locus L, between 5 and 10 genetic changes to locus L, between 5 and 40 changes to locus L, or more than 40 changes to locus L. In some embodiments, $\{NR_1, \ldots, NR_n\}$ specifies between 2 and 12 nucleic acid requests (change to locus L), between 2 and 100 nucleic acid requests, or more than 20 nucleic acid requests. However, regardless of the number of changes to locus L (nucleic acid requests) in $\{NR_1, \ldots, NR_n\}$, in typical embodiments, only one locus L is specified by the plurality of nucleic acid requests $\{NR_1, \ldots, NR_n\}$. That is, the genetic changes are directed to only one locus in the genome of the target organism. Multiple deletions, insertions, and other genetic changes disclosed herein can be requested at this one locus L, but only one locus is specified. This is because the end result of the exemplary methods provided herein are one or more engineered nucleic acid constructs that, in preferred embodiments, include insertion sequences for recombining with the target locus by homologous recombination.

A nucleic acid request $NR_i$ may specify an amino acid substitution. For instance, gGPR1$A640C specifies the GPR1 gene with an amino acid substitution at position 640 from alanine (A) to cysteine (C). A nucleic acid request $NR_i$ may specify a nucleic acid substitution. For example, gADH1*A200G specifies a point mutation at base pair 200 in the open reading frame, numbered from one, from an adenosine to a guanine. A nucleic acid request $NR_i$ may specify a slice of a desired gene part. This is denoted herein as "[ ]". The slice follows the gene name specification and specifies a "from" and "to" coordinate separated by a colon. For example gYNG2[1:660] requests the first 660 bases of the open reading frame of the YNG2 gene.

For convenience, a coordinate may be specified relative to the first or last base of the open reading frame. By default, everything is relative to the first base, but an 'S' or 'E' can be used to explicitly request and coordinate relative to the particular start or end. Relative to the start –1 is the first base preceding the open reading frame and negative coordinates in general specify upstream locations. Positive coordinates are downstream of the first base. Relative to the end, negative coordinates are upstream of the final base in the open reading frame (e.g. in the open reading frame and positive coordinates are downstream or in the three prime UTR). For example, gADH1[1:-4E] specifies the open reading frame of ADH1 omitting the final stop codon. gADH1[1E:200E] specifies the downstream 200 base pairs of the ADH1 gene, (e.g. its terminator sequence). gADH1-[-500:-1] or gADH1-[-500S:-1S] specify the promoter sequence.

For many designs, the precise end of a slice is less important than finding a point that will result in reliable construction, and so a coordinate may be preceded with a ~ to indicate an approximate preference. For example gADH1[~-500:-1] takes approximately 500 bases upstream of the ADH1 gene and the final decision for what constitutes the request $NR_i$ is based on an optimal construction decision e.g. avoiding low complexity DNA sequence.

The notation "!" can be used generally with any part to indicate that it should be inverted relative to its naturally occurring (locus) orientation. For example, the expression !gADH1; pGAL1; gADH2 specifies that the bidirectional gal1 yeast promoter is used to drive two genes one of which must point in the reverse direction relative to the other and the promoter.

In some embodiments, a nucleic acid request in the plurality of nucleic acid requests specifies insertion of an insertion sequence at L. In some such embodiments, the insertion sequence comprises a promoter and a gene the expression of which is driven by the promoter. In some such embodiments, the insertion sequence comprises a divergent promoter and a first gene and a second gene driven by the divergent promoter. In some embodiments, the divergent promoter is a back-to-back divergent promoter, an overlapping divergent promoter, or a face-to-face divergent promoter. In some embodiments, the insertion sequence comprises a promoter, a gene, a terminator, an open reading frame, a codon substitution, a nucleic acid substitution, a point mutation, an insertion mutation, or a deletion mutation. In some embodiments, the insertion sequence comprises a fusable open reading frame without a stop codon.

In some embodiments, the insertion sequence specifies a protein-coding sequence, a reporter gene, a fluorescent marker coding sequence, a promoter, an enhancer, a terminator, an intron, an exon, a poly-A tail, multiple cloning sites, a nuclear localization signal, an mRNA stabilization signal, a selectable marker, an integration loci, an epitope tag coding sequence, or a degradation signal. In some embodiments, the insertion sequence specifies a DNA segment of natural origin. Alternatively, the insertion sequence specifies a DNA segment that can be completely of synthetic origin, produced in vitro. Furthermore, an insertion sequence can comprise any combination of isolated naturally occurring DNA molecules, or any combination of an isolated naturally occurring DNA molecule and a synthetic DNA molecule. For example, an insertion sequence may comprise a heterologous promoter operably linked to a protein coding sequence, a protein coding sequence linked to a poly-A tail, a protein coding sequence linked in-frame with a epitope tag coding sequence, and the like.

In some embodiments, the nucleic acid request specifies that the entire genomic locus L is to be replaced by the insertion sequence. In some such embodiments, the nucleic acid request specifies that a promoter and a gene at L is to be replaced by the insertion sequence. In some such embodiments, the nucleic acid request specifies that a divergent promoter and a first gene and a second gene driven by the divergent promoter at L is to be replaced by the insertion sequence. In some such embodiments, the divergent promoter is a back-to-back divergent promoter, an overlapping divergent promoter, or a face-to-face divergent promoter. In some such embodiments, the nucleic acid request specifies that a promoter, a gene, a terminator, an open reading frame, a codon substitution, a nucleic acid substitution, a point mutation, an insertion mutation, or a deletion mutation at L is to be replaced by the insertion sequence. In some embodiments the nucleic acid request specifies that a fusible open reading frame without a stop codon is to be replaced by the insertion sequence. In some embodiments, the insertion sequence includes a first copy of a gene in a 3' to 5' orientation and a second copy of the gene in a 5' to 3' orientation, and a bi-directional promoter between the first copy and the second copy.

FIG. 3 illustrates that, in some embodiments, the plurality of nucleic acid requests $\{NR_1, \ldots, NR_n\}$ is in a data input construct. In some embodiments, the data input construct further comprises one or more pragmas to be used in performing the disclosed methods. In some embodiments, a pragma in the one or more pragmas specifies the identity of a predetermined library 64 of linker nucleic acid sequences that is to be used in the assembly of an engineered nucleic acid construct. In some embodiments, a pragma in the one or more pragmas specifies whether the engineered nucleic acid construct is to be (i) a single construct or, (ii) a two part construct comprising a first PCR product having a first part of a selectable marker and a second PCR product, having a second part of the selectable marker, wherein the first PCR product, running in the 5' to 3' direction, combines with the second PCR product, running in the 3' to 5' direction, to form the engineered nucleic acid construct with the selectable marker. In some embodiments, a pragma in the one or more pragmas specifies a selectable marker having a nucleic acid sequence to be incorporated into each contiguous arrangement $AR_i$ generated by the methods disclosed herein. In some embodiments, a pragma is between a first nucleic acid request and a second nucleic acid request in the data input construct, and the pragma specifies that a linker nucleic acid sequence not be placed between a first component polynucleotide specified by the first nucleic acid request and a second component polynucleotide specified by the second nucleic acid request in each contiguous arrangement $AR_i$ generated by the methods disclosed herein. Such a pragma is useful instances where, for example, no nucleic acid linker is desired between a promoter and the gene the promoter is intended to express. Thus, in one example, the first component polynucleotide comprises a promoter and the second component polynucleotide comprises a gene. In some embodiments, a pragma in the one or more pragmas specifies a reference genome to be used during expansion step 204, described below, to generate the corresponding component polynucleotide for a nucleic acid request in $\{NR_1, \ldots, NR_n\}$.

In some embodiments, an identity of a selectable marker is received with $\{NR_1, \ldots, NR_n\}$. This selectable marker is included in the engineered nucleic acid construct for purposes of validating successful integration of the engineered nucleic acid construct into the genome of the target organism or host cell. In some embodiments, a default selectable marker is used when no selectable marker is explicitly included in the received request that includes $\{NR_1, \ldots, NR_n\}$. In some embodiments, an identity of a selectable marker is determined without human intervention from a predetermined list of selectable markers when no selectable marker is explicitly included in the received request that includes $\{NR_1, \ldots, NR_n\}$. In some embodiments, where the received request does not include a selectable marker, the selectable marker is identified using any of the above-identified techniques during step 206 below.

Step 204.

In step 204, each $NR_i$ in $\{NR_1, \ldots, NR_n\}$ is expanded into a corresponding component polynucleotide, thereby forming a plurality of component polynucleotides. Expansion is necessary, for example, in instances where a ~ was used in an $NR_i$ to indicate an approximate preference. For example gADH1 [~-500:-1] takes approximately 500 bases upstream of the ADH1 gene and the final decision for what constitutes the request $NR_i$ is based on an optimal construction decision, e.g. avoiding low complexity DNA sequence. In step 204, such decisions are made as part of the expansion of the $NR_i$ to an actual polynucleotide sequence.

To illustrate expansion, consider the case of the plurality of nucleic acid requests $\{NR_1, \ldots, NR_n\}$: "HO^:: pSLN1>ADH1::pFBA1>ADH2" for the target organism yeast. Here, expansion step 204 expands the plurality of nucleic acid requests into component polynucleotides that allow for homologous recombination of pSLN1>ADH1::pFBA1>ADH2 into the HO locus. Thus, in this example, expansion step 204 expands HO^ into upstream and downstream integration sequences for homologous recombination with HO, pSLN1 into a component polynucleotide that encodes pSLN1, ADH1 into a component polynucleotide that encodes ADH1, pFBA1 into a component polynucleotide that encodes pFBA1, and ADH2 into a component polynucleotide that encodes ADH2.

In some embodiments, step 204 comprises expanding a first nucleic acid request in $\{NR_1, \ldots, NR_n\}$ into a first component polynucleotide and a second component polynucleotide, where the first component polynucleotide is a promoter and the second component polynucleotide is a gene. In various embodiments, the expansion from nucleic acid request in $\{NR_1, \ldots, NR_n\}$ to component polynucleotide is a one-to-one expansion, one-to-many expansion, or a many-to-one expansion. An example of a one-to-one expansion is the expansion of one nucleic acid request into a single corresponding component polynucleotide. An example of a one-to-many expansion is the breakdown of a single nucleic acid request into two or more component polynucleotides. An example of a many-to-one expansion is the taking one or more nucleic acid requests and encoding the requests in a single component polynucleotide.

In some embodiments, a nucleic acid request in $\{NR_1, \ldots, NR_n\}$ specifies a point mutation in a gene at genomic locus L and the expansion of this nucleic acid request in step 204 comprises obtaining a nucleic acid sequence of the gene and modifying the nucleic acid sequence of the gene to form a component polynucleotide in the plurality of component polynucleotides for $\{NR_1, \ldots, NR_n\}$.

In some embodiments, a nucleic acid request in $\{NR_1, \ldots, NR_n\}$ specifies that an exogenous gene is to be inserted at L and the expansion of this nucleic acid request comprises obtaining a sequence of the exogenous gene from a database of nucleic acid sequences to form a component polynucleotide in the plurality of component polynucleotides for $\{NR_1, \ldots, NR_n\}$.

In some embodiments, a nucleic acid request references a gene that is to be mutated, deleted from, or integrated in L and the expansion of step 204 comprises validating that the gene exists in an electronic gene database. In some embodiments, the expansion of step 204 comprises obtaining a nucleic acid segment specified by a nucleic acid request $NR_i$ in $\{NR_1, \ldots, NR_n\}$ from an electronic database of nucleic acid sequences and incorporating the nucleic acid segment into a component polynucleotide associated with the nucleic acid request $NR_i$. In some embodiments, the nucleic acid segment is a portion of a gene, a promoter, a terminator, or a gene.

In some embodiments, a nucleic acid request $NR_i$ specifies a nucleic acid segment having an approximate start point or an approximate end point and the expansion of step 204 defines an exact start point or an exact endpoint for the nucleic acid segment for incorporation into the component polynucleotide corresponding to $NR_i$ based on one or more endpoint selection criteria. In some embodiments, the endpoint selection criterion is avoiding low complexity DNA sequence or avoiding a restriction site.

In some embodiments, the expansion of step 204 comprises obtaining a nucleic acid segment specified by a nucleic acid request $NR_i$ in $\{NR_1, \ldots, NR_n\}$ and inverting the nucleic acid segment relative to a naturally occurring orientation of the nucleic acid segment prior to incorporation of the nucleic acid segment into a component polynucleotide associated with the nucleic acid request $NR_i$.

In some embodiments, a nucleic acid request $NR_i$ in $\{NR_1, \ldots, NR_n\}$ specifies an inline sequence to be incorporated into a nucleic acid sequence corresponding to $NR_i$ during step 204, and step 204 comprises inserting the inline sequence into the nucleic acid sequence corresponding to $NR_i$ thereby forming a component polynucleotide associated with $NR_i$.

In some embodiments, a nucleic acid request $NR_i$ in $\{NR_1, \ldots, NR_n\}$ specifies a nucleic acid segment within a gene that is to be rewritten with one or more synonymous codons before incorporation into a component polynucleotide corresponding to $NR_i$ during step 204, and step 204 comprises replacing the nucleic acid segment with the one or more synonymous codons.

In some embodiments, a nucleic acid request $NR_i$ in $\{NR_1, \ldots, NR_n\}$ specifies that a nucleic acid segment is to be rewritten with synonymous codons, before incorporation into a component polynucleotide corresponding to the nucleic acid request $NR_i$, so that the nucleic acid segment is maximally dissimilar relative to a naturally occurring instance of the nucleic acid segment and step 204 comprises rewriting the nucleic acid segment with synonymous codons so that the nucleic acid segment is maximally dissimilar relative to a naturally occurring instance of the nucleic acid segment and incorporating the rewritten nucleic acid segment in a component polynucleotide corresponding to the nucleic acid request $NR_i$.

In some embodiments, expanding step 204 comprises an iteration between (i) expansion of $\{NR_1, \ldots, NR_n\}$ to a parse tree and (ii) using the parse tree to rewrite $\{NR_1, \ldots, NR_n\}$ in simpler form, until no $NR_i$ in $\{NR_1, \ldots, NR_n\}$ can be rewritten in simpler form. Then, any of the above-identified expansion operations are performed on any of the $\{NR_1, \ldots, NR_n\}$ written out in simpler form. Parse trees and related compiler design principles are disclosed in *Modern Compiler Design*, Grune et al., John Wiley & Sons Ltd., New York, 2001, which is hereby incorporated by reference in its entirety.

Step 206.

In step 206, the plurality of component polynucleotides that were expanded from the plurality of nucleic acid requests are arranged into a contiguous arrangement $AR_i$. In typical embodiments, annealable linker nucleic acid sequences, from a predetermined library of annealable linker nucleic acid sequences 64, are used to combine the component polynucleotides corresponding to the plurality of nucleic acid requests $\{NR_1, \ldots, NR_n\}$ into the contiguous arrangement $AR_i$. In typical embodiments, such selection of linker nucleic acid sequences is limited to the design criterion that any given linker nucleic acid sequence in the library of linker nucleic acid sequences 64 only be used once in any given engineered nucleic acid construct. It will be appreciated that the predetermined library of annealable linker nucleic acid sequences 64 is a virtual library, not an actual library of nucleic acid sequences. Nevertheless, the virtual library contains predetermined annealable linker nucleic acid sequences that are designed to advantageously combine component polynucleotides into an engineered nucleic acid construct. In particular, such annealable linker nucleic acid sequences provide the component polynucleotides with complementary termini that are utilized in a splice overlap extension assembly reaction followed by polymerase chain reaction to assemble the component polynucleotides into an assembled polynucleotide with an ordered sequence. The general properties of such annealable linker nucleic acid sequences are disclosed in section 5.14 below.

In some embodiments, consistent with the properties of annealable linker nucleic acid sequences disclosed in section 5.14 below, the predetermined library of linkers 64 has a structure illustrated in FIG. 7. The exemplary library of linkers 64 includes categories 702 of linkers. An example of one such category 702 is high G-C content. Annealable linker nucleic acid sequences in this category have a high G-C content, i.e., the number of guanine and cytosine nucleotides in the annealable linker nucleic acid sequence as a percentage of the total number of bases in the annealable linker nucleic acid sequence. Annealable linker nucleic acid sequences that have a high G-C content are generally useful in the methods of the invention because a high G-C content generally provides for a high $T_m$, which in turn may provide for more specific priming during an assembly reaction and for time and process savings by allowing combination of the annealing and extension steps of SOE/PCR. This category of annealable linker nucleic acid sequences is disclosed in more detail in section 5.14 below.

Another exemplary category 702 of annealable linker nucleic acid sequences is high A-T content. Annealable linker nucleic acid sequences in this category have a high A-T content, i.e., the number of adenine and thymine nucleotides in the annealable linker nucleic acid sequence as a percentage of the total number of bases in the annealable linker nucleic acid sequence. A high A-T content may provide for reduced propensity of the annealable linker nucleic acid sequence to form substantial secondary structures, which may be of particular concern when the annealable linker nucleic acid sequence is used to assemble component polynucleotides comprising a promoter and a protein coding sequence into a assembled polynucleotide in which the annealable linker nucleic acid sequence is positioned between the promoter and the protein coding sequence. This category of annealable linker nucleic acid sequences is disclosed in more detail in section 5.14 below.

For each category 702 of annealable linker nucleic acid sequence, there is a set of 3' linkers (LA linkers) and a corresponding set of 5' linkers (LB linkers). The 5' linkers (LA) are designed for the 5' end of a component polynucleotide where the 3' linkers (LB) are designed for the 3' end of a component polynucleotide. Each linker is assigned a number. For instance, referring to FIG. 7, category 702-1 includes the 702-1-A set of 5' linkers $\{704\text{-}1\text{-}LA_1, 704\text{-}1\text{-}LA_2, \ldots, 704\text{-}1\text{-}LA_n\}$ and the 702-1-B set of 3' linkers $\{704\text{-}1\text{-}LB_1, 704\text{-}1\text{-}LB_2, \ldots, 704\text{-}1\text{-}LB_n\}$, category 702-2 includes the 702-2-A set of 5' linkers $\{704\text{-}2\text{-}LA_1, 704\text{-}2\text{-}LA_2, \ldots, 704\text{-}2\text{-}LA_m\}$ and the 702-2-B set of 3' linkers $\{704\text{-}2\text{-}LB_1, 704\text{-}2\text{-}LB_2, \ldots, 704\text{-}2\text{-}LB_m\}$, and so forth.

Referring to FIG. 7, in some embodiments, the library of linker nucleic acid sequences 64 has one category. In some embodiments, the library of linker nucleic acid sequences 64 has two categories, (e.g., A-T rich and G-C rich). In some embodiments, the library of linker nucleic acid sequences 64 has three categories. In some embodiments, the library of linker nucleic acid sequences 64 has four or more categories, five or more categories, six or more categories, ten or more categories, or one hundred or more categories. In some embodiments, there are one or more, two or more, three or more, four or more, five or more, ten or more, or twenty or more 5' LA linkers 704 in a given category 702. In some embodiments, there are one or more, two or more, three or more, four or more, five or more, ten or more, or twenty or more 5' LB linkers 704 in a given category 702. In some embodiments, there is the same number of 5' LA linkers 704 as 5' LB linkers 704 in any given category 702 in the library of linker nucleic acid sequences 64.

In some embodiments, the library 64 of linker nucleic acid sequences consists of 100 linker nucleic acid sequences 704 or less. In some embodiments, the predetermined library of linker nucleic acid sequences consists of 50 linker nucleic acid sequences 704 or less. In some embodiments, the predetermined library of linker nucleic acid sequences consists of 20 linker nucleic acid sequences 704 or less. In some embodiments, the library 64 of linker nucleic acid sequences consists of 100 linker nucleic acid sequences 704 or less per category 702. In some embodiments, the predetermined library of linker nucleic acid sequences consists of 50 linker nucleic acid sequences 704 or less per category 702. In some embodiments, the predetermined library of linker nucleic acid sequences consists of 20 linker nucleic acid sequences 704 or less per category 702.

Advantageously, in some embodiments, for a given category 702-X, each linker 704-X-$LB_i$, upon denaturation to single stranded form, is capable of hybridizing to the complement of 704-X-$LA_{i+1}$. For instance, in such embodiments, 704-1-$LB_1$ is capable of hybridizing to the complement of 704-1-$LA_2$, 704-2-$LB_1$ is capable of hybridizing to the complement of 704-2-$LA_2$, and so forth.

In alternative embodiments, for a given category 702-X, each linker 704-X-$LB_i$, upon denaturation to single stranded form, is capable of hybridizing to the complement of 704-X-$LA_{i-1}$. For instance, in such embodiments, 704-1-$LB_2$ is capable of hybridizing to the complement of 704-1-$LA_1$, 704-2-$LB_2$ is capable of hybridizing to the complement of 704-2-$LA_1$, and so forth. For ease of reference herein, the embodiment in which, for a given category 702-X, each linker 704-X-$LB_i$, upon denaturation to single stranded form, is capable of hybridizing to the complement of 704-X-$LA_{i+1}$ will be presented. Those of skill in the art will appreciate that in any such example, there exists a corresponding example based upon the principle that for a given category 702-X, each linker 704-X-$LB_i$, upon denaturation to single stranded form, is capable of hybridizing to the complement of 704-X-$LA_{i-1}$. Such alternative examples and embodiments are within the scope of the present disclosure.

Consider the case where an arrangement $AR_i$ specifies that component polynucleotides CN1 and CN2 are to be contiguously linked together such that CN1 is directly upstream of CN1 and CN2 is a promoter for CN2. Because CN1 is a promoter for CN2, a category 702-1 of linker nucleic acid sequences is chosen for the 3' end of CN1 and the 5' end of CN2. To satisfy other design constraints, category 702-2 of linker nucleic acid sequences is chosen for the 5' end of CN1 and the 3' end of CN2. One of the many arrangements that would satisfy these design criteria is:

5'-(704-2-$LA_1$)-CN1-(704-1-$LB_1$)-3', '-(704-1-$LA_2$)-CN2-(704-2-$LB_2$)-3' because 704-1-$LB_1$ is capable of hybridizing to the complement of 704-1-$LA_2$ to form the construct:

5'-(704-2-$LA_1$)-CN1-(704-1-$LB_1$)-CN2-(704-2-$LB_2$)-3'.

More generally, in the instance where there is only a single category 702 of annealable linker nucleic acid sequences, the contiguous arrangement $AR_i$ comprises, in a 5' to 3' orientation, A=an ordered set $\{X_1, \ldots, X_t\}$, where, t is a positive integer greater than 1, each i is an integer in the set of integers $\{1, \ldots, t\}$, each $X_i$ comprises 5'-$LA_i$-$NA_i$-$LB_i$-3', each $LB_i$ is a linker nucleic acid sequence in the predetermined library 64 of linker nucleic acid sequences, each $NA_i$ is a component polynucleotide in the plurality of component polynucleotides, each $LB_i$, for i less than t, upon denaturation to single stranded form, is capable of hybridizing to the complement of $LA_{i+1}$, thereby forming the nucleic acid sequence:

5'-$LA_1$-$NA_1$, ..., $LB_{n-1}$-$NA_n$-$LB_n$-3'.

The more complex embodiment in which there are multiple categories of linker nucleic acid sequences used in an arrangement merely alters the requirement that each $LB_i$, for i less than t, upon denaturation to single stranded form, is capable of hybridizing to the complement of $LA_{i+1}$ to specify that each $LB_i$ of a respective category 702, for i less than t, upon denaturation to single stranded form, is capable of hybridizing to the complement of $LA_{i+1}$ in the same respective category 702. Such annealable linker nucleic acid sequences, and their ability to assemble the component polynucleotides into an assembled polynucleotide with the specified ordered sequence by a splice overlap extension assembly reaction followed by polymerase chain reaction (SOE/PCR), as disclosed in U.S. patent application Ser. No. 12/622,401 (Pub. No. 2010/0136633 A1), filed Nov. 19, 2009, which is hereby incorporated by reference in its entirety as well as section 5.14, below. Such assembly methods can be used to assemble any number of component polynucleotides into one or more assembled polynucleotides. In some embodiments, the methods provided herein result in the assembly of 2, 3, 4, 5, 6, 7, 8, 9, 10, 11, 12, 13, 14, 15, or more component polynucleotides into one or more assembled polynucleotides.

In some embodiments, the contiguous arrangement $AR_i$ comprises:

A=an ordered set $\{X_1, \ldots, X_t\}$,

B=$NA_0$-$LB_0$, and

C=$LA_{t+1}$-$NA_{t+1}$, where, t is a positive integer greater than 1, each i is an integer in the set of integers $\{1, \ldots, t\}$, each $X_i$ comprises 5'-$LA_i$-$NA_i$-$LB_i$-3', each $LB_i$ is a linker nucleic acid sequence in the predetermined library 64 of linker nucleic acid sequences, each $NA_i$ is a component polynucleotide in the plurality of component polynucleotides identified in step 204, each $LB_i$, for i less than t, upon denaturation to single stranded form, is capable of hybridizing to the complement of $LA_{i+1}$, thereby forming the nucleic acid sequence:

5'-$LA_1$-$NA_1$, ..., $LB_{N-1}$-$NA_N$-$LB_N$-3', $LB_0$ is a linker nucleic acid sequence in the predetermined library of linker nucleic acid sequences, $NA_0$ and $NA_{t+1}$ are each component polynucleotides in the plurality of component polynucleotides, the contiguous arrangement $AR_i$ comprising, in a 5' to 3' orientation, A, B, C, and where, $LB_0$, upon denaturation to single stranded form, is capable of hybridizing to the complement of $LA_1$, and $LB_t$, upon denaturation to single stranded form, is capable of hybridizing to the complement of $LA_{t+1}$, so that the nucleic acid construct comprises the nucleic acid sequence:

5'-$NA_0$-$LB_0$, . . . , $LB_{t-1}$-$NA_t$-$LB_t$-$NA_{t+1}$-3'.

In some embodiments, upon denaturation of $X_i$ in A, each $LB_i$, for i less than t, is capable of selectively hybridizing to the complement of $LA_{i+1}$ compared to each other linker nucleic acid sequence $LA_y$ or $LB_y$, or their complements, in A, where each y is an integer, other than i, in the set of integers $\{1, \ldots, t\}$. In some embodiments, an $LA_i$ or an $LB_i$ of an $X_i$ in A is at least 24 nucleotides in length and has a melting temperature of at least 60° C.

In some embodiments, a contiguous arrangement $AR_i$ comprises, in a 5' to 3' orientation, D=an ordered set $\{Q_1, \ldots, Q_a\}$ where, a is a positive integer greater than 1, each i is an integer in the set of integers $\{1, \ldots, a\}$, each $Q_i$ comprises 5'-$RA_i$-$LA_i$-$NA_i$-$LB_i$-$RB_i$-3', each $LB_i$ is a linker nucleic acid sequence from the predetermined library of linker nucleic acid sequences, each $NA_i$ is a component polynucleotide in the plurality of component polynucleotides, and each $LB_i$, for i less than a, upon denaturation to single stranded form and upon cleavage of each restriction site $RA_i$ and $RB_i$, is capable of hybridizing to the complement of $LA_{i+1}$, thereby forming the engineered nucleic acid construct comprising the nucleic acid sequence:

5'-$LA_1$-$NA_1$, . . . , $LB_{a-1}$-$NA_a$-$LB_a$-3'.

In some embodiments, a contiguous arrangement $AR_i$ in the set of $\{AR_1, \ldots, AR_m\}$ contiguous arrangements comprises, in a 5' to 3' orientation, D=an ordered set $\{Q_1, \ldots, Q_a\}$, E=$RA_0$-$NA_0$-$LB_0$-$RB_0$, and F=$RA_{a+1}$-$LA_{a+1}$-$NA_{a+1}$-$RB_{a+1}$, where, a is a positive integer greater than 1, each i is an integer in the set of integers $\{1, \ldots, a\}$, each $Q_i$ comprises 5'-$RA_i$-$LA_i$-$NA_i$-$LB_i$-$RB_i$-3', each $LB_i$ is a linker nucleic acid sequence from the predetermined library of linker nucleic acid sequences, each $NA_i$ is a component polynucleotide in the plurality of component polynucleotides, and each $LB_i$, for i less than a, upon denaturation to single stranded form and upon cleavage of each restriction site $RA_i$ and $RB_i$, is capable of hybridizing to the complement of $LA_{i+1}$, thereby forming the engineered nucleic acid construct comprising the nucleic acid sequence:

5'-$LA_1$-$NA_1$, . . . , $LB_{a-1}$-$NA_a$-$LB_a$-3', $LB_0$ is a linker nucleic acid sequence from the predetermined library of linker nucleic acid sequences, restriction sites $RA_0$, $RB_0$, $RA_{a+1}$ and $RB_{a+1}$ are each independently cleavable by one or more type IIS restriction endonucleases, restriction sites $RA_0$ and $RB_0$ are oriented so that cleavage of $RA_0$ and $RB_0$ separates their respective recognition and cleavage sites from the resulting nucleic acid molecule that comprises $NA_0$-$LB_0$, restriction sites $RA_{a+1}$ and $RB_{a+1}$ are oriented so that cleavage of $RA_{a+1}$ and $RB_{a+1}$ separates their respective recognition and cleavage sites from the resulting nucleic acid molecule that comprises $NA_{a+1}$-$LB_{a+1}$, and $NA_0$ and $NA_{a+1}$ are each component polynucleotides in the plurality of component polynucleotides, the contiguous arrangement $AR_i$ comprising, in a 5' to 3' orientation, D, E, F, and where $LB_0$, upon denaturation to single stranded form and upon cleavage of $RB_0$, is capable of hybridizing to the complement of $LA_1$, and $LB_n$, upon denaturation to single stranded form and upon cleavage of $RB_a$, is capable of hybridizing to the complement of $LA_{a+1}$, so that the nucleic acid construct comprises the nucleic acid sequence:

5'-$NA_0$-$LB_0$, . . . , $LB_{a-1}$-$NA_a$-$LB_a$-$NA_{a+1}$-3'.

In some embodiments, upon denaturation of $Q_i$ in D and upon cleavage of each restriction site $RA_i$ and $RB_i$ in D, each $LB_i$, for i less than a, is capable of selectively hybridizing to the complement of $LA_{i+1}$ compared to each of the other linker nucleic acid sequences $LA_y$ or $LB_y$, or their complements, in D, wherein each y is an integer, other than i, in the set of integers $\{1, \ldots, a\}$. In some embodiments an $LA_i$ or an $LB_i$ in a $Q_i$ in D is at least 24 nucleotides in length and has a melting temperature of at least 60° C. In some embodiments each $RA_i$ and each $RB_i$ in Q is cleavable by SapI or LguI restriction endonuclease. In some embodiments, each restriction site $RA_i$ and each restriction site $RB_i$ is independently cleavable by one or more type IIS restriction endonucleases, where each of restriction site $RA_i$ and each restriction site $RB_i$ is oriented so that cleavage of a respective restriction site $RA_i$ and a respective restriction site $RB_i$ separates their recognition and cleavage sites from the resulting nucleic acid molecule $LA_i$-$NA_i$-$LB_i$.

It will be appreciated that, in many instances, the actual order of the component polynucleotides is not important. For instance, unless otherwise specified by a requesting molecular biologist, the nucleic acid requests:

HO^::pFBA1>ADH2::pSLN1>ADH1, and

HO^::pSLN1>ADH1::pFBA1>ADH2 are equivalent in that, in either case, pFBA>ADH2 and pSLN1>ADH1 are inserted at the HO locus. As this example demonstrates, any of several different linker 704 pairs from the library of linker nucleic acid sequence 64 can be used to form a valid arrangement of HO^::pFBA1>ADH2:: pSLN1>ADH1. To illustrate, expansion of HO^:: pFBA1>ADH2:: pSLN1>ADH1 at step 204 results in the component polynucleotides: 5'-HO insertion sequence, pFBA1, ADH2, pSLN1, ADH1, and the 3-HO insertion sequence. One valid arrangement of these component polynucleotides would order pFBA1>ADH2 before pSLN1>ADH1 and another valid arrangement would order pSLN1>ADH1 before pFBA1>ADH2. Focusing on the former exemplary arrangement pFBA1>ADH2 before pSLN1>ADH1, step 206 could use linker nucleic acid sequences from the library of nucleic acid sequence 64 to specify 5'-$LA_1$-pFBA1-$LB_1$-3',5'-$LA_2$-ADH2-$LB_2$-3',5'-$LA_3$-pSLN1-$LB_3$-3',5'-$LA_4$-ADH1-$LB_4$-3', where the HO insertion sequences are not considered in the example. For ease of disclosure and understanding, the assumption is made in this example that the library of linker nucleic acid sequences 64 either has a single category 702 or that all the linkers used in the exemplary arrangement are of the same category 702 so that the more simple notation $LA_x$, $LB_x$ may be used to denote the linkers rather than the more complex notation 704-X-$LA_m$, 704-X-$LB_m$. Thus, in this example, the respective complementary termini $LB_1$, $LA_{n+1}$ are utilized in a splice overlap extension assembly reaction followed by polymerase chain reaction (SOE/PCR) to assemble the component polynucleotides, with linkers not added, into an engineered nucleic acid with an ordered sequence 5'-LA$_1$-pFBA1-LB$_1$-ADH2-LB$_2$-pSLN1-LB$_3$-ADH1-LB$_4$-3'.

Alternatively, in the other valid arrangement, pSLN1>ADH1 precedes pFBA1>ADH2, and step 206 uses the linker nucleic acid sequences from the library of nucleic acid sequence 64 to define 5'-LA$_1$-pSLN1-LB$_1$-3',5'-LA$_2$-ADH1-LB$_2$-3',5'-LA$_3$-pFBA1-LB$_3$-3',5'-LA$_4$-ADH2-LB$_4$-3'. In this alternative, the respective complementary termini LB$_1$, LA$_{n+1}$ are utilized in a splice overlap extension assembly reaction followed by polymerase chain reaction (SOE/PCR) to assemble the component polynucleotides into an engineered nucleic acid with an ordered sequence 5'-LA$_1$-pSLN1-LB$_1$-ADH1-LB$_2$-pFBA$_1$-LB$_3$-ADH2-LB$_4$-3'. It will be appreciated that the first and last component polynucleotides in the arrangement may also include linkers so that they anneal with the HO insertion sequences. Thus, the above example is given merely to depict how several different valid arrangements may arise rather than to provide a complete sequence of an engineered nucleic acid with all attendant linkers.

While only two valid arrangements are provided in the example above, the number of valid arrangements that will achieve the specifications of the plurality of nucleic acid requests received in step 202 can be extensive, particularly when there are a number of component polynucleotides that need not be placed in a particular order. The number of permutations of n distinct component polynucleotides, whose order does not matter is n*(n−1)*(n−2)* . . . *2*1, which number is called "n factorial" and written "n!". Thus, consider an example in which an arrangement has 15 component nucleotides, for which 5 of the component nucleotides can be arranged in any order. In this case, there would be 5*(5−1)*(5−2)*2*1=120 different possible arrangements of the component nucleotides, each of which would validly accomplish the plurality of nucleic acid requests received in step 202. As this example demonstrates, in some embodiments, there are 2 or more, 3 or more, 4 or more, 10 or more, 1000 or more or even 10,000 possible valid arrangements of the component polynucleotides that encode the plurality of nucleic acid requests.

One example where component nucleotides can be arranged in any order arises when several different genes are to be inserted into a given locus, each under a different promoter. Typically, the order of such genes is not important as long as each respective inserted gene is driven by the promoter requested for the respective gene. Moreover, in typical embodiments, a selectable marker is added to an engineered construct to facilitate identification of clones that contain the engineered construct. The location of this selectable marker typically does not matter so long as it does not interrupt the relationship between a gene and its regulatory elements (e.g., promoter, terminator, enhancer, etc.). Where such a selectable marker is used, 5' and 3' linkers from the library of linker nucleic acid sequences are added to the ends of the selectable marker as was the case for the component polynucleotides of step 204.

In some embodiments a first component polynucleotide is identical to a second component polynucleotide in the plurality of component polynucleotides from expansion step 204. In such embodiments, a contiguous arrangement that would cause the first component polynucleotide and the second component polynucleotide to run in the same direction in the engineered nucleic acid construct is barred. This is accomplished by running one of the two polynucleotides in the 5' to 3' direction and the other of the two polynucleotides in the 3' to 5' direction in the engineered nucleic acid construct.

In some embodiments a first component polynucleotide has a high degree of sequence similarity to a second component polynucleotide in the plurality of component polynucleotides from expansion step 204. For example, the first component polynucleotide can be at least 70%, 75%, 80%, 85%, 90% or 95% identical to the second component polynucleotide. In some embodiments, the first component polynucleotide comprises at least 100 contiguous nucleotides having at least 70%, 75%, 80%, 85%, 90% or 95% identity to the second polynucleotide. In such embodiments, a contiguous arrangement that would cause the first component polynucleotide and the second component polynucleotide to run in the same direction in the engineered nucleic acid construct is barred. This is accomplished by running one of the two polynucleotides in the 5' to 3' direction and the other of the two polynucleotides in the 3' to 5' direction in the engineered nucleic acid construct.

In some embodiments, the arranging of step 206 comprises inserting a selectable marker having a nucleic acid sequence into a contiguous arrangement AR$_i$. In some such embodiments, the engineered nucleic acid construct comprises a first PCR product having a first part of the selectable marker and a second PCR product, having a second part of the selectable marker, where the first PCR product, running in the 5' to 3' direction, combines with the second PCR product, running in the 3' to 5' direction, to form the engineered nucleic acid construct with the selectable marker. Advantageous methods for such constructs are disclosed in are disclosed in U.S. patent application Ser. No. 12/622,401 (Pub. No. 2010/0136633 A1), filed Nov. 19, 2009, which is hereby incorporated by reference in its entirety.

Step 208.

In step 208, a score S$_i$ is determined for AR$_i$. To accomplish this, a query of a freezer store database 62 is made to determine whether a corresponding freezer store includes all or a portion of AR$_i$. For example, consider the example in which the plurality of nucleic acid requests is HO^::pFBA1>ADH2::pSLN1>ADH1 and the arrangement generated in step 206 comprises the component polynucleotides 5'-LA$_1$-pFBA1-LB$_1$-3',5'-LA$_2$-ADH2-LB$_2$-3',5'-LA$_3$-pSLN1-LB$_3$-3',5'-LA$_4$-ADH1-LB$_4$-3', where each LB$_i$, upon denaturation to single stranded form, is capable of hybridizing to the complement of LA$_{i+1}$, and where HO insertion sequences are not considered solely to simplify the example. A query is made of the freezer store database 62 to determine whether any of the component polynucleotides are present as source constructs.

Figure 6A:
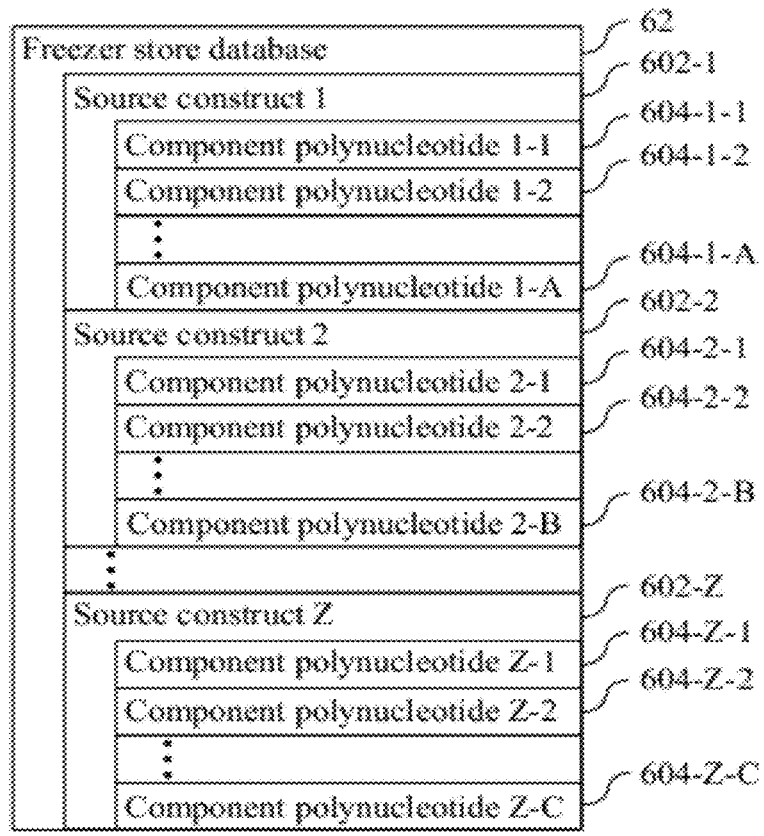
FIG. 6A illustrates an exemplary freezer store database detailing source constructs that are physically present in a corresponding freezer store and, for each such source construct, the component polynucleotide (inserts) within the source construct in accordance with an embodiment of the present disclosure.
Figure 6B:
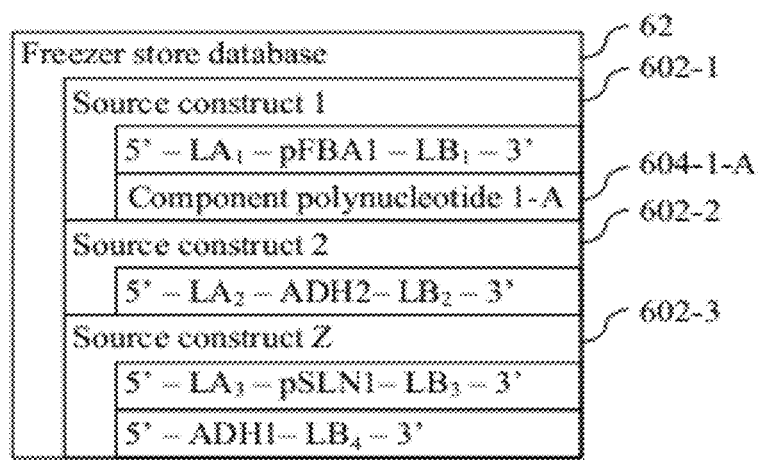
FIG. 6B illustrates another exemplary freezer store database detailing source constructs that are physically present in a corresponding freezer store and, for each such source construct, the component polynucleotide (inserts) within the source construct in accordance with an embodiment of the present disclosure.

An exemplary illustration of the architecture of a freezer store database 62 is provided in FIG. 6A. Freezer store database 62 comprises information about a plurality of source constructs 602. Each source construct 602 comprises one or more component polynucleotides 604. In typical embodiments, each source construct 602 is in circular vector form. An exemplary embodiment of a source construct 602 is an assembly vector. Assembly vectors are described in Section 5.13, below.

In typical embodiments, each respective source construct 602 in the freezer store indexed by freezer store database 62 contains a selectable marker and this selectable marker must match the selectable marker that has been selected for the engineered nucleic acid construct in order for the component polynucleotides within the respective source construct to be evaluated against the component polynucleotides of the AR$_i$.

In typical embodiments, a 3' or 5' terminus, or both the 3' and 5' termini, of each respective component polynucleotide 604 in the one or more component polynucleotides encoded by the one or more physically present source constructs 602 is bound to a corresponding linker in the library of linker nucleic acid sequences 64.

In some embodiments, a component polynucleotide 604 in a source construct 602 is considered a match to a component polynucleotide in $AR_i$ when (i) the sequence of the component polynucleotide 604 matches the sequence of the component polynucleotide in $AR_i$, (ii) a 3' or 5' terminus of the component polynucleotide 604 is bound to a linker that was used for the respective component polynucleotide in step 206 to form $AR_i$, and (iii) the selectable marker for the source construct 602 that contains the component polynucleotide 604 is the same selectable marker that is specified for the engineered nucleic acid construct.

In some embodiments, a component polynucleotide 604 in a source construct 602 is considered a match to a component polynucleotide in $AR_i$ when (i) the sequence of the component polynucleotide 604 matches the sequence of the component polynucleotide in $AR_i$, (ii) the 3' terminus of the component polynucleotide 604 is bound to a linker that was used for the 3' terminus of the respective component polynucleotide in step 206 to form $AR_i$, (iii) the 5' terminus of the component polynucleotide 604 is bound to a linker that was used for the 5' terminus of the respective component polynucleotide in step 206 to form $AR_i$, and (iv) the selectable marker for the source construct 602 that contains the component polynucleotide 604 is the same selectable marker that is specified for the engineered nucleic acid construct.

In some embodiments, a component polynucleotide 604 in a source construct 602 is considered a match to a component polynucleotide in $AR_i$ when (i) the sequence of the component polynucleotide 604 matches the sequence of the component polynucleotide in $AR_i$ and (ii) a 3' or 5' terminus of the component polynucleotide 604 is bound to a linker that was used for the respective component polynucleotide in step 206 to form $AR_i$.

In some embodiments, a component polynucleotide 604 in a source construct 602 is considered a match to a component polynucleotide in $AR_i$ when (i) the sequence of the component polynucleotide 604 matches the sequence of the component polynucleotide in $AR_i$, (ii) a 3' or 5' terminus of the component polynucleotide 604 is bound to a linker that was used for the respective component polynucleotide in step 206 to form $AR_i$, (iii) the selectable marker for the source construct 602 that contains the component polynucleotide 604 is the same selectable marker that is specified for the engineered nucleic acid construct, and (iv) the orientation (5' to 3' or 3' to 5') of the component polynucleotide 604 in the source construct 602 matches the orientation of the component polynucleotide in $AR_i$.

In some embodiments, a component polynucleotide 604 in a source construct 602 is considered a match to a component polynucleotide in $AR_i$ when (i) the sequence of the component polynucleotide 604 matches the sequence of the component polynucleotide in $AR_i$, (ii) the 3' terminus of the component polynucleotide 604 is bound to a linker that was used for the 3' terminus of the respective component polynucleotide in step 206 to form $AR_i$, (iii) the 5' terminus of the component polynucleotide 604 is bound to a linker that was used for the 5' terminus of the respective component polynucleotide in step 206 to form $AR_i$, (iv) the selectable marker for the source construct 602 that contains the component polynucleotide 604 is the same selectable marker that is specified for the engineered nucleic acid construct, and (v) the orientation (5' to 3' or 3' to 5') of the component polynucleotide 604 in the source construct 602 matches the orientation of the component polynucleotide in $AR_i$.

In some embodiments, a component polynucleotide 604 in a source construct 602 is considered a match to a component polynucleotide in $AR_i$ when (i) the sequence of the component polynucleotide 604 matches the sequence of the component polynucleotide in $AR_i$, (ii) a 3' or 5' terminus of the component polynucleotide 604 is bound to a linker that was used for the respective component polynucleotide in step 206 to form $AR_i$, and (iii) the orientation (5' to 3' or 3' to 5') of the component polynucleotide 604 in the source construct 602 matches the orientation of the component polynucleotide in $AR_i$.

Thus, in typical embodiments, information beyond that which is illustrated in FIG. 6A is stored for each source construct 602. In some embodiments, the selectable marker of each source construct 602 is stored in the freezer store database 62. In some embodiments, the 5' and 3' linker of each component polynucleotide 604 is stored in freezer store database 62. In some embodiments, the full nucleic acid sequence of each component polynucleotide 604 and any attached linkers is stored in freezer store database 62. In some embodiments the quantity of each source construct 602 existing in the freezer store is stored in the freezer store database 62.

FIG. 8 provides a snapshot of representative source constructs 602 and the information that is stored for each source construct 602 in an exemplary embodiment. In the exemplary embodiment, freezer store database 62 includes a unique identifier 802 and a name 804 for each source construct 602. For each source construct 602 in this exemplary embodiment, freezer store database 62 also includes an identity 806 of a linker, from the library of linker nucleic acid sequences 64, that is used for the source construct insert. For each source construct 602 in this exemplary embodiment, freezer store database 62 also includes the direction (5' to 3' or 3' to 5') of the source construct insert. For each source construct 602 in this exemplary embodiment, freezer store database 62 includes the breed 810 (e.g., GST) and the source 812 (e.g., *S. cerevisiae, E. coli*, etc.) of the source construct 602. For each source construct 602 in this exemplary embodiment, freezer store database 62 includes a name of the insert 812 (component polynucleotide) and a status (e.g., available, requested) 818 of the source construct 602. For each source construct 602 in this exemplary embodiment, freezer store database 62 includes an available concentration 820 of the source construct 602 in the associated freezer store. For each source construct 602 in this exemplary embodiment, freezer store database 62 optionally includes a popularity of the source construct, for instance, represented by positive and/or negative votes 822 by users of the source construct 602.

Each of the source constructs 602 indexed by freezer store database 62 is physically present in a collection of freezers that are each proximately located with respect to each other and that are each owned by the same entity. In some embodiments, the collection of freezers is deemed to be proximately located when they are in the same building, same campus, or within five miles of each other. In some embodiments, the collection of freezers is deemed to be proximately located when it is possible to retrieve any source construct identified in the freezer store database within thirty minutes, within twenty minutes, within 10 minutes, within five minutes, or within one minute.

In some embodiments, the freezer store database 602 comprises information for 1000 or more source constructs 602 and the corresponding freezer store contains 1000 or more source constructs. In some embodiments, the freezer store database 602 comprises information for 10,000 or more source constructs 602 and the corresponding freezer store contains 10,000 or more source constructs. In some embodiments, the freezer store database 602 comprises information for 50,000 or more source constructs 602 and the corresponding freezer store contains 50,000 or more source constructs. In some embodiments, the freezer store database 602 comprises information for 100,000 or more source constructs 602 and the corresponding freezer store contains 100,000 or more constructs. In some embodiments, the freezer store database 602 comprises information for 500,000 or more source constructs 602 and the corresponding freezer store contains 500,000 or more constructs.

As illustrated in FIG. 6A, each source construct 602 comprise one or more component polynucleotides 604. Each such component polynucleotide 604 may or may not correspond to a component polynucleotide identified in expansion step 604. For instance, consider the case where expansion step 602 specifies the component polynucleotide 5'-$LA_1$-pFBA1-$LB_1$-3', where the nucleic acid sequences are shown added to the component polynucleotide. It is possible that none of the component polynucleotides 604 in freezer store database 62 will match 5'-$LA_1$-pFBA1-$LB_1$-3'. Moreover, it is possible that a component polynucleotide 604 in freezer store database 62 contains the promoter pFBA1 but not the linkers 5'-$LA_1$ and -$LB_1$-3'. For instance, the component polynucleotide 604 that contains pFBA1 may in fact be 5'-$LA_2$-pFBA1-$LB_2$-3'. In this case, the component polynucleotide 5'-$LA_2$-pFBA1-$LB_2$-3' will not be considered a match to 5'-$LA_1$-pFBA1-$LB_1$-3' because the linkers do not match up.

In the form illustrated in FIG. 6A, each of the component polynucleotides 604 for a given source construct 602 are listed sequentially in their contiguous 5' to 3' order. Thus, referring to source construct 602, the construct comprises 5'-component polynucleotide 1-1-component polynucleotide 1-2-component polynucleotide 1-A-3'.

To exhaustively query the freezer store database 62 for presence of component polynucleotides, a number of different queries are made. In some embodiments, these queries are performed in any order. In some embodiments, these queries are performed simultaneously, concurrently or sequentially. In some embodiment, only a subset of these queries are made. FIGS. 4A and 4B collectively list out an exhaustive set of queries that could be made for the exemplary $AR_i$ 5'-$LA_1$-pFBA1-$LB_1$-3',5'-$LA_2$-ADH2-$LB_2$-3',5'-$LA_3$-pSLN1-$LB_3$-3',5'-$LA_4$-ADH1-$LB_4$-3' which encodes the plurality of nucleic acid requests HO^::pFBA1>ADH2::pSLN1>ADH1. Among the queries that are made are queries for the absence or presence of each of 5'-$LA_1$-pFBA1-$LB_1$-3',5'-$LA_2$-ADH2-$LB_2$-3',5'-$LA_3$-pSLN1-$LB_3$-3',5'-$LA_4$-ADH1-$LB_4$-3' in source constructs in the freezer store database 62. These component polynucleotides are illustrated in FIG. 4A. This can be tested, for example, by a first query in which a determination is made as to whether the sequence 5'-$LA_1$-pFBA1-$LB_1$-3' is found in any source construct in database 62, a second query in which a determination is made as to whether the sequence 5'-$LA_2$-ADH2-$LB_2$-3' is found in any source construct in database 62, a third query in which a determination is made as to whether the sequence 5'-$LA_3$-pSLN1-$LB_3$-3' is found in any source construct in database 62, a fourth query in which a determination is made as to whether the sequence 5'-$LA_4$-ADH1-$LB_4$-3' is found in any source construct in database 62. If one or more of these four sequences are in the freezer store database 62, they likely are each in a different assembly vector. Assembly vectors are described in further detail in Section 5.13 below. Assembly vectors are a form of source construct in accordance with the present disclosure. As discussed above, in typical embodiments, a component polynucleotide 604 in freezer store database 602 is not deemed a match to a query component polynucleotide in $AR_i$ unless they use the same 3' and 5' linkers.

In some optional embodiments, in addition to querying for the presence of single component polynucleotides in source constructs in the freezer store database 62, queries are made for all possible subsets of the arrangement $AR_i$ in a single source construct 602 represented in freezer store database 62. These component polynucleotides are illustrated in FIG. 4B. For instance, in the example presented, in addition to making a query for the presence of each single component polynucleotide, a query is made to determine if any of the component polynucleotides found FIG. 4B are in the freezer store database 62. As FIGS. 4A and 4B collectively show, in the case where there are four component polynucleotides collectively representing the plurality of nucleic acid requests where each respective component polynucleotide is bound by linkers, a total of 4*(4−1)*2*1 queries are made. More generally, in the case of n component polynucleotides collectively representing the plurality of nucleic acid requests where each respective polynucleotide request is bound by at least one linker at its 5' or 3' end, a total of 4*(4−1)*2*1 queries are made, which number is called "n factorial" and written "n!". Source constructs 602 that encode more than one component polynucleotide are referred to as stitch vectors. Stich vectors are otherwise identical to assembly vectors accept that they include two or more component polynucleotides in contiguous order, where the two or more component polynucleotides are each separated by a linker from the library of nucleic acid sequences 64.

In some embodiments, the 3' or 5' terminus, or both the 3' and 5' termini, of each respective component polynucleotide in a stitch vector is bound to a corresponding linker from the predetermined library of linker nucleic acid sequences. For instance, consider the case where a stitch vector comprises component polynucleotides A and B. In a preferred embodiment, component polynucleotides would be encoded as $LA_x$-A-$LB_x$-B-$LB_{x+1}$.

A contribution to the score $S_i$ is made for the arrangement $AR_i$ when one or more source constructs are identified as being physically present in a freezer store, where the one or more physically present source constructs collectively encode all or a portion of $AR_i$. For instance, consider a first use case in which an arrangement $AR_i$ comprises twenty component polynucleotides. Upon querying the freezer store database 62, a determination is made that four of the twenty component polynucleotides are physically present in the freezer store database 62 and that each of the four component polynucleotides use linker nucleic acid sequences specified for the four component polynucleotides by the $AR_i$. In this case, the arrangement $AR_i$ receives a score of four arbitrary units. Each arbitrary unit is for one of the four component polynucleotides that are physically present in the freezer store database 62. Alternatively, suppose that upon querying the freezer store database 62, the determination is made that ten of the twenty component polynucleotides are physically present in the freezer store database 62 and that each of these ten component polynucleotides use linker nucleic acid sequences specified for the ten component polynucleotides by the $AR_i$. The arrangement would receive a score of ten arbitrary units.

Other scoring methods in which a contribution is made to the score $S_i$ for an arrangement $AR_i$ when one or more source constructs 602 that encode all or a portion of $AR_i$ are identified as being physically present in a freezer store are possible. For example, a lookup table may include a score to be added to $S_i$ for the occurrence of any given component polynucleotide of step 204 in the one or more source constructs. For instance, consider the case in which a first source construct comprises a first component polynucleotide and a second source construct comprises a second component polynucleotide. To determine the contribution made by the first component polynucleotide, a lookup table is consulted to retrieve the value of the first component polynucleotide. To determine the contribution made by the second component polynucleotide, a lookup table is consulted to retrieve the value of the second component polynucleotide. Consider the case in which the first component polynucleotide has a value of three arbitrary units and the second component polynucleotide has a value of seven arbitrary units. In this case, the total contribution of the first and second component polynucleotides is ten arbitrary units.

In another scoring method in accordance with the present disclosure, the score of a component polynucleotide is determined by a length of the component polynucleotide relative to the length of the engineered nucleic acid. For instance, consider the case in which a component polynucleotide is thirty percent of the total length of the engineered nucleic acid construct. In this instance, the component polynucleotide, when present in a qualifying source construct represented in freezer store database 62, will contribute a sufficient number of arbitrary units to achieve 30 percent of a perfect score. In some embodiments, the source construct is qualifying when it uses the same selectable marker specified for the engineered nucleic acid construct and when the specified component polynucleotide uses the same linkers called for the specified component polynucleotide in $AR_i$.

In light of the present disclosure, those of skill in the art will appreciate that a broad range of scoring schemes in which a contribution is made to $S_i$ when one or more component polynucleotides 604 are present in source constructs in a freezer store are possible and all such scoring schemes are within the scope of the present invention. The disclosed scoring schemes are simply meant to illustrate some of the many possible scoring schemes.

In some embodiments, the 3' or 5' terminus, or both the 3' and 5' termini, of each respective component polynucleotide in the one or more component polynucleotides encoded by the one or more physically present source constructs is bound to a corresponding linker from the predetermined library of linker nucleic acid sequences. This facilitates the construction of the engineered nucleic acid construct through splice overlap extension assembly reaction followed by polymerase chain reaction (SOE/PCR), as disclosed in U.S. patent application Ser. No. 12/622,401 (Pub. No. 2010/0136633 A1), filed Nov. 19, 2009, which is hereby incorporated by reference herein in its entirety.

In some embodiments, step 208 comprises determining whether a source construct having all or a subset of the plurality of component polynucleotides, in the contiguous order specified by the contiguous arrangement $AR_i$, is present in the freezer store, and a contribution the source construct makes to the score $S_i$ for the contiguous arrangement $AR_i$ is dependent upon a number of component polynucleotides in the source construct that are in the contiguous order specified by the contiguous arrangement $AR_i$.

In some embodiments, step 208 determines a score $S_i$ for a contiguous arrangement $AR_i$ by (i) identifying a first source construct in the freezer store, the first source construct having a first subset of the plurality of component polynucleotides, in the contiguous order specified by the contiguous arrangement $AR_i$, (ii) identifying a second source construct in the freezer store, the second source construct having a second subset of the plurality of component polynucleotides, in the contiguous order specified by the contiguous arrangement $AR_i$, where there is no overlap between the first subset and the second subset. A first contribution to the score $S_i$ for the contiguous arrangement $AR_i$ is based upon a number of component polynucleotides in the first source construct that are in the contiguous order specified by the contiguous arrangement $AR_i$ and a second contribution to the score $S_i$ for the contiguous arrangement $AR_i$ is based upon a number of component polynucleotides in the second source construct that are in the contiguous order specified by the contiguous arrangement $AR_i$.

In some embodiments, step 208 determines a score $S_i$ for a contiguous arrangement $AR_i$ by identifying a set of $\{C_1, \ldots, C_q\}$ source constructs in the freezer store, where q is a positive integer greater than 1, for a contiguous arrangement $AR_i$ in the set of contiguous arrangements $\{AR_1, \ldots, AR_m\}$, each respective source construct $C_i$ in $\{C_1, \ldots, C_q\}$ having a corresponding subset $S_i$ of component polynucleotides in the plurality of component polynucleotides identified in the expansion step 204, in the contiguous order specified by the contiguous arrangement $AR_i$, where the corresponding subset $S_i$ of component polynucleotides is not found in any other source construct in $\{C_1, \ldots, C_q\}$. In other words, the component polynucleotides in any given source construct $C_i$ in $\{C_1, \ldots, C_q\}$ are not found in any other source construct in $\{C_1, \ldots, C_q\}$. In such embodiments, a contribution to the score $S_i$ for $AR_i$ from each respective $C_i$ in $\{C_1, \ldots, C_q\}$ is based upon a number of component polynucleotides in $C_i$ that are in a contiguous order specified by $AR_i$.

In some embodiments the one or more physically present source constructs selected for $AR_i$ collectively encode a portion of $AR_i$. In some embodiments, the one or more component polynucleotides in the one or more physically present source constructs identified for $AR_i$ is less than 90 percent of a nucleic acid sequence defined by $AR_i$. In some embodiments, the one or more component polynucleotides in the one or more physically present source constructs identified for $AR_i$ is less than 80 percent of a nucleic acid sequence defined by $AR_i$. In some embodiments, the one or more component polynucleotides in the one or more physically present source constructs identified for $AR_i$ is less than 60 percent, less than 50 percent, less than 40 percent, less than 30 percent, less than 20 percent or less than 10 percent of a nucleic acid sequence defined by $AR_i$. In some embodiments, the one or more component polynucleotides in the one or more physically present source constructs identified for $AR_i$ is more than 10 percent of a nucleic acid sequence defined by $AR_i$. In some embodiments, the one or more component polynucleotides in the one or more physically present source constructs identified for $AR_i$ is more than 20 percent, more than 30 percent, more than 40 percent, more than 50 percent, more than 60 percent or more than 80 percent of a nucleic acid sequence defined by $AR_i$.

Step 210.

In step 210, a determination is made as to whether a threshold number of arrangements have been evaluated. In some embodiments, a threshold number of arrangements have been evaluated when all possible arrangements of the component polynucleotides have been scored. It will be appreciated that, in some instances, the order of some of the component polynucleotides must remain fixed. For instance, the component polynucleotide encoding a promoter for a gene is to immediately precede the component polynucleotide for the gene itself. However, as discussed above, in many instances such as where multiple genes are being inserted into a locus, component polynucleotides may be arranged in several different ways. Thus, in the embodiment that requires that each possible arrangement be evaluated, these component polynucleotides are permuted through each possible arrangement to construct the set of $\{AR_1, \ldots, AR_m\}$ arrangements and each possible arrangement is scored in successive or concurrent instances of steps 206 and 208.

In some embodiments, arrangements of the component polynucleotides that would cause a repeat sequence of greater than a predetermined number of bases to arise in the engineered nucleic acid construct are barred. In some embodiments, this threshold number is ten nucleic acids, eleven nucleic acids, twelve nucleic acids, thirteen nucleic acids, fourteen nucleic acids, fifteen nucleic acids, sixteen nucleic acids, seventeen nucleic acids, eighteen nucleic acids, nineteen nucleic acids, twenty nucleic acids, twenty-one nucleic acids, twenty-two nucleic acids, twenty-three nucleic acids, twenty-four nucleic acids, or twenty-five nucleic acids or more.

In some embodiments, a threshold number of arrangements has been evaluated when five or more, ten or more, twenty or more, thirty or more, forty or more, fifty or more, one hundred or more, two hundred or more, three hundred or more, four hundred or more, five hundred or more, or one thousand or more different arrangements have been evaluated.

In some embodiments, repetition of steps 206 and 208 or any other form of execution of these steps 206 and 208 (e.g., concurrent, etc.) results in a set of contiguous arrangements $\{AR_1, \ldots, AR_m\}$. In some embodiment the threshold number of arrangements has been evaluated (created) when the set of contiguous arrangements $\{AR_1, \ldots, AR_m\}$ consists of each possible unique complete contiguous arrangement of the component polynucleotides in the plurality of component polynucleotides. In such embodiments, contiguous arrangements of the component polynucleotides that place component polynucleotides in positions that will not construct the plurality of nucleic acid requests are not considered possible arrangements. For instance, arrangements that would cause a component polynucleotide encoding a promoter to be somewhere other than at the 5' end of the component polynucleotide encoding the gene to be expressed by the promoter are not considered allowed. In some embodiments, the threshold number of arrangements has been evaluated (created) when the set of contiguous arrangements $\{AR_1, \ldots, AR_m\}$ consists of a randomized subset of all possible unique complete contiguous arrangements of the component polynucleotides in the plurality of component polynucleotides. In some embodiments, this threshold number is ten percent multiplied by the number of possible unique complete contiguous arrangements of the component polynucleotides in the plurality of component polynucleotides, aside from those arrangements that are barred because they would not enact the plurality of nucleic acid requests. In some embodiments, this threshold number is twenty percent, thirty percent, forty percent, fifty percent, sixty percent, seventy percent, eighty percent or ninety percent multiplied by the number of possible unique complete contiguous arrangements of the component polynucleotides in the plurality of component polynucleotides, aside from those arrangements that are barred because they would not enact the plurality of nucleic acid requests.

Step 212.

In step 212, a final contiguous arrangement $AR_f$ in $\{AR_1, \ldots, AR_m\}$ having a score $S_i$ that meets a selection criterion is selected as an optimal contiguous arrangement. In some embodiments, the selection criterion is achieving a maximum score and the arrangement $AR_i$ in $\{AR_1, \ldots, AR_m\}$ that has a maximum score, determined in an instance of step 208, relative to the scores of all other arrangements in $\{AR_1, \ldots, AR_m\}$ is selected as the optimal contiguous arrangement. In some embodiments, the selection criterion is exceeding a threshold score and any arrangement $AR_i$ in $\{AR_1, \ldots, AR_m\}$ having a score determined in an instance of step 208 that exceeds this threshold score is selected as the optimal contiguous arrangement. In some embodiments, the selection criterion is achieving a minimum score and the arrangement $AR_i$ in $\{AR_1, \ldots, AR_m\}$ that has a minimum score, determined in an instance of step 208, relative to the scores of all other arrangements in $\{AR_1, \ldots, AR_m\}$ is selected as the optimal contiguous arrangement. In some embodiments, the selection criterion is falling below a threshold score and any arrangement $AR_i$ in $\{AR_1, \ldots, AR_m\}$ having a score determined in an instance of step 208 that falls below this threshold score is selected as the optimal contiguous arrangement.

In some embodiments, step 212 is done after each instance of step 208, rather than after step 210 as shown in FIG. 2, and the selection criterion is identification of the first $AR_i$ to have a score that exceeds a first predetermined threshold or falls below a second predetermined threshold.

Step 214.

In step 214, one or more primer pairs are calculated based upon the final contiguous arrangement $AR_f$. Each primer pair in the one or more primer pairs is capable of amplifying a portion of $AR_f$ not represented in the one or more physically present source constructs identified for $AR_f$.

Figure 5:
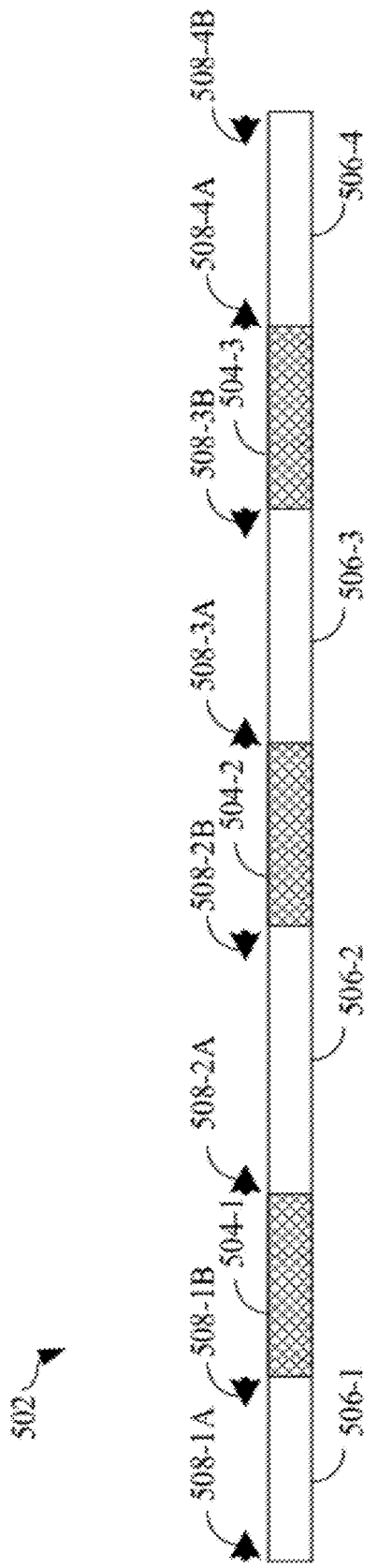

In FIG. 5, element 502 represents the final contiguous arrangement $AR_f$, encoding an engineered nucleic acid. Consider the case in which there were three source constructs identified for $AR_f$ in the instance of step 208 in which the score for $AR_f$ was computed and that each of these three source constructs encodes one component nucleotide identified in step 204 for the plurality of nucleic acid requests $\{NR_1, \ldots, NR_n\}$. Referring to FIG. 5, the three source constructs encode the hashed portions 504 of the final contiguous arrangement $AR_f$ 502. That is, each hashed portion 504 is a component nucleotide identified in step 204. Thus, what remains unrepresented in $AR_f$ 502 are the regions 506.

In step 214, primer pairs 508 are calculated in order to encode portions 506. For example, unrepresented portions 506 may each be of sufficient size such that only a single pair of primers 508 is needed for each unrepresented portion. This is the case illustrated in FIG. 5. However, it is possible that each unrepresented portion 506 requires two or more pairs of primers, three or more pairs of primers, four or more pairs of primers in order to amplify such portions 506 from a library of DNA that includes the genomic locus of the target organism to which the plurality of nucleic acid requests $\{NR_1, \ldots, NR_n\}$ is directed.

Furthermore, since portions 506 need to combined with hashed portions 504, the arrangement $AR_f$ includes linker nucleic acid sequences from the library of linker nucleic acid sequences 64 for the portions 506 that will allow for such recombination to occur. It will be appreciated that portions 506 represent component polynucleotides that could not be found in the freezer store database 62 with the linker nucleic acid sequences specified by $AR_f$. In typical embodiments, the linker nucleic acid sequences used for portions 506 is limited to the design criterion that any given linker nucleic acid sequence in the library of linker nucleic acid sequences 64 only be used once in any given engineered nucleic acid construct. By adhering to this design criterion, it is possible to recombine portions 506 with hashed portions 504 using a splice overlap extension assembly reaction followed by polymerase chain reaction (SOE/PCR), as disclosed in U.S. patent application Ser. No. 12/622,401 (Pub. No. 2010/0136633 A1), filed Nov. 19, 2009, which is hereby incorporated by reference herein in its entirety. Accordingly, in some embodiments, step 214 comprises encoding a linker nucleic acid sequence specified for $AR_f$ by the instance of step 206 that made arrangement $AR_f$ into a primer in the one or more primer pairs calculated for $AR_f$. In some embodiments, step 214 comprises encoding each respective linker nucleic acid sequence specified for portions 506 of $AR_f$ by the instance of step 206 that made arrangement $AR_f$ into the corresponding more primer pairs calculated for $AR_f$.

In some embodiments, at least one design rule is used to identify suitable primers in the one or more primer pairs. In some embodiments, the at least one design rule is (i) avoidance of hair pin termini, (ii) avoidance of self-dimerization, (iii) primer length between 17 and 28 bases, (v) percent G+C content between fifty and sixty percent, (vi) melting temperature between 55° C. and 80° C., or (vii) avoidance of runs of three or more Cs or Gs at the 3' terminus. In some embodiments any combination of 2, 3, 4, or 5 of the following design rules is used to identify suitable primers in the one or more primer pairs: (i) avoidance of hair pin termini, (ii) avoidance of self-dimerization, (iii) primer length between 17 and 28 bases, (v) percent G+C content between fifty and sixty percent, (vi) melting temperature between 55° C. and 80° C., or (vii) avoidance of runs of three or more Cs or Gs at the 3' terminus.

As illustrated in FIG. 5, the portions 504 of the contiguous arrangement $AR_f$ amplified by the one or more primer pairs 508 and the one or more component polynucleotides 506 in the one or more physically present source constructs identified for $AR_f$, in the order specified in the contiguous arrangement $AR_f$, collectively define the engineered nucleic acid construct.

In some embodiments, the engineered nucleic acid construct comprises a first PCR product having a first part of a selectable marker, and a second PCR product having a second part of a selectable marker, where the first PCR product, oriented in a 5' to 3' direction, combines with the second PCR product, oriented in a 3' to 5' direction, to form the engineered nucleic acid construct with the selectable marker, and where the one or more primer pairs computed for the engineered nucleic acid construct comprises a first primer pair and a second primer pair, where the first primer pair defines the termini of the first PCR product and the second primer pair defines the termini of the second PCR product.

Upon completion of step 214, all the components necessary for making an engineered nucleic acid construct are formed. This typically includes an identification of one or more source constructs in the freezer stores and a set of primer pairs that can be used against a genomic library that includes locus L to synthesize the missing source constructs.

In some embodiments, the selecting step 212 further comprises selecting a plurality of contiguous arrangements in $\{AR_1, \ldots, AR_m\}$, including $AR_f$ where each contiguous arrangement $AR_i$ in the plurality of contiguous arrangements has a score $S_i$ that meets a selection criterion. This embodiment differs from what was presented above in the sense that multiple arrangements are selected for further processing, rather than just one, and multiple instances of the engineered nucleic acid constructs are defined. Such an embodiment is desirable, for instance, in high priority situations in which several different versions of the engineered nucleic acid construct are tested in vivo to identify one that works the best. In such embodiments, step 214 further comprises calculating, for each respective contiguous arrangement $AR_i$ in the plurality of contiguous arrangements, one or more primer pairs based upon the respective contiguous arrangement, the one or more primer pairs collectively capable of amplifying the portions of the respective contiguous arrangement $AR_i$ not represented in the one or more component polynucleotides in the physically present source constructs identified for $AR_i$, where the portions of the contiguous arrangement amplified by the one or more primer pairs and the one or more component polynucleotides in the one or more physically present source constructs identified for $AR_i$, in the order specified in the contiguous arrangement $AR_i$, collectively define an instance of the engineered nucleic acid construct. In some embodiments, the plurality of contiguous arrangements comprises two contiguous arrangements, three contiguous arrangements, four contiguous arrangements, five contiguous arrangements, six contiguous arrangements, ten contiguous arrangements, twenty contiguous arrangements, thirty contiguous arrangements, forty contiguous arrangements, or fifty contiguous arrangements.

It will be appreciated that the aforementioned steps, as summarized in FIG. 2, are in silico steps. In some embodiments, the method further comprises outputting the nucleic acid construct to a tangible memory, a computer monitor, or some other non-transitory memory or device. For instance, a manifest of primer pairs and component polynucleotides in the freezer store necessary to synthesize the engineered nucleic acid construct is outputted to a tangible memory, a computer monitor or some other non-transitory memory or device. In some embodiments, the method further comprises actual physical synthesis of the engineered nucleic acid construct. For example, the engineered nucleic acid construct can be synthesized by a splice overlap extension assembly reaction followed by polymerase chain reaction (SOE/PCR), as disclosed in U.S. patent application Ser. No. 12/622,401 (Pub. No. 2010/0136633 A1), filed Nov. 19, 2009, which is hereby incorporated by reference in its entirety as well as section 5.14, below. Next, the engineered nucleic acid construct can be contacted with the genome of the target organism or host cell under conditions suitable for homologous recombination, thereby achieving the plurality of $\{NR_1, \ldots, NR_n\}$ nucleic acid requests at L.

It will also be appreciated that while the foregoing exemplary method for defining an engineered nucleic acid construct having multiple arrangements comprises steps 202, 204, 206, 208, 212, and 214 as illustrated in FIG. 2, other methods are provided herein which comprise only a subset of the foregoing steps. For example, in other aspects, provided herein are methods for defining an engineered nucleic acid construct comprising steps 202, 204 and 206; comprising steps 202, 204, 206 and 208; or comprising steps 202, 204, 206, 208 and 212.

5.5 Additional Exemplary Method for Polynucleotide Assembly—Single Arrangement

Section 5.4 discloses methods in which several different contiguous arrangements of component polynucleotides, each effecting a common plurality of nucleic acid requests 50 $\{NR_1, \ldots, NR_n\}$, are evaluated. In some embodiments, referring to FIG. 12, only a single arrangement that effects a plurality of nucleic acid requests 50 $\{NR_1, \ldots, NR_n\}$ is evaluated. Several of the steps in the method disclosed in FIG. 12 are identical to corresponding steps in FIG. 2. Thus, it will be appreciated that the disclosure for such corresponding steps presented above in Section 5.4 is equally applicable to the equivalent steps in the methods summarized in FIG. 12 and disclosed in this section. Thus, for the sake of brevity and ease of understanding the disclosure, such teachings will not be repeated in this Section. Steps in the method illustrated in FIG. 12 that correspond to steps in FIG. 2 are given the same number as the step found in FIG. 12, with the exception that the steps are denoted with the prime "'" symbol.

Step 202'.

In step 202', a plurality of nucleic acid requests {$NR_1, \ldots, NR_n$} are received, where n is a positive integer greater than 1. Each nucleic acid request $NR_i$ in {$NR_1, \ldots, NR_n$} specifies a genetic change to L. In some embodiments, an identity of a selectable marker is received with the plurality of nucleic acid requests in step 202'. In some embodiments an identity of the selectable marker is determined without human intervention from a predetermined list of selectable markers in step 206' and the selectable marker is included in the engineered nucleic acid construct.

In some embodiments, a nucleic acid request in {$NR_1, \ldots, NR_n$} specifies insertion of an insertion sequence at L. In some embodiments the insertion sequence comprises a promoter and a gene to be expressed by the promoter. In some embodiments, the insertion sequence comprises a divergent promoter and a first gene and a second gene driven by the divergent promoter. In some embodiments the divergent promoter is a back-to-back divergent promoter, an overlapping divergent promoter, or a face-to-face divergent promoter. In some embodiments, the insertion sequence comprises a promoter, a gene, a terminator, an open reading frame, a codon substitution, a nucleic acid substitution, a point mutation, an insertion mutation, or a deletion mutation. In some embodiments, the insertion sequence comprises a fusable open reading frame without a stop codon.

In some embodiments, a nucleic acid request in {$NR_1, \ldots, NR_n$} specifies that the entire genomic locus L is to be replaced by the insertion sequence. In some embodiments, the nucleic acid request specifies that a promoter and a gene at L are to be replaced by the insertion sequence. In some embodiments, the nucleic acid request specifies that a divergent promoter and a first gene and a second gene driven by the divergent promoter at L are to be replaced by the insertion sequence. In some embodiments, the divergent promoter is a back-to-back divergent promoter, an overlapping divergent promoter, or a face-to-face divergent promoter.

In some embodiments, a nucleic acid request in {$NR_1, \ldots, NR_n$} specifies that a promoter, a gene, a terminator, an open reading frame, a codon substitution, a nucleic acid substitution, a point mutation, an insertion mutation, or a deletion mutation at L is to be replaced by the insertion sequence. In some embodiments a nucleic acid request in {$NR_1, \ldots, NR_n$} specifies that a fusible open reading frame without a stop codon is to be replaced by the insertion sequence. In some embodiments, the insertion sequence includes a first copy of a gene in a 3' to 5' orientation and a second copy of the gene in a 5' to 3' orientation, and a bi-directional promoter between the first copy and the second copy.

Step 204'.

In step 204', each $NR_i$ in {$NR_1, \ldots, NR_n$} is expanded into a corresponding component polynucleotide 52, thereby forming a plurality of component polynucleotides. In some embodiments, the expanding step 204' comprises expanding a first nucleic acid request in {$NR_1, \ldots, NR_n$} into a first component polynucleotide and a second component polynucleotide, where the first component polynucleotide is a promoter and the second component polynucleotide is a gene.

Step 206'.

In step 206', the plurality of component polynucleotides are arranged into a contiguous arrangement $AR_i$, where the arranging uses linker nucleic acid sequences from a predetermined library of linker nucleic acid sequences 64 to combine component polynucleotides in the plurality of component polynucleotides into the contiguous arrangement. In some embodiments, the arranging 206' comprises inserting a selectable marker having a nucleic acid sequence into the contiguous arrangement $AR_i$. In some embodiments, the arranging comprises barring an $AR_i$ that would cause a repeat sequence of greater than a predetermined number of bases to arise in the engineered nucleic acid construct.

In some embodiments, a first component polynucleotide is identical to a second component polynucleotide in the plurality of component polynucleotides and the arranging of step 206' addresses this by barring a contiguous arrangement that would cause the first component polynucleotide and the second component polynucleotide to run in the same direction in the engineered nucleic acid construct.

In some embodiments, a first component polynucleotide shares a high degree of sequence similarity (e.g., at least 70%, 75%, 80%, 85%, 90% or 95%) to a second component polynucleotide in the plurality of component polynucleotides. In some embodiments, the first component polynucleotide comprises at least 100 contiguous nucleotides having at least 70%, 75%, 80%, 85%, 90% or 95% identity to the second polynucleotide. In some such embodiments, the arranging of step 206' addresses this by barring a contiguous arrangement that would cause the first component polynucleotide and the second component polynucleotide to run in the same direction in the engineered nucleic acid construct.

Step 1208.

In step 1208, one or more source constructs, from a plurality of source constructs physically present in a freezer store, are selected. Each of the one or more physically present source constructs encode one or more of the component polynucleotides. A 3' or 5' terminus, or both the 3' and 5' termini, of each respective component polynucleotide in the one or more component polynucleotides encoded by the one or more physically present source constructs is bound to a respective corresponding linker that was used for the corresponding component polynucleotide in step 206' to form the arrangement.

For example, consider the case in which the plurality of nucleic acid requests is HO^::pFBA1>ADH2:: pSLN1>ADH1 and the contiguous arrangement generated in step 206' comprises the component polynucleotides 5'-$LA_1$-pFBA1-$LB_1$-3',5'-$LA_2$-ADH2-$LB_2$-3',5'-$LA_3$-pSLN1-$LB_3$-3',5'-$LA_4$-ADH1-$LB_4$-3', where each $LB_i$, upon denaturation to single stranded form, is capable of hybridizing to the complement of $LA_{i+1}$, and where HO insertion sequences are not considered solely to simplify the example. A query is made of the freezer store database 62 to determine whether any of the component polynucleotides are present as source constructs.

An exemplary illustration of the architecture of a freezer store database 62 is provided in FIG. 6A. Freezer store database 62 comprises information about a plurality of source constructs 602. Each source construct 602 comprises one or more component polynucleotides 604. In typical embodiments, each source construct 602 is in circular vector form. An exemplary embodiment of a source construct 602 is an assembly vector. Assembly vectors are described in Section 5.13, below.

In typical embodiments, each respective source construct 602 in the freezer store indexed by freezer store database 62 contains a selectable marker and this selectable marker must match the selectable marker that has been selected for the engineered nucleic acid construct in order for the component polynucleotides within the respective source construct to be evaluated against the component polynucleotides of the $AR_i$.

In typical embodiments, a 3' or 5' terminus of each respective component polynucleotide 604 in the one or more component polynucleotides encoded by the one or more physically present source constructs 602 is bound to a corresponding linker in the library of linker nucleic acid sequences 64. Examples of when a component polynucleotide 604 in a source construct 602 is considered a match to a component polynucleotide in the $AR_i$ are addressed in Section 5.4 in conjunction with step 208 of the methods disclosed therein.

Step 1210.

In step 1210, one or more primer pairs are calculated based upon the $AR_i$. Each primer pair is capable of amplifying a portion of the $AR_i$ not represented in the one or more physically present source constructs identified for the $AR_i$. The portions of the $AR_i$ amplified by the one or more primer pairs and the one or more component polynucleotides in the one or more physically present source constructs identified for the $AR_i$, in the order specified by the $AR_i$, collectively define the engineered nucleic acid construct. Methods by which such primer pairs are computed are addressed in Section 5.4 in conjunction with step 214 of the methods disclosed therein.

In some embodiments, the calculating step 1210 comprises encoding a linker nucleic acid sequence from a predetermined library of linker nucleic acid sequences specified for the $AR_i$ into one or more primers in the one or more primer pairs calculated for the $AR_i$.

In some embodiments, the calculating step 1210 comprises applying at least one design rule to identify primers in the one or more primer pairs. In some embodiments, the at least one design rule is (i) avoidance of hairpin termini, (ii) avoidance of self-dimerization, (iii) a primer length between 17 and 28 bases, (iv) a percent G+C content between fifty and sixty percent, (v) a melting temperature between 55° C. and 80° C., or (vi) avoidance of runs of three or more cytosine or guanines at the 3' terminus of a primer.

In some embodiments, the engineered nucleic acid construct comprises a first PCR product having a first part of a selectable marker, and a second PCR product having a second part of a selectable marker, where the first PCR product, oriented in a 5' to 3' direction, combines with the second PCR product, oriented in a 3' to 5' direction, to form the engineered nucleic acid construct with the selectable marker, and where the one or more primer pairs computed for the engineered nucleic acid construct comprises a first primer pair and a second primer pair, where the first primer pair defines the termini of the first PCR product and the second primer pair defines the termini of the second PCR product.

Upon completion of step 1210, all the components necessary for making an engineered nucleic acid construct are formed. This typically includes an identification of one or more source constructs in the freezer stores and a set of primer pairs that can be used against a genomic library that includes locus L to synthesize the missing component polynucleic acids and their linkers.

It will be appreciated that the aforementioned steps, as summarized in FIG. 12, are in silico steps. In some embodiments, the method further comprises outputting the engineered nucleic acid construct to a tangible memory, a computer monitor, or some other non-transitory memory or device. For instance, a manifest of primer pairs and component polynucleotides in the freezer store necessary to synthesize the engineered nucleic acid construct is outputted to a tangible memory, a computer monitor or some other non-transitory memory or device. In some embodiments, the method further comprises actual physical synthesis of the engineered nucleic acid construct. For example, the engineered nucleic acid construct can be synthesized by a splice overlap extension assembly reaction followed by polymerase chain reaction (SOE/PCR), as disclosed in U.S. patent application Ser. No. 12/622,401 (Pub. No. 2010/0136633 A1), filed Nov. 19, 2009, which is hereby incorporated by reference in its entirety as well as section 5.14, below. Next, the engineered nucleic acid construct can be contacted with the genome of the target organism or host cell under conditions suitable for homologous recombination, thereby achieving the plurality of $\{NR_1, \ldots, NR_n\}$ nucleic acid requests at L.

It will also be appreciated that while the foregoing exemplary method for defining an engineered nucleic acid construct having a single arrangement comprises steps 202', 204', 206', 1208, and 1210 as illustrated in FIG. 12, other methods are provided herein which comprise only a subset of the foregoing steps. For example, in other aspects, provided herein are methods for defining an engineered nucleic acid construct comprising steps 202', 204' and 206'; or comprising steps 202', 204', 206' and 1208.

5.6 Additional Exemplary Method for Polynucleotide Assembly—Single Arrangement

Section 5.4 discloses methods in which several different contiguous arrangements, each effecting a common plurality of nucleic acid requests 50 $\{NR_1, \ldots, NR_n\}$ are evaluated. Section 5.5 discloses methods in which a single contiguous arrangement is made for a single plurality of nucleic acid requests 50 $\{NR_1, \ldots, NR_n\}$. In some embodiments, referring to FIG. 13, several different pluralities of nucleic acid requests 50 $\{NR_1, \ldots, NR_n\}$ are received and, for each respective plurality of nucleic acid requests 50 $\{NR_1, \ldots, NR_n\}$, an arrangement of component polynucleotides that effect the nucleic acid requests of the respective plurality of nucleic acid requests is evaluated.

Several of the steps in the method disclosed in FIG. 13 are identical to corresponding steps in FIG. 2. Thus, it will be appreciated that the disclosure for such corresponding steps presented above in Section 5.4 is equally applicable to the equivalent steps in the methods summarized in FIG. 13 and disclosed in this section. Thus, for the sake of brevity and ease of understanding the disclosure, such teachings will not be repeated in this section. Steps in the method illustrated in FIG. 13 that correspond to steps in FIG. 2 are given the same number as the step found in FIG. 13, with the exception that the steps are denoted with the double prime "''" symbol.

Step 202".

In step 202", a plurality of nucleic acid requests $\{NR_{i,1}, \ldots, NR_{i,n}\}$ corresponding to a request to make an engineered nucleic acid construct $EN_i$ in a plurality of engineered nucleic acid constructs $\{EN_1, \ldots, EN_k\}$ is received. Each nucleic acid request $NR_{i,j}$ in $\{NR_{i,1}, \ldots, NR_{i,n}\}$ specifies a genetic change to L. In some embodiments, an identity of a selectable marker is received with the plurality of nucleic acid requests in step 202". In some embodiments an identity of the selectable marker is determined without human intervention from a predetermined list of selectable markers in step 206" and the selectable marker is included in the corresponding engineered nucleic acid construct that is made for the plurality of nucleic acid requests $\{NR_{i,1}, \ldots, NR_{i,n}\}$.

In some embodiments, a nucleic acid request $NR_{i,j}$ in $\{NR_{i,1}, \ldots, NR_{i,n}\}$ specifies insertion of an insertion sequence at L. In some embodiments the insertion sequence comprises a promoter and a gene to be expressed by the promoter. In some embodiments, the insertion sequence comprises a divergent promoter and a first gene and a second gene driven by the divergent promoter. In some embodiments the divergent promoter is a back-to-back divergent promoter, an overlapping divergent promoter, or a face-to-face divergent promoter. In some embodiments, the insertion sequence comprises a promoter, a gene, a terminator, an open reading frame, a codon substitution, a nucleic acid substitution, a point mutation, an insertion mutation, or a deletion mutation. In some embodiments, the insertion sequence comprises a fusable open reading frame without a stop codon.

In some embodiments, a nucleic acid request $NR_{i,j}$ in $\{NR_{i,1}, \ldots, NR_{i,n}\}$ specifies that the entire genomic locus L is to be replaced by the insertion sequence. In some embodiments, the nucleic acid request $NR_{i,j}$ in $\{NR_{i,1}, \ldots, NR_{i,n}\}$ specifies that a promoter and a gene at L are to be replaced by the insertion sequence. In some embodiments, the nucleic acid request $NR_{i,j}$ in $\{NR_{i,1}, \ldots, NR_{i,n}\}$ specifies that a divergent promoter and a first gene and a second gene driven by the divergent promoter at L are to be replaced by the insertion sequence. In some embodiments, the divergent promoter is a back-to-back divergent promoter, an overlapping divergent promoter, or a face-to-face divergent promoter.

In some embodiments, a nucleic acid request $NR_{i,j}$ in $\{NR_{i,1}, \ldots, NR_{i,n}\}$ specifies that a promoter, a gene, a terminator, an open reading frame, a codon substitution, a nucleic acid substitution, a point mutation, an insertion mutation, or a deletion mutation at L is to be replaced by the insertion sequence. In some embodiments, a nucleic acid request $NR_{i,j}$ in $\{NR_{i,1}, \ldots, NR_{i,n}\}$ specifies that a fusible open reading frame without a stop codon is to be replaced by the insertion sequence. In some embodiments, the insertion sequence includes a first copy of a gene in a 3' to 5' orientation and a second copy of the gene in a 5' to 3' orientation, and a bi-directional promoter between the first copy and the second copy.

Step 204".

In step 204", each $NR_{i,j}$ in $\{NR_{i,1}, \ldots, NR_{i,n}\}$ is expanded into a plurality of component polynucleotides, thereby forming a corresponding plurality of component polynucleotides. In some embodiments, the expanding step 204" comprises expanding a first nucleic acid request $NR_{i,j}$ in $\{NR_{i,1}, \ldots, NR_{i,n}\}$ into a first component polynucleotide and a second component polynucleotide, where the first component polynucleotide is a promoter and the second component polynucleotide is a gene.

Step 206".

In step 206", the corresponding plurality of component polynucleotides of the last instance of step 204" are arranged into a contiguous arrangement $AR_i$ using linker nucleic acid sequences from a predetermined library 64 of linker nucleic acid sequences to combine the component polynucleotides in the corresponding plurality of component polynucleotides into the contiguous arrangement $AR_i$. In some embodiments, the arranging 206" comprises inserting a selectable marker having a nucleic acid sequence into the contiguous arrangement $AR_i$. In some embodiments, the arranging comprises barring an $AR_i$ that would cause a repeat sequence of greater than a predetermined number of bases to arise in the engineered nucleic acid construct.

In some embodiments, a first component polynucleotide is identical to a second component polynucleotide in the plurality of component polynucleotides and the arranging of step 206" addresses this by barring a contiguous arrangement that would cause the first component polynucleotide and the second component polynucleotide to run in the same direction in the engineered nucleic acid construct.

In some embodiments, a first component polynucleotide shares a high degree of sequence similarity (e.g., at least 70%, 75%, 80%, 85%, 90% or 95%) to a second component polynucleotide in the plurality of component polynucleotides. In some embodiments, the first component polynucleotide comprises at least 100 contiguous nucleotides having at least 70%, 75%, 80%, 85%, 90% or 95% identity to the second polynucleotide. In some such embodiments, the arranging of step 206" addresses this by barring a contiguous arrangement that would cause the first component polynucleotide and the second component polynucleotide to run in the same direction in the engineered nucleic acid construct.

In some embodiments, multiple arrangements are computed for a plurality of nucleic acid requests $\{NR_{i,1}, \ldots, NR_{i,n}\}$ corresponding to a request to make an engineered nucleic acid construct $EN_i$ in a plurality of engineered nucleic acid constructs $\{EN_1, \ldots, EN_k\}$. For example, in one embodiment, for at least one $NR_i$ in $\{NR_1, \ldots, NR_n\}$, the arranging step 206" comprises arranging the plurality of corresponding component polynucleotides corresponding to $NR_i$ from the expanding step 204" into a set of temporary contiguous arrangements $\{TAR_1, \ldots, TAR_z\}$ where, for each $TAR_i$ in $\{TAR_1, \ldots, TAR_z\}$, the arranging step 206" uses linker nucleic acid sequences from a predetermined library of linker nucleic acid sequences to combine component polynucleotides in the plurality of component polynucleotides into $TAR_i$. Then, a score $S_k$ is determined for each respective $TAR_k$ in $\{TAR_1, \ldots, TAR_z\}$, where, for each respective $TAR_k$ in $\{TAR_1, \ldots, TAR_z\}$, the corresponding score $S_k$ is determined by a method comprising (a) selecting one or more source constructs from a plurality of source constructs physically present in a freezer store, where the one or more source constructs collectively encode all a portion of $TAR_k$ (e.g., one or more component polynucleotides identified for $TAR_k$, one or more component polynucleotides identified for $TAR_k$ in which a 3' or 5' terminus is bound to a linker identified in step 206 for the one or more component polynucleotides, etc.) and (b) calculating $S_k$ based on an amount of $TAR_k$ represented by the one or more source constructs. The contiguous arrangement $TAR_f$ in $\{TAR_1, \ldots, TAR_m\}$ having a score $S_f$ that meets a selection criterion is selected as the optimal contiguous arrangement, where the selected $TAR_f$ is deemed to be the contiguous arrangement $AR_i$ for $EN_i$. Methods that can be used for scoring and exemplary selection criterion are disclosed in steps 208 and 212 of Section 5.4 and can be used for the embodiments described in this section. In this way, $\{AR_1, \ldots, AR_k\}$ are formed, where each $AR_i$ in $\{AR_1, \ldots, AR_k\}$ is for a different $NR_m$ in $\{NR_1, \ldots, NR_n\}$.

Step 1308.

In step 1308, a determination is made as to whether the plurality of nucleic acid requests, for each $EN_i$ in the plurality of engineered nucleic acid constructs $\{EN_1, \ldots, EN_k\}$, has been received and/or processed. It will be appreciated that the query of step 1308 is but one of many possible methods of processing the plurality of nucleic acid requests for each $EN_i$ in the plurality of engineered nucleic acid constructs $\{EN_1, \ldots, EN_k\}$. In alternative embodiments, multiple instances of steps 202", 204", and 206" are run simultaneously or concurrently, each set of instances 202", 204", and 206" for a different $EN_i$ in the plurality of engineered nucleic acid constructs $\{EN_1, \ldots, EN_k\}$. In still other embodiments, multiple instances of steps 202" are run, each for a different $EN_i$ in the plurality of engineered nucleic acid constructs $\{EN_1, \ldots, EN_k\}$, then multiple instances of steps 204" are run, each for a different $EN_i$ in the plurality of engineered nucleic acid constructs $\{EN_1, \ldots, EN_k\}$, and finally multiple instances of steps 206" are run, each for a different $EN_i$ in the plurality of engineered nucleic acid constructs $\{EN_1, \ldots, EN_k\}$.

The net result of steps 202", 204", and 206" and 1308 is that, for each respective $EN_i$ in $\{EN_1, \ldots, EN_k\}$, the corresponding plurality of component polynucleotides from the corresponding instance of step 204" is arranged into a contiguous arrangement $AR_i$, where the arranging uses linker nucleic acid sequences from a predetermined library of linker nucleic acid sequences to combine component polynucleotides in the corresponding plurality of component polynucleotides into the corresponding $AR_i$, thereby forming a plurality of contiguous arrangements $\{AR_1, \ldots, AR_m\}$, each $AR_i$ in $\{AR_1, \ldots, AR_m\}$ representing an $EN_i$ in $\{EN_1, \ldots, EN_k\}$.

Step 1310.

In step 1310, for each respective $EN_i$ in $\{EN_1, \ldots, EN_k\}$, one or more source constructs from a plurality of source constructs physically present in a freezer store are selected. Each of the one or more physically present source constructs for a respective $EN_i$ in $\{EN_1, \ldots, EN_k\}$ encodes one or more of the component polynucleotides in the plurality of component polynucleotides for the respective $EN_i$. A 3' or 5' terminus, or both the 3' and 5' termini, of each respective component polynucleotide in the one or more component polynucleotides encoded by the one or more physically present source constructs for a respective $EN_i$ is bound to a corresponding linker nucleic acid that was used for the respective component polynucleotide in the corresponding instance of the arranging step 206" to form the $AR_i$ that corresponds to the $EN_i$.

For example, consider the case in which the plurality of nucleic acid requests $\{NR_{i,1}, \ldots, NR_{i,n}\}$ is HO^::pFBA1>ADH2::pSLN1>ADH1 and the corresponding contiguous arrangement $AR_i$ generated in step 206" comprises the component polynucleotides 5'-$LA_1$-pFBA1-$LB_1$-3',5'-$LA_2$-ADH2-$LB_2$-3',5'-$LA_3$-pSLN1-$LB_3$-3',5'-$LA_4$-ADH1-$LB_4$-3', where each $LB_i$, upon denaturation to single stranded form, is capable of hybridizing to the complement of $LA_{i+1}$, and where HO insertion sequences are not considered solely to simplify the example. A query is made of the freezer store database 62 to determine whether any of the component polynucleotides are present as source constructs.

An exemplary illustration of the architecture of a freezer store database 62 is provided in FIG. 6A. Freezer store database 62 comprises information about a plurality of source constructs 602. Each source construct 602 comprises one or more component polynucleotides 604. In typical embodiments, each source construct 602 is in circular vector form. An exemplary embodiment of a source construct 602 is an assembly vector. Assembly vectors are described in Section 5.13, below.

In typical embodiments, each respective source construct 602 in the freezer store indexed by freezer store database 62 contains a selectable marker and this selectable marker must match the selectable marker that has been selected for the engineered nucleic acid construct in order for the component polynucleotides within the respective source construct to be evaluated against the component polynucleotides of the $AR_i$.

In typical embodiments, a 3' or 5' terminus of each respective component polynucleotide 604 in the one or more component polynucleotides encoded by the one or more physically present source constructs 602 is bound to a corresponding linker in the library of linker nucleic acid sequences 64. Examples of when a component polynucleotide 604 in a source construct 602 is considered a match to a component polynucleotide in the $AR_i$ are addressed in Section 5.4 in conjunction with step 208 of the methods disclosed therein.

Step 1312.

In step 1312, one or more primer pairs is calculated based upon $AR_i$, where each primer pair is capable of amplifying a portion of $AR_i$ not represented in the one or more physically present source constructs identified for $AR_i$. The portions of the $AR_i$ amplified by the one or more primer pairs and the one or more component polynucleotides in the one or more physically present source constructs identified for the $AR_i$, in the order specified by the $AR_i$, collectively define the engineered nucleic acid construct one or more primer pairs are calculated based upon the $AR_i$. Each primer pair is capable of amplifying a portion of the $AR_i$ not represented in the one or more physically present source constructs identified for the $AR_i$. The portions of the $AR_i$ amplified by the one or more primer pairs and the one or more component polynucleotides in the one or more physically present source constructs identified for the $AR_i$, in the order specified by the $AR_i$, collectively define the engineered nucleic acid construct $EN_i$. Methods by which such primer pairs are computed are addressed in Section 5.4 in conjunction with step 214 of the methods disclosed therein.

In some embodiments, the calculating step 1312 comprises encoding a linker nucleic acid sequence from a predetermined library of linker nucleic acid sequences specified for the $AR_i$ into one or more primers in the one or more primer pairs calculated for the $AR_i$.

In some embodiments, the calculating step 1312 comprises applying at least one design rule to identify primers in the one or more primer pairs. In some embodiments, the at least one design rule is (i) avoidance of hairpin termini, (ii) avoidance of self-dimerization, (iii) a primer length between 17 and 28 bases, (iv) a percent G+C content between fifty and sixty percent, (v) a melting temperature between 55° C. and 80° C., or (vi) avoidance of runs of three or more cytosine or guanines at the 3' terminus of a primer.

In some embodiments, an engineered nucleic acid construct $EN_i$ in $\{EN_1, \ldots, EN_k\}$ comprises a first PCR product having a first part of a selectable marker, and a second PCR product having a second part of a selectable marker, where the first PCR product, oriented in a 5' to 3' direction, combines with the second PCR product, oriented in a 3' to 5' direction, to form the engineered nucleic acid construct with the selectable marker, and where the one or more primer pairs computed for the engineered nucleic acid construct comprises a first primer pair and a second primer pair, where the first primer pair defines the termini of the first PCR product and the second primer pair defines the termini of the second PCR product.

Upon completion of step 1312, all the components necessary for making each engineered nucleic acid construct $EN_i$ in a plurality of engineered nucleic acid constructs $\{EN_1, \ldots, EN_k\}$ are provided. This typically includes an identification of one or more source constructs in the freezer stores and a set of primer pairs that can be used against a genomic library that includes locus L to synthesize the missing component polynucleotides.

It will be appreciated that the aforementioned steps, as summarized in FIG. 13, are in silico steps. In some embodiments, the method further comprises outputting the plurality of engineered nucleic acid constructs $\{EN_1, \ldots, EN_k\}$ to a tangible memory, a computer monitor, or some other non-transitory memory or device. For instance, a manifest of primer pairs and component polynucleotides in the freezer store necessary to synthesize each engineered nucleic acid constructs in the plurality of engineered nucleic acid constructs $\{EN_1, \ldots, EN_k\}$ is outputted to a tangible memory, a computer monitor, or some other non-transitory memory or device. In some embodiments, the method further comprises actual physical synthesis of each of the engineered nucleic acid constructs. For example, each of the engineered nucleic acid constructs can be synthesized by a splice overlap extension assembly reaction followed by polymerase chain reaction (SOE/PCR), as disclosed in U.S. patent application Ser. No. 12/622,401 (Pub. No. 2010/0136633 A1), filed Nov. 19, 2009, which is hereby incorporated by reference in its entirety as well as section 5.14, below. Next, each of the engineered nucleic acid constructs can be contacted with the genome of the target organism or host cell under conditions suitable for homologous recombination.

In some embodiments, the method disclosed in FIG. 13 and described in this section further comprises synthesizing, for each respective $EN_i$ in $\{EN_1, \ldots, EN_k\}$, $EN_i$, as defined by the $AR_i$ in $\{AR_1, \ldots, AR_m\}$ that represents $EN_i$, using the one or more primer pairs calculated for $AR_i$ in step 1312 and the one or more physically present source constructs selected for $AR_i$ in step 1310. In some embodiments, the method further comprises transforming each respective $EN_i$ in $\{EN_1, \ldots, EN_k\}$ synthesized in the above synthesizing step into a different host cell. In some embodiments, the method further comprises selecting a plurality of host cells, where each host cell in the plurality of host cells comprises an $EN_i$ in $\{EN_1, \ldots, EN_k\}$ such that the plurality of host cells represents at least ten percent, at least twenty percent, at least thirty percent, at least forty percent, at fifty sixty percent, at least sixty percent, at least seventy percent, at least eighty percent, at least ninety percent, or at least at least ninety-five percent of $\{EN_1, \ldots, EN_k\}$. In some embodiments, an engineered nucleic acid construct $EN_i$ in $\{EN_1, \ldots, EN_k\}$ comprises a selectable marker having a nucleic acid sequence and the host cell into which the engineered nucleic acid construct $EN_i$ is transformed is selected by propagating the transformed host cell on selectable media corresponding to the selectable marker.

In some embodiments, the plurality of $\{EN_1, \ldots, EN_k\}$ engineered nucleic acid constructs comprises one hundred engineered nucleic acid constructs and the transforming step described above is performed within two weeks of completion of the instances of the expanding step 204". In some embodiments, the plurality of $\{EN_1, \ldots, EN_k\}$ engineered nucleic acid constructs comprises two hundred engineered nucleic acid constructs and the transforming is performed within three weeks of completion of the instances of the expanding step 204". In some embodiments, the plurality of $\{EN_1, \ldots, EN_k\}$ engineered nucleic acid constructs comprises three hundred engineered nucleic acid constructs and the transforming step is performed within three weeks of completion of the instances of the expanding step 204". In some embodiments, the plurality of $\{EN_1, \ldots, EN_k\}$ engineered nucleic acid constructs comprises four hundred engineered nucleic acid constructs and the transforming step is performed within three weeks of completion of the instances of the expanding step 204". In some embodiments, the plurality of $\{EN_1, \ldots, EN_k\}$ engineered nucleic acid constructs comprises five hundred engineered nucleic acid constructs and the transforming step is performed within three weeks of completion of the instances of the expanding step 204".

It will be appreciated that while the foregoing exemplary method for defining an engineered nucleic acid construct having a single arrangement comprises steps 202", 204", 206", 1308, 1310, and 1312 as illustrated in FIG. 13, other methods are provided herein which comprise only a subset of the foregoing steps. For example, in other aspects, provided herein are methods for defining an engineered nucleic acid construct comprising steps 202", 204", and 206"; comprising steps 202", 204", 206", and 1308; or comprising steps 202", 204", 206", 1308, and 1310.

5.7 Graphical User Interface for Designing Engineered Nucleic Acid Constructs FIG. 3 further illustrates a graphical user interface 300 for designing engineered nucleic acids. Referring to FIG. 1, in some embodiment interface 300 is served by engineered nucleic acid assembly module 46 to a client across wide area network 34 (e.g., the Internet). Thus, the present disclosure provides an apparatus comprising one or more memories and one or more processors, where the one or more memories and the one or more processors are in electronic communication with each other, the one or more memories encoding a set of instructions for defining a plurality of engineered nucleic acid constructs $\{EN_1, \ldots, EN_k\}$, where k is an integer greater than 1, each engineered nucleic acid construct $EN_i$ in $\{EN_1, \ldots, EN_k\}$ for integration into a genomic locus L of a target organism or a host cell.

The set of instructions comprise instructions for receiving, for each respective $EN_i$ in $\{EN_1, \ldots, EN_k\}$, a corresponding plurality of nucleic acid requests $\{NR_{i,1}, \ldots, NR_{i,n}\}$ in digital alphanumeric format, each nucleic acid request $NR_{i,j}$ in $\{NR_{i,1}, \ldots, NR_{i,n}\}$ specifying a genetic change to L, where, for each respective $EN_i$ in $\{EN_1, \ldots, EN_k\}$, n is a positive integer that is the same or different as n for each other $EN_m$ in $\{EN_1, \ldots, EN_k\}$. Examples of a plurality of nucleic acid requests $\{NR_{i,1}, \ldots, NR_{i,n}\}$ in digital alphanumeric format are examples 304-1 through 304-14 of FIG. 3. For instance, referring to FIG. 3, the first plurality of nucleic acid requests 304-1 (pACT1>PTC1) specifies driving the PTC1 gene using the pATC promoter. Thus, a first engineered nucleic acid construct is made that effects these nucleic acid requests. Next, the second plurality of nucleic acid requests 304-2 specifies insertion of the SKN7 gene, driven by the pSLN1 promoter, into the HO locus. Thus, a second engineered nucleic acid construct is made that effects these nucleic acid requests. Advantageously, referring to FIG. 3, all a user needs to do is paste these requests into box 302. Once this is accomplished, the user interface 300 appears as illustrated in FIG. 14. Upon pressing the "Submit Genotypes" button 306, each plurality of nucleic acid requests $\{NR_{i,1}, \ldots, NR_{i,n}\}$ is then processed using any of the methods disclosed in sections 5.4, 5.5, or 5.6, above. An exemplary method by each plurality of nucleic acid requests $\{NR_{i,1}, \ldots, NR_{i,n}\}$ is presented in this section below.

In accordance with this exemplary method, the set of instructions further comprises instructions for expanding, for each respective $EN_i$ in $\{EN_1, \ldots, EN_k\}$, each $NR_{i,j}$ in $\{NR_{i,1}, \ldots, NR_{i,n}\}$ into a corresponding component polynucleotide having a nucleic acid sequence, thereby forming a corresponding plurality of component polynucleotides for each respective $EN_i$ in $\{EN_1, \ldots, EN_k\}$. Suitable methods for accomplishing this expansion are described in section 5.4, step 204.

In accordance with this exemplary method, the set of instructions further comprises instructions for arranging, for each respective $EN_i$ in $\{EN_1, \ldots, EN_k\}$, the corresponding plurality of component polynucleotides from the instructions for expanding into a contiguous arrangement $AR_i$, where the instructions for arranging use linker nucleic acid sequences from a predetermined library 64 of linker nucleic acid sequences to combine component polynucleotides in the plurality of corresponding component polynucleotides into $AR_i$, thereby forming a plurality of contiguous arrangements $\{AR_1, \ldots, AR_m\}$, each $AR_i$ in $\{AR_1, \ldots, AR_m\}$ representing an $EN_i$ in $\{EN_1, \ldots, EN_k\}$. Suitable methods for accomplishing this arranging are described in section 5.4, step 206.

In accordance with this exemplary method, the set of instructions further comprise instructions for selecting, for each respective $EN_i$ in $\{EN_1, \ldots, EN_k\}$, one or more source constructs from a plurality of source constructs physically present in a freezer store, where each of the one or more physically present source constructs for a respective $EN_i$ in $\{EN_1, \ldots, EN_k\}$ encode one or more of the component polynucleotides in the plurality of component polynucleotides for the respective $EN_i$, and where a 3' or 5' terminus, or both the 3' and 5' termini, of each respective component polynucleotide in the one or more component polynucleotides encoded by the one or more physically present source constructs for a respective $EN_i$ is bound to a corresponding linker nucleic acid that was used for the respective component polynucleotide in the arranging to form $AR_i$. Suitable methods for accomplishing this selecting are described in section 5.5, step 1208.

In accordance with this exemplary method, the set of instructions further comprise instructions for calculating, for each respective $EN_i$ in $\{EN_1, \ldots, EN_k\}$, one or more primer pairs based upon the $AR_i$ in $\{AR_1, \ldots, AR_m\}$ that represents $EN_i$, where each primer pair in the one or more primer pairs for an $AR_i$ is capable of amplifying a portion of $AR_i$ not represented in the one or more source constructs identified for $AR_i$, where the portions of $AR_i$ amplified by the one or more primer pairs and the one or more component polynucleotides in the one or more physically present source constructs identified for $AR_i$, in the order specified by $AR_i$, collectively define the engineered nucleic acid construct $EN_i$. Suitable methods for accomplishing this calculating are described in section 5.5, step 1210.

In an optional step in accordance with this exemplary method, the set of instructions further comprises instructions for outputting to a non-volatile computer memory, a non-transitory computer memory, a persistent data storage, a monitor, or a printer, for each respective $EN_i$ in $\{EN_1, \ldots, EN_k\}$, one or more primer pairs based upon the $AR_i$ in $\{AR_1, \ldots, AR_k\}$ that represents $EN_i$, and an identity of each of the one or more source constructs identified by the instructions for calculating for $E_i$.

In some embodiments, for each $NR_i$ in $\{NR_1, \ldots, NR_n\}$, the instructions for arranging comprise instructions for arranging the plurality of corresponding component polynucleotides corresponding to a $NR_i$ from the instructions for expanding into a set of temporary contiguous arrangements $\{TAR_1, \ldots, TAR_z\}$ where z is a positive integer greater than 1 and where, for each $TAR_i$ in $\{TAR_1, \ldots, TAR_z\}$, the instructions for arranging use linker nucleic acid sequences from the predetermined library 64 of linker nucleic acid sequences to combine component polynucleotides in the plurality of component polynucleotides into $TAR_i$. Then, a score $S_k$ is determined for each respective $TAR_k$ in $\{TAR_1, \ldots, TAR_z\}$, where, for each respective $TAR_k$ in $\{TAR_1, \ldots, TAR_z\}$, the corresponding score $S_k$ is determined by a method comprising selecting one or more source constructs from a plurality of source constructs physically present in a freezer store, where the one or more constructs collectively encode all a portion of $TAR_k$, and (b) calculating $S_k$ based on an amount of $TAR_k$ represented by the one or more source constructs, and (iii) selecting the contiguous arrangement $TAR_f$ in $\{TAR_1, \ldots, TAR_z\}$ having a score $S_f$ that meets a selection criterion as the optimal contiguous arrangement, where the selected $TAR_f$ is deemed to be the contiguous arrangement $AR_i$ for $EN_i$. In this way the set $\{AR_1, \ldots, AR_k\}$ is formed, where each $AR_i$ in $\{AR_1, \ldots, AR_k\}$ is for a different $NR_m$ in $\{NR_1, \ldots, NR_n\}$. In some embodiments, k is ten or greater, k is one hundred or greater, or k is one thousand or greater.

5.8 Additional Graphical User Interface for Designing Engineered Nucleic Acid Constructs Another aspect of the present disclosure provides an additional graphical user interface for designing engineered nucleic acid constructs. In one such embodiment of the present disclosure, an apparatus comprising one or more memories and one or more processors is provided, where the one or more memories and the one or more processors are in electronic communication with each other, the one or more memories encoding a set of instructions for defining an engineered nucleic acid construct for integration into a genomic locus L of a target organism or a host cell, using the one or more processors. In some embodiments, the graphical user interface and the set of instructions, is encoded by or directed or otherwise controlled by engineered nucleic acid assembly module 46.

Referring to FIG. 15, the set of instructions comprises instructions for listing as a table 1502 on a display 26, where the display 26 is in electronic communication with the one or more processors 22 as illustrated in FIG. 2. Table 1502 comprise a first plurality of component polynucleotides physically present in a freezer store. In practice, table 1502 is populated by all or a portion of the component polynucleotides in freezer store database 62. Advantageously, as illustrated in FIG. 15, information is provided for each respective component polynucleotide 52, such as the identity 802 of the respective component polynucleotide, the name 804 of the respective component polynucleotide, an identity of a 5' linker nucleic acid sequence 806-A, from the library of linker nucleic acid sequences 64, that is bound to the 5' end of the respective component polynucleotide, an identity of a 3' linker nucleic acid sequence 806-B, from the library of linker nucleic acid sequences 64, that is bound to the 3' end of the respective component polynucleotide, a direction 808 (5' to 3' or 3' to 5') of the respective component polynucleotide 52, a breed 810 of the respective component polynucleotide, a status 1502 of the respective component polynucleotide, the creator 1504 of the respective component polynucleotide, the creation date 1506 of the respective component polynucleotide, a source 812 of the respective component polynucleotide, and any selection tags 1510 that are encoded by the respective component polynucleotide.

The set of instructions further comprises instructions for receiving a first selection of a first component polynucleotide from the table by a user. For instance, the user may select component polynucleotide 51-1 by clicking on the row associated with this component polynucleotide.

Referring to FIG. 16, the set of instructions further comprises instructions for displaying, responsive to the first selection, an icon 1602 on the display for the first component polynucleotide, where the icon for the first component polynucleotide specifies an identity of a 5' linker nucleic acid sequence and an identity of a 3' linker nucleic acid sequence bound to the first component polynucleotide, where the 5' linker nucleic acid sequence and the 3' linker nucleic acid sequence are present in the electronic library of linker nucleic acid sequences 64 that is stored in non-transitory form in the one or more memories. For instance, consider the case in which a user selects component polynucleotide 52-1 illustrated in FIG. 15 by clicking on the row associated with this component polynucleotide. In this instance, responsive to the selection, component polynucleotide 52-1 is displayed as icon 1602-1 on the display. Icon 1602-1 details the 5' and the 3' linker nucleic acid sequences of component polynucleotide 51-1, "01" and "1", respectively, from the library of linker nucleic acid sequences 64. In some embodiments, a component polynucleotide does not have a bound 5' linker nucleic acid sequence. In such instances, no 5' linker nucleic acid sequence is displayed in the icon 1602 for the component polynucleotide. In some embodiments, a component polynucleotide does not have a bound 3' linker nucleic acid sequence. In such instances, no 3' linker nucleic acid sequence is displayed in the icon 1602 for the component polynucleotide.

The set of instructions further comprises instructions for updating the table on the display, responsive to the first selection, to provide a second plurality of component polynucleotides physically present in a freezer store. Each component polynucleotide in the updated table comprises a 5' linker nucleic acid sequence or a 3' linker nucleic acid sequence that, upon denaturation to single stranded form, is capable of hybridizing to the complement of the 5' linker nucleic acid sequence or the complement of the 3' linker nucleic acid sequence of the previously selected first component polynucleotide. For example, turning to FIG. 16, icon 1602-1 indicates that the 3' linker nucleic acid sequence is "3'-1". Thus, component polynucleotides 52 in the freezer store database 62 that include the 5' linker nucleic acid sequence "5'-1" will be listed in the updated table 1502. This is because "3'-1" stands for 1B and "5'-1" stands for 1A, and "5'-1", upon denaturation to single stranded form, is capable of hybridizing to the complement of "3'-1", thereby joining the two component polynucleotides.

The set of instructions further comprises instructions for receiving a second selection of a second component polynucleotide from the table by a user and instructions for displaying, responsive to the second selection, an icon on the display for the second component polynucleotide, where the icon for the second component polynucleotide specifies an identity of the 5' linker nucleic acid sequence and an identity of the 3' linker nucleic acid sequence bound to the second component polynucleotide. When the 5' linker nucleic acid sequence of the second component polynucleotide, upon denaturation to single stranded form, is capable of hybridizing to the complement of the 3' linker of the first component polynucleotide, the second icon is shown to the right of the first icon on the display, and when the 3' linker nucleic acid sequence of the second component polynucleotide upon denaturation to single stranded form, is capable of hybridizing to the complement of the 5' linker of the first component polynucleotide, the second icon is shown to the left of the first icon on the display. FIG. 16 illustrates. Component polynucleotide 1604-1 of FIG. 16, gHppFMD, includes a 5'-1 linker nucleic sequence and a 3'-A linker nucleic acid sequence. The 5'-1 linker nucleic sequence, upon denaturation to single stranded form, is capable of hybridizing to the complement of "3'-1". Thus, as illustrated in FIG. 17, when component polynucleotide 1604-1 of FIG. 16 is selected, an icon 1602-2 for gHppFMD is depicted to the right of icon 1602-1. The defined engineered nucleic acid construct comprises the first component polynucleotide and the second component polynucleotide.

The above-identified process can be repeated. For instance, in response to the second selection, the table is once again updated to include the component polynucleotides, from freezer store database 62, that have at least one linker nucleic acid sequence that, upon denaturation to the single stranded form, is capable of hybridizing to the complement of an exposed 5' or 3' linker nucleic acid sequence in the growing chain of component polynucleotides depicted as icons 1602. As illustrated in FIG. 17, one such linker nucleic acid is "5'-A" because, upon denaturation to the single stranded form, it is capable of hybridizing to the complement of exposed 3'-A of icon 1602-2 of FIG. 17. Thus, upon selection of, for example, component polynucleotide 1702-1 "ATGGGTgPSgcgGTcycl[136S:-1E]" of FIG. 17, the component polynucleotide is added as icon 1602-3 to the 3' end of the growing chain of icons illustrated in FIG. 18. As illustrated in FIG. 19, once a user has fully defined an engineered nucleic acid construct, it may be sent to a clone manger application for further processing, as illustrated by icon 1902 of FIG. 19.

In some embodiments, the electronic library of linker nucleic acid sequences consists of 100 linker nucleic acid sequences or less. In some embodiments, the electronic library of linker nucleic acid sequences consists of 50 linker nucleic acid sequences or less. In some embodiments, the engineered nucleic acid construct comprises, in a 5' to 3' orientation, A=an ordered set of component polynucleotides $\{X_1, \ldots, X_n\}$ having the sequential order displayed in the display, where, n is a positive integer greater than 1, each i is an integer in the set of integers $\{1, \ldots, n\}$, each $X_i$ comprises 5'-$LA_i$-$NA_i$-$LB_i$-3', each $LB_i$ is a linker nucleic acid sequence in a predetermined library of linker nucleic acid sequences, each $NA_i$ is a component polynucleotide, each $LB_i$, for i less than n, upon denaturation to single stranded form, is capable of hybridizing to the complement of $LA_{i+1}$, thereby forming the engineered nucleic acid construct comprising the nucleic acid sequence:

5'-$LA_1$-$NA_1$, ..., $LB_{n-1}$-$NA_n$-$LB_n$-3'.

In some embodiments:

B=$NA_0$-$LB_0$, and

C=$LA_{n+1}$-$NA_{n+1}$, where, $LB_0$ is a linker nucleic acid sequence in the electronic library of linker nucleic acid sequences, $NA_0$ and $NA_{n+1}$ are each component polynucleotides, the contiguous arrangement $AR_i$ comprising, in a 5' to 3' orientation, A, B, C, and where $LB_0$, upon denaturation to single stranded form, is capable of hybridizing to the complement of $LA_1$, and $LB_n$, upon denaturation to single stranded form, is capable of hybridizing to the complement of $LA_{n+1}$, so that the engineered nucleic acid construct comprises the nucleic acid sequence:

5'-$NA_0$-$LB_0$, ..., $LB_{n-1}$-$NA_n$-$LB_n$-$NA_{n+1}$-3'.

5.9 Methods of Querying a Freezer Store Database

Illustrated in FIG. 20 is a graphical user interface 2002 that allows for searching for DNA sequences in the freezer store database 62. A user pastes or types a polynucleic acid sequence into interface box 2004. Then, all of the possible matches are displayed, with the option to view alignment. Referring to FIG. 21, this expands the box and shows a comparison of the search result 2102 with the polynucleic acid query that was entered. In FIG. 21, the top row of the alignment 2101 is the search result, with the query result placed underneath it.

In more detail, an embodiment of the present disclosure provides an apparatus 10 comprising one or more memories 14/36 and one or more processors 22, where the one or more memories and the one or more processors are in electronic communication with each other as illustrated, for example, in FIG. 1. The one or more memories encode a set of instructions for determining whether a nucleic acid sequence is present in any source construct in a plurality of source constructs physically present in a freezer store, using the one or more processors. In some embodiments, the set of instructions is a component or module of engineered nucleic acid assembly module 46.

The set of instructions comprise instructions for receiving a first nucleic acid sequence in electronic alphanumeric format using a display in electronic communication with the one or more memories, as illustrated in FIG. 20. The set of instructions further comprise instructions for receiving a matching threshold criterion using the display. For example, referring to FIG. 20, a user toggles a similarity threshold indicator to dial for a similarity threshold of anywhere from 30% similarity to 100% similarity. In so doing, the user specifies how similar target nucleic acids must be in the plurality of source constructs to the query nucleic acid in order to be considered a match. In some embodiments, the matching threshold criterion is percent identity rather than percent similarity and the user can toggle anywhere in the range of 30% identity to 100% identity for matching nucleic acids.

In some embodiments, the set of instructions further comprises instructions for comparing the first nucleic acid sequence with a sequence of each respective source construct in the plurality of source constructs indexed by freezer store database 62. When a second nucleic acid sequence that satisfies the matching threshold criterion is found within the sequence of a respective source construct, the instructions for comparing further include instructions for displaying an identity of the respective source construct. In some embodiments, the plurality of source constructs comprises 1000 source constructs. In some embodiments, the plurality of source constructs comprises 10,000 source constructs. In some embodiments, the plurality of source constructs comprises 100,000 source constructs.

In some embodiments, when a second nucleic acid sequence that satisfies the matching threshold criterion is found within the sequence of a respective source construct, the instructions for comparing further include instructions for displaying an alignment of the second nucleic acid sequence against the first nucleic acid sequence. See, for example, alignment 2102 of FIG. 21. In FIG. 21, the amino acid sequence (SEQ ID NO. 1) of a nucleic acid sequence alignment between a source construct (SEQ ID NO. 2) and a target construct (SEQ ID NO. 3) is provided.

5.10 Methods of Generating Host Cells Comprising Assembled Polynucleotides

Another aspect provides methods for generating host cells comprising the engineered nucleic acid construct. In some embodiments, the engineered nucleic acid construct is less than 1 kilobase (kb) in size. In some embodiments, the engineered nucleic acid construct is at least 1 kb in size. In some embodiments, the engineered nucleic acid construct is at least 2 kb in size. In some embodiments, the engineered nucleic acid construct is at least 3 kb in size. In other embodiments, the engineered nucleic acid construct is at least 5 kb in size. In still other embodiments, the engineered nucleic acid construct is at least 6, 7, 8, 9, or 10 kb in size. In still other embodiments, the engineered nucleic acid construct is greater than 10 kb in size. In still other embodiments, the engineered nucleic acid construct is greater than 15 kb in size. In still other embodiments, the engineered nucleic acid construct is greater than 20 kb in size. In still other embodiments, the engineered nucleic acid construct is greater than 25 kb in size. In still other embodiments, the engineered nucleic acid construct is greater than 30 kb in size. In still other embodiments, the engineered nucleic acid construct is greater than 35 kb in size. In still other embodiments, the engineered nucleic acid construct is greater than 40 kb in size.

In some embodiments, methods are provided that comprise transforming a host cell with an engineered nucleic acid construct generated by the methods of polynucleotide assembly described herein. The engineered nucleic acid construct can be circularized prior to transformation or can be transformed as a linear molecule. The engineered nucleic acid construct can be maintained in a host cell as an extrachromosomal polynucleotide. Alternatively, the engineered nucleic acid construct can be integrated into the genome of the host cell, e.g., by host cell mediated homologous recombination. To integrate an engineered nucleic acid construct into the genome by homologous recombination, the engineered nucleic acid construct must comprise at one terminus a nucleic acid sequence comprising an upstream genomic targeting sequence and at the other terminus a nucleic acid sequence comprising a downstream genomic targeting sequence. Accordingly, an engineered nucleic acid construct that is to be integrated into a locus of a host cell is generated from an assembly composition comprising a first nucleic acid molecule comprising an upstream chromosomal targeting sequence and a last nucleic acid molecule comprising a downstream chromosomal targeting sequence, each chromosomal targeting sequence being of sufficient length to initiate homologous recombination by the host cell with its chromosome.

In other embodiments, the methods comprise transforming a host cell with a plurality of engineered nucleic acid construct generated by the methods of polynucleotide assembly described herein. In a particular embodiment, the host cell combines two or more engineered nucleic acid construct into a single combined polynucleotide by homologous recombination. Host cell transformants comprising the combined polynucleotides are selected by virtue of expressing a selectable marker that is generated in the process of combining the assembled polynucleotides. The method is particularly useful for inserting relatively large pieces of polynucleotide into a target locus by homologous recombination. For chromosomal integration to occur, the combined polynucleotide must comprise an upstream genomic targeting sequence located 5' or 3' of the coding sequence of the selectable marker and a downstream genomic targeting sequence located 3' or 5' of the coding sequence of the selectable marker, respectively. Genomic integration as used herein includes chromosomal integration, e.g., integration of a polynucleotide into a chromosome of a host cell. Suitable chromosomal integration sites in *Saccharomyces cerevisiae* include but are not limited to the NDT80, HO, GAL2, and GAL1-GAL10-GAL7 locus. The method can also be useful for generating host cells comprising an extrachromosomally maintained polynucleotide, e.g., vectors and expression plasmids. The stability of either a chromosomally integrated or an extrachromosomally maintained combined polynucleotide is increased when the combined polynucleotide does not comprise identical annealable linker nucleic acid sequences or DNA segments arranged as direct repeats that can otherwise initiate additional homologous recombination events resulting in the excision of segments of the component polynucleotide. Therefore, in some embodiments, the assembled polynucleotides comprise unique annealable linker nucleic acid sequences and DNA segments. In other embodiments, the assembled polynucleotides contain one or more identical annealable linker nucleic acid sequences or DNA segments that upon combination of the assembled polynucleotides are arranged as inverted repeats in the combined polynucleotide.

The generation of an exemplary combined polynucleotide and integration of the combined polynucleotide into a chromosome of the host cell by homologous recombination is illustrated in FIG. 8 of U.S. patent application Ser. No. 12/622,401 (Pub. No. 2010/0136633 A1), filed Nov. 19, 2009 and the corresponding text in the patent application which describes the figure, which is hereby incorporated by reference. Such techniques can be used for the engineered nucleic acid constructs of the present disclosure. In yet other embodiments, the methods comprise transforming a host cell with a plurality of engineered nucleic acid constructs and allowing the host cell to generate one or more engineered nucleic acid constructs by homologous recombination. The engineered nucleic acid construct can be extrachromosomally maintained in the host cell or integrated into the chromosome of the host cell. The generation of an exemplary assembled polynucleotide by homologous recombination in a host cell and integration of the assembled polynucleotide into the chromosome of the host cell is illustrated in FIG. 9 of U.S. patent application Ser. No. 12/622,401 (Pub. No. 2010/0136633 A1), filed Nov. 19, 2009 and the corresponding text in the patent application which describes the figure, which is hereby incorporated by reference herein. Such techniques can be sued for the generation of a engineered nucleic acid construct by homologous recombination.

Any host cell can be used in the methods describe herein. In particular embodiments, suitable host cells are host cells that are capable of recombining polynucleotides based on complementary sequence stretches such as provided by the selectable marker segments, genomic targeting sequences, and annealable linker nucleic acid sequences provided herein. Illustrative examples of such host cells include but are not limited to *Saccharomyces cerevisiae*. Conditions suitable for uptake of DNA by such host cells are well known in the art. More details on suitable host cells are described in Section 5.11 below.

Host cell transformants comprising an engineered nucleic acid construct can be readily identified by virtue of expressing a selectable marker encoded by the engineered nucleic acid construct that permits selection for or against the growth of the cells. The selectable marker may be encoded by a single DNA segment present in an assembly vector of an assembly composition. Alternatively, non-functional segments of the selectable marker may be encoded by DNA segments present in multiple assembly vectors of an assembly composition or in multiple assembled engineered nucleic acid construct such that a functional selectable marker is generated only upon generation of an assembled polynucleotide (e.g., engineered nucleic acid construct) or upon generation of a combined polynucleotide, respectively.

Auxotrophy can also be used to identify host cell transformants comprising a chromosomally integrated assembled or combined polynucleotide (e.g., engineered nucleic acid construct) when the integration of the assembled or combined polynucleotide results in the disruption of a gene that the host cell requires to synthesize a component essential for cell growth, thus rendering the cell auxotrophic.

Host cell transformants comprising a chromosomally integrated assembled or combined polynucleotide (e.g., engineered nucleic acid construct) can also be identified by selecting host cell transformants exhibiting other traits encoded by individual DNA segments or by combinations of DNA segments, e.g., expression of peptides that emit light, or by molecular analysis of individual host cell colonies, e.g., by restriction enzyme mapping, PCR amplification, or sequence analysis of isolated assembled polynucleotides or chromosomal integration sites.

5.11 Host Cells

Another aspect provided herein provides a host cell comprising an engineered nucleic acid construct described above. In certain embodiments, the host cell comprises the engineered nucleic acid construct integrated into the host cell genome.

Suitable host cells include any cell in which integration of the engineered nucleic acid construct into a chromosomal or episomal locus is desired. In some embodiments, the host cell is a prokaryotic cell. In some embodiments, the host cell is a bacterial cell. In some embodiments, the host cell is an *Escherichia coli* cell. In some embodiments, the host cell is a eukaryotic cell. In some embodiments, the host cell is a mammalian cell. In some embodiments, the host cell is a Chinese hamster ovary (CHO) cell, a COS-7 cell, a mouse fibroblast cell, a mouse embryonal carcinoma cell, or a mouse embryonic stem cell. In some embodiments, the host cell is an insect cell. In some embodiments, the host cell is a S2 cell, a Schneider cell, a S12 cell, a 5B1-4 cell, a Tn5 cell, or a Sf9 cell. In some embodiments, the host cell is a unicellular eukaryotic organism cell.

In some embodiments, the host cell is a yeast cell. In some embodiments, the host cell is a diploid yeast cell. In some embodiments, the host cell is a haploid yeast cell. Useful yeast host cells include yeast cells that have been deposited with microorganism depositories (e.g. IFO, ATCC, etc.) and belong to the genera *Aciculoconidium, Ambrosiozyma, Arthroascus, Arxiozyma, Ashbya, Babjevia, Bensingtonia, Botryoascus, Botryozyma, Brettanomyces, Bullera, Bulleromyces, Candida, Citeromyces, Clavispora, Cryptococcus, Cystofilobasidium, Debaryomyces, Dekkara, Dipodascopsis, Dipodascus, Eeniella, Endomycopsella, Eremascus, Eremothecium, Erythrobasidium, Fellomyces, Filobasidium, Galactomyces, Geotrichum, Guilliermondella, Hanseniaspora, Hansenula, Hasegawaea, Holtermannia, Hormoascus, Hyphopichia, Issatchenkia, Kloeckera, Kloeckeraspora, Kluyveromyces, Kondoa, Kuraishia, Kurtzmanomyces, Leucosporidium, Lipomyces, Lodderomyces, Malassezia, Metschnikowia, Mrakia, Myxozyma, Nadsonia, Nakazawaea, Nematospora, Ogataea, Oosporidium, Pachysolen, Phachytichospora, Phaffia, Pichia, Rhodosporidium, Rhodotorula, Saccharomyces, Saccharomycodes, Saccharomycopsis, Saitoella, Sakaguchia, Saturnospora, Schizoblastosporion, Schizosaccharomyces, Schwanniomyces, Sporidiobolus, Sporobolomyces, Sporopachydermia, Stephanoascus, Sterigmatomyces, Sterigmatosporidium, Symbiotaphrina, Sympodiomyces, Sympodiomycopsis, Torulaspora, Trichosporiella, Trichosporon, Trigonopsis, Tsuchiyaea, Udeniomyces, Waltomyces, Wickerhamia, Wickerhamiella, Williopsis, Yamadazyma, Yarrowia, Zygoascus, Zygosaccharomyces, Zygowilliopsis*, and *Zygozyma*, among others.

In some embodiments, the yeast host cell is a *Saccharomyces cerevisiae* cell, a *Pichia pastoris* cell, a *Schizosaccharomyces pombe* cell, a *Dekkera bruxellensis* cell, a *Kluyveromyces lactis* cell, an *Arxula adeninivorans* cell, or a *Hansenula polymorpha* (now known as *Pichia angusta*) cell. In a particular embodiment, the yeast host cell is a *Saccharomyces cerevisiae* cell. In some embodiments, the yeast host cell is a *Saccharomyces fragilis* cell or a *Kluyveromyces lactis* (previously called *Saccharomyces lactis*) cell. In some embodiments, the yeast host cell is a cell belonging to the genus *Candida*, such as *Candida lipolytica, Candida guilliermondii, Candida krusei, Candida pseudotropicalis*, or *Candida utilis*. In another particular embodiment, the yeast host cell is a *Kluveromyces marxianus* cell.

In particular embodiments, the yeast host cell is a *Saccharomyces cerevisiae* cell selected from the group consisting of a Baker's yeast cell, a CBS 7959 cell, a CBS 7960 cell, a CBS 7961 cell, a CBS 7962 cell, a CBS 7963 cell, a CBS 7964 cell, a IZ-1904 cell, a TA cell, a BG-1 cell, a CR-1 cell, a SA-1 cell, a M-26 cell, a Y-904 cell, a PE-2 cell, a PE-5 cell, a VR-1 cell, a BR-1 cell, a BR-2 cell, a ME-2 cell, a VR-2 cell, a MA-3 cell, a MA-4 cell, a CAT-1 cell, a CB-1 cell, a NR-1 cell, a BT-1 cell, and a AL-1 cell. In some embodiments, the host cell is a *Saccharomyces cerevisiae* cell selected from the group consisting of a PE-2 cell, a CAT-1 cell, a VR-1 cell, a BG-1 cell, a CR-1 cell, and a SA-1 cell. In a particular embodiment, the *Saccharomyces cerevisiae* host cell is a PE-2 cell. In another particular embodiment, the *Saccharomyces cerevisiae* host cell is a CAT-1 cell. In another particular embodiment, the *Saccharomyces cerevisiae* host cell is a BG-1 cell.

In certain embodiments, an engineered nucleic acid construct as described above may be introduced into a host cell using any conventional technique to introduce engineered nucleic acids into a cell known in the art. Such methods include, but are not limited to, direct uptake of the molecule by a cell from solution, or facilitated uptake through lipofection using, e.g., liposomes or immunoliposomes; particle-mediated transfection; etc. See, e.g., U.S. Pat. No. 5,272,065; Goeddel et al., eds, 1990, Methods in Enzymology, vol. 185, Academic Press, Inc., CA; Krieger, 1990, Gene Transfer and Expression—A Laboratory Manual, Stockton Press, NY; Sambrook et al., 1989, Molecular Cloning—A Laboratory Manual, Cold Spring Harbor Laboratory, NY; and Ausubel et al., eds., Current Edition, Current Protocols in Molecular Biology, Greene Publishing Associates and Wiley Interscience, NY. Particular methods for transforming yeast cells are well known in the art. See Hinnen et al., Proc. Natl. Acad. Sci. USA 75:1292-3 (1978); Cregg et al., Mol. Cell. Biol. 5:3376-3385 (1985). Exemplary techniques include but are not limited to, spheroplasting, electroporation, PEG 1000 mediated transformation, and lithium acetate or lithium chloride mediated transformation.

5.12 Entry Vectors

In another aspect, provided herein is a vector, i.e., an entry vector, that can be used to prepare an assembly vector. In some embodiments, an entry vector is a circular polynucleotide that comprises a selectable marker, an origin of replication, and a DNA segment immediately flanked by two restriction sites that facilitate the subcloning of different DNA segments to be assembled in the assembly methods provided herein. The entry vector further comprises one or two annealable linker nucleic acid sequences, or an annealable linker nucleic acid sequence and a primer binding segment, flanking the restriction sites. The entry vector further comprises an additional pair of restriction sites positioned at the outer flanks of the DNA segment, e.g., that flank the one or two annealable linker nucleic acid sequences, or the annealable linker nucleic acid sequence and primer binding segment. Thus, in some embodiments, the entry vector is a circular polynucleotide that comprises, in a 5' to 3' orientation, a restriction site RA, an annealable linker nucleic acid sequence LA, a restriction site RY, a DNA segment D, a restriction site RZ, and a restriction site RB. In other embodiments, the entry vector is a circular polynucleotide that comprises, in a 5' to 3' orientation, a restriction site RA, a restriction site RY, a DNA segment D, a restriction site RZ, an annealable linker nucleic acid sequence LB, and a restriction site RB. In other embodiments, the entry vector is a circular polynucleotide that comprises, in a 5' to 3' orientation, a restriction site RA, a primer binding segment PA or an annealable linker nucleic acid sequence LA, a restriction site RY, a DNA segment D, a restriction site RZ, a primer binding segment PB or an annealable linker nucleic acid sequence LB, and a restriction site RB.

In some embodiments, the sequence of the DNA segment D of the entry vector is the lac Z reporter gene. The lac Z reporter gene is useful for facilitating blue/white selection of colonies transformed with vectors comprising DNA segments other than lac Z, e.g., during the preparation of an assembly vector described herein.

In some embodiments, the entry vector is a circular polynucleotide that comprises, in a 5' to 3' orientation, a restriction site RA, an annealable linker nucleic acid sequence LA, a restriction site RY, a DNA segment D, a restriction site RZ, and a restriction site RB (i.e., 5'-RA-LA-RY-D-RZ-RB-3'). In some embodiments, the entry vector is a circular polynucleotide that comprises, in a 5' to 3' orientation, a restriction site RA, a restriction site RY, a DNA segment D, a restriction site RZ, an annealable linker nucleic acid sequence LB, and a restriction site RB (i.e., 5'-RA-RY-D-RZ-LB-RB-3'). In some embodiments, the entry vector is a circular polynucleotide that comprises, in a 5' to 3' orientation, a restriction site RA, an annealable linker nucleic acid sequence LA, a restriction site RY, a DNA segment D, a restriction site RZ, an annealable linker nucleic acid sequence LB, and a restriction site RB (i.e., 5'-RA-LA-RY-D-RZ-LB-RB-3'). In some embodiments, the entry vector is a circular polynucleotide that comprises, in a 5' to 3' orientation, a restriction site RA, a primer binding segment PA, a restriction site RY, a DNA segment D, a restriction site RZ, an annealable linker nucleic acid sequence LB, and a restriction site RB (i.e., 5'-RA-PA-RY-D-RZ-LB-RB-3'). In some embodiments, the entry vector is a circular polynucleotide that comprises, in a 5' to 3' orientation, a restriction site RA, an annealable linker nucleic acid sequence LA, a restriction site RY, a DNA segment D, a restriction site RZ, a primer binding segment PB, and a restriction site RB (i.e., 5'-RA-LA-RY-D-RZ-PB-RB-3'). An exemplary entry vector is provided in FIG. 1A.

The primer binding segment can be any nucleotide sequence that is not complementary with any of the annealable linker nucleic acid sequences that are used to make an assembled polynucleotide. In some embodiments, the primer binding segment includes a restriction endonuclease recognition and cleavage site. In some embodiments, the primer binding segment is simply one of the available linker nucleic acid sequences that are not being used in a particular assembly reaction.

In some embodiments, the nucleic acid sequence of annealable linker nucleic acid sequence LA or LB is at least 24 nucleotides and has a $T_m$ of at least 60° C. The restriction sites RY and RZ can be utilized as cloning sites to introduce various DNA segments for the generation of an assembly vector. In some embodiments, RY and RZ are not identical in sequence. In some embodiments, RY and RZ are cleavable by the same restriction endonuclease. In some embodiments, RY and RZ are identical in sequence. In some embodiments, restriction sites RY and RZ are cleavable by a restriction endonuclease that generates staggered ends, i.e. termini having a 5' or 3' overhang. In other embodiments, restriction sites RY and RZ are cleavable by a restriction endonuclease that generates blunt ends.

Although restriction sites RY and RZ can be any restriction site known in the art, restriction sites recognized by the Type IIS restriction endonucleases are particularly useful. Type IIS restriction endonucleases have DNA binding domains that are distinct from their cleavage domains. Therefore, they recognize a specific sequence but cleave at a defined distance away. For example, the Type IIS restriction endonuclease SchI (which is also known as MlyI) binds to a recognition site containing the sequence GAGTC and cleaves four (4) base pairs away from the recognition site, creating a blunt ended DNA molecule. Type IIS restriction sites are particularly useful for the preparation of an assembly vector from an entry vector. For example, in a subcloning procedure wherein the DNA segment of an entry vector, for example lacZ, is replaced with a DNA segment of interest, excision of lacZ with a Type IIS restriction endonuclease can result in complete removal of the restriction site recognition sequence. As a result, upon ligation of the DNA segment of interest to the linearized entry vector, extraneous sequence between the annealable linker nucleic acid sequence or the primer binding segment and the newly introduced DNA segment is minimized.

Thus, in some embodiments, restriction sites RY and RZ are restriction sites recognizable and cleavable by any Type IIS restriction endonuclease known in the art. Suitable Type IIS restriction endonucleases include but are not limited to the following endonucleases and their isoschizomers, which are indicated in parentheses: Alw26I (BsmAI), AlwI (AclWI, BinI), AsuHPI (HphI), BbvI (Bst71I), Bcefl, BstF5I (BseGI, FokI), FauI, HgaI, SapI (LguI), MboII, PleI, SapI, SchI (MlyI), SfaNI, and TspRI, AceIII, BbsI (BbvII, BpiI, BpuAI), Bce83I, BciVI, BfiI (BmrI), BpmI (GsuI), BsaI (Eco31I), BseRI, BsgI, BsmBI (Esp3I), BsmFI, BspMI, BsrDI (Bse3DI), Bsu6I (Eam1104I), EarI, Ksp632I), Eco57I, FauI, MmeI, RleAI, TaqII, and Tth111I. In particular embodiments, restriction sites RY and RZ are recognizable and cleavable by the SchI restriction endonuclease.

In some embodiments, RA and RB are not identical in sequence. In some embodiments, RA and RB are cleavable by the same restriction endonuclease. In some embodiments, RA and RB are identical in sequence. In some embodiments, restriction sites RA and RB are cleavable by a restriction endonuclease that generates staggered ends, i.e. termini having a 5' or 3' overhang. In other embodiments, restriction sites RA and RB are cleavable by a restriction endonuclease that generates blunt ends.

Although restriction sites RA and RB can be any restriction sites known in the art, restriction sites that are relatively infrequent in DNA (e.g., cDNA) of one or more organisms (i.e., an infrequent cutter) are particularly useful. In some embodiments, restriction sites RA and RB are recognizable and cleavable by a restriction endonuclease that has relatively infrequent restriction sites in human DNA. In some embodiments, restriction sites RA and RB are recognizable and cleavable by a restriction endonuclease that has relatively infrequent restriction sites in mouse DNA. In some embodiments, restriction sites RA and RB are recognizable and cleavable by a restriction endonuclease that has relatively infrequent restriction sites in yeast DNA, for example, in the DNA of *Saccharomyces cerevisiae*, *Pichia pastoris*, *Kluyveromyces lactis*, *Arxula adeninivorans*, or *Hansenula polymorpha*. In some embodiments, restriction sites RA and RB are recognizable and cleavable by a restriction endonuclease that has relatively few restriction sites in the DNA of bacteria, for example, in the DNA of *Escherichia coli* or *Bacillus subtilis*.

In some embodiments, restriction sites RA and RB are recognizable and cleavable by a Type IIS restriction endonuclease wherein the recognition site is distal to the polynucleotide sequence comprising, e.g., PA/LA-D-PB/LB. In some embodiments, each restriction site RA and RB is independently recognizable and cleavable by a restriction endonuclease selected from the group consisting of MssI, NruI (Bsp68I, MluB2I, Sbo13I, SpoI), SnaBI (BstSNI, Eco105I), SrfI, and SwaI (BstRZ246I, BstSWI, MspSWI, SmiI), HpaI, HincII, PshAI, OliI, AluI, Alw26I, BalI, DraI, DpnI, EcoR47III, EcoRCRI, EcoRV, FokI, HaeIII, HincII, MboI, MspAlI, NaeI, RsaI, PvuII, ScaI, SmaI, SspI, StuI, XmnI, EcaBC3I, SciI, HincII, DraI, BsaBI, Cac8I, Hpy8I, MlyI, PshAI, SspD51, BfrBI, BsaAI, BsrBI, BtrI, CdiI, CviJI, CviRI, Eco47III, Eco78I, EcoICRI, FnuDII, FspAI, HaeI, LpnI, MlyI, MslI, MstI, NaeI, NlaIV, NruI, NspBII, OliI, PmaCI, PshAI, PsiI, SrfI, StuI, XcaI, XmnI, ZraI, and isoschizomers thereof. In a particular embodiment, restriction sites RA and RB are recognizable and cleavable by the SapI or LguI restriction endonuclease. LguI is an isoschizomer of SapI having the same recognition and cleavage specificity.

In some embodiments, the entry vector provided herein also comprises one or more nucleic acid sequences that generally have some function in the replication, maintenance, or integrity of the vector (e.g., origins of replication) as well as one or more selectable markers. Replication origins are unique polynucleotides that comprise multiple short repeated sequences that are recognized by multimeric origin-binding proteins and that play a key role in assembling DNA replication enzymes at the origin site. Suitable origins of replication for use in the entry and assembly vectors provided herein include but are not limited to *E. coli* oriC, colE1 plasmid origin, 2μ and ARS (both useful in yeast systems), sfl, SV40 EBV oriP (useful in mammalian systems), or those found in pSC101. Selectable markers can be useful elements in vectors as they provide a means to select for or against growth of cells that have been successfully transformed with a vector containing the selectable marker and express the marker.

In some embodiments, any vector may be used to construct the entry vector as provided herein. In particular, vectors known in the art and those commercially available (and variants or derivatives thereof) may be engineered to include a restriction site RA, optionally a primer binding segment PA or an annealable linker nucleic acid sequence LA, a restriction site RY, a DNA segment D, a restriction site RZ, optionally a primer binding segment PB or an annealable linker nucleic acid sequence LB, and a restriction site RB, for use in the methods provided herein. Such vectors may be obtained from, for example, VECTOR LABORATORIES INC., INVITROGEN, PROMEGA, NOVAGEN, NEB, CLONTECH, BOEHRINGER MANNHEIM, PHARMACIA, EPICENTER, ORIGENES TECHNOLOGIES INC., STRATAGENE, PERKIN ELMER, PHARMINGEN, LIFE TECHNOLOGIES, INC., and RESEARCH GENETICS. General classes of vectors of particular interest include prokaryotic and/or eukaryotic cloning vectors, expression vectors, fusion vectors, two-hybrid or reverse two-hybrid vectors, shuttle vectors for use in different hosts, mutagenesis vectors, transcription vectors, vectors for receiving large inserts, and the like. Other vectors of interest include viral origin vectors (M13 vectors, bacterial phage λ vectors, adenovirus vectors, and retrovirus vectors), high, low and adjustable copy number vectors, vectors that have compatible replicons for use in combination in a single host (PACYC184 and pBR322) and eukaryotic episomal replication vectors (pCDM8).

5.13 Assembly Vectors

In some embodiments, an assembly vector is a circular polynucleotide that comprises a selectable marker, an origin of replication, and a DNA segment flanked by an annealable linker nucleic acid sequence, an annealable linker nucleic acid sequence pair, or by an annealable linker nucleic acid sequence/primer binding segment pair, flanked by a pair of restriction sites. The restriction sites can serve to facilitate excision of the component polynucleotide from the assembly vector backbone during the assembly reaction. Thus, in some embodiments, the assembly vector is a circular polynucleotide that comprises, in a 5' to 3' orientation, a restriction site RA, a primer binding segment PA or an annealable linker nucleic acid sequence LA, a DNA segment D, and a restriction site RB. In some embodiments, the assembly vector is a circular polynucleotide that comprises, in a 5' to 3' orientation, a restriction site RA, a DNA segment D, a primer binding segment PB or an annealable linker nucleic acid sequence LB, and a restriction site RB. In certain embodiments, the assembly vector is a circular polynucleotide that comprises, in a 5' to 3' orientation, a restriction site RA, a primer binding segment PA or an annealable linker nucleic acid sequence LA, a DNA segment D, a primer binding segment PB or an annealable linker nucleic acid sequence LB, and a restriction site RB.

In some embodiments, the assembly vector is a circular polynucleotide that comprises, in a 5' to 3' orientation, a restriction site RA, an annealable linker nucleic acid sequence LA, a DNA segment D, and a restriction site RB (i.e., 5'-RA-LA-D-RB-3'). In some embodiments, the assembly vector is a circular polynucleotide that comprises, in a 5' to 3' orientation, a restriction site RA, a DNA segment D, an annealable linker nucleic acid sequence LB, and a restriction site RB (i.e., 5'-RA-D-LB-RB-3'). In some embodiments, the assembly vector is a circular polynucleotide that comprises, in a 5' to 3' orientation, a restriction site RA, an annealable linker nucleic acid sequence LA, a DNA segment D, an annealable linker nucleic acid sequence LB, and a restriction site RB (i.e., 5'-RA-LA-D-LB-RB-3'). In some embodiments, the assembly vector is a circular polynucleotide that comprises, in a 5' to 3' orientation, a restriction site RA, a primer binding segment PA, a DNA segment D, an annealable linker nucleic acid sequence LB, and a restriction site RB (i.e., 5'-RA-PA-D-LB-RB-3'). In some embodiments, the assembly vector is a circular polynucleotide that comprises, in a 5' to 3' orientation, a restriction site RA, an annealable linker nucleic acid sequence LA, a DNA segment D, a primer binding segment PB, and a restriction site RB (i.e., 5'-RA-LA-D-PB-RB-3'). An exemplary assembly vector constructed from a starter vector is provided in FIG. 3B.

In preferable embodiments, the nucleic acid sequences of primer binding segment PA and primer binding segment PB are not identical. In some embodiments, the nucleic acid sequence of annealable linker nucleic acid sequence LA or LB is at least 24 nucleotides and has a $T_m$ of at least 60° C. In some embodiments, RA and RB are not identical in sequence. In some embodiments, RA and RB are cleavable by the same restriction endonuclease. In some embodiments, RA and RB are identical in sequence. In some embodiments, restriction sites RA and RB are cleavable by a restriction endonuclease that generates staggered ends, i.e. termini having a 5' or 3' overhang. In other embodiments, restriction sites RA and RB are cleavable by a restriction endonuclease that generates blunt ends.

Although restriction sites RA and RB can be any restriction sites known in the art, restriction sites that are relatively infrequent in DNA (e.g., cDNA) of one or more organisms (i.e., an infrequent cutter) are particularly useful. In some embodiments, restriction sites RA and RB are recognizable and cleavable by a restriction endonuclease that has relatively infrequent restriction sites in human DNA. In some embodiments, restriction sites RA and RB are recognizable and cleavable by a restriction endonuclease that has relatively infrequent restriction sites in mouse DNA. In some embodiments, restriction sites RA and RB are recognizable and cleavable by a restriction endonuclease that has relatively infrequent restriction sites in yeast DNA, for example, in the DNA of Saccharomyces cerevisiae, Pichia pastoris, Kluyveromyces lactis, Arxula adeninivorans, or Hansenula polymorpha. In some embodiments, restriction sites RA and RB are recognizable and cleavable by a restriction endonuclease that has relatively few restriction sites in the DNA of bacteria, for example, in the DNA of Escherichia coli or Bacillus subtilis.

In some embodiments, restriction sites RA and RB are recognizable and cleavable by a Type IIS restriction endonuclease. Illustrative examples of suitable Type IIS restriction endonucleases include but are not limited to: MssI, NruI (Bsp68I, MluB2I, Sbo13I, SpoI), SnaBI (BstSNI, Eco105I), SrfI, and SwaI (BstRZ246I, BstSWI, MspSWI, SmiI), HpaI, HincII, PshAI, OliI, AluI, Alw26I, BalI, DraI, DpnI, EcoR47III, EcoRCRI, EcoRV, FokI, HaeIII, HincII, MboI, MspAlI, NaeI, RsaI, PvuII, ScaI, SmaI, SspI, StuI, XmnI, EcaBC3I, SciI, HincII, DraI, BsaBI, Cac8I, Hpy8I, MlyI, PshAI, SspD5I, BfrBI, BsaAI, BsrBI, BtrI, CdiI, CviJI, CviRI, Eco47III, Eco78I, EcoICRI, FnuDII, FspAI, HaeI, LpnI, MlyI, MslI, MstI, NaeI, NlaIV, NruI, NspBII, OliI, PmaCI, PshAI, PsiI, SrfI, StuI, XcaI, XmnI, ZraI, or isoschizomers thereof. In a particular embodiment, restriction sites RA and RB are recognizable and cleavable by the SapI or LguI restriction endonuclease.

Preferably, the DNA segment of an assembly vector does not comprise a nucleic acid sequence that can be recognized and cleaved by a restriction endonuclease that can cleave any of restriction sites RA and RB within the assembly vector. This ensures that the DNA segment remains intact during the first stage of the assembly reaction, during which the component polynucleotide is excised from the assembly vector backbone. In particular embodiments, the DNA segment does not comprise a SapI/LguI site and RA and RB are cleavable by SapI or LguI. Site-directed mutagenesis (see Carter, Bi Chem. J. 237:1-7 (1986); Zoller and Smith, Methods Enzymol. 154:329-50 (1987)), cassette mutagenesis, restriction selection mutagenesis (Wells et al., Gene 34:315-323 (1985)), oligonucleotide-mediated (site-directed) mutagenesis, PCR mutagenesis, or other known techniques can be performed to modify any such sequence within the DNA segment either before or after ligation of the DNA segment to the entry vector.

In some embodiments, the assembly vector provided herein also comprises one or more nucleic acid sequences that generally have some function in the replication, maintenance, or integrity of the vector (e.g., origins of replication) as well as one or more selectable markers. Replication origins are unique polynucleotides that comprise multiple short repeated sequences that are recognized by multimeric origin-binding proteins and that play a key role in assembling DNA replication enzymes at the origin site. Suitable origins of replication for use in the entry and assembly vectors provided herein include but are not limited to E. coli oriC, colE1 plasmid origin, 2µ and ARS (both useful in yeast systems), sfl, SV40 EBV oriP (useful in mammalian systems), or those found in pSC101. Selectable markers can be useful elements in vectors as they provide a means to select for or against growth of cells that have been successfully transformed with a vector containing the selectable marker and express the marker.

In some embodiments, any vector may be used to construct the assembly vector as provided herein. In particular, vectors known in the art and those commercially available (and variants or derivatives thereof) may be engineered to include a restriction site RA, a primer binding segment PA or an annealable linker nucleic acid sequence LA, a DNA segment D, a primer binding segment PB or an annealable linker nucleic acid sequence LB, and a restriction site RB, for use in the methods provided herein. Such vectors may be obtained from, for example, VECTOR LABORATORIES Inc., INVITROGEN, PROMEGA, NOVAGEN, NEB, CLONTECH, BOEHRINGER MANNHEIM, PHARMACIA, EPICENTER, ORIGENES TECHNOLOGIES INC., STRATAGENE, PERKIN ELMER, PHARMINGEN, LIFE TECHNOLOGIES, INC., and RESEARCH GENETICS. General classes of vectors of particular interest include prokaryotic and/or eukaryotic cloning vectors, expression vectors, fusion vectors, two-hybrid or reverse two-hybrid vectors, shuttle vectors for use in different hosts, mutagenesis vectors, transcription vectors, vectors for receiving large inserts, and the like. Other vectors of interest include viral origin vectors (M13 vectors, bacterial phage λ vectors, adenovirus vectors, and retrovirus vectors), high, low and adjustable copy number vectors, vectors that have compatible replicons for use in combination in a single host (PACYC184 and pBR322) and eukaryotic episomal replication vectors (pCDM8).

An assembly vector can be prepared from an entry vector. Entry vectors are disclosed in Section 5.12 above. To prepare an assembly vector from an entry vector, the entry vector can be digested with one or more restriction endonucleases capable of cleaving RY and RZ thereby linearizing the vector such that it can accept a DNA segment. The DNA segment can be ligated into RY and RZ sites using standard cloning techniques to generate an assembly vector of the invention. For example, the DNA segment may be obtained by standard procedures known in the art from cloned DNA (e.g., a DNA "library"), by chemical synthesis, by cDNA cloning, or by the cloning of genomic DNA, or fragments thereof, purified from the desired cell, or by PCR amplification and cloning. See, for example, Sambrook et al., *Molecular Cloning, A Laboratory Manual*, 3d. ed., Cold Spring Harbor Laboratory Press, Cold Spring Harbor, N.Y. (2001); Glover, D. M. (ed.), *DNA Cloning: A Practical Approach*, 2d. ed., MRL Press, Ltd., Oxford, U.K. (1995).

An assembly vector can also be prepared from another vector that does not comprise an annealable linker nucleic acid sequence, an annealable linker nucleic acid sequence pair, or an annealable linker nucleic acid sequence/primer binding segment pair flanking the site of insertion of the DNA segment. To prepare an assembly vector from such a vector, the vector can be digested with one or more restriction endonucleases capable of cleaving the vector at a site suitable for insertion of a DNA fragment, e.g., at a multiple cloning site, thereby linearizing the vector such that it can accept a DNA fragment. The DNA fragment to be inserted can be obtained by standard procedures known in the art such as, for example, cloning, chemical synthesis, or PCR amplification. The DNA fragment comprises a DNA segment flanked by an annealable linker nucleic acid sequence, an annealable linker nucleic acid sequence pair or an annealable linker nucleic acid sequence/primer binding segment pair. Thus, in some embodiments, the DNA fragment comprises, in a 5' to 3' orientation, an annealable linker nucleic acid sequence LA or a primer binding segment PA, a DNA segment D, and an annealable linker nucleic acid sequence LB or a primer binding segment PB (i.e., 5'-LA-D-LB-3' or 5'-PA-D-LB-3' or 5'-LA-D-PB-3'). In some embodiments, the DNA fragment comprises, in a 5' to 3' orientation, a DNA segment D, and an annealable linker nucleic acid sequence LB or a primer binding segment PB (i.e., 5'-D-LB-3' or 5'-D-PB-3'). In some embodiments, the DNA fragment comprises, in a 5' to 3' orientation, an annealable linker nucleic acid sequence LA or a primer binding segment PA, and a DNA segment D, (i.e., 5'-LA-D-3' or 5'-PA-D-3'). The DNA fragment can further comprise a pair of restriction sites that flank the annealable linker nucleic acid sequence, the annealable linker nucleic acid sequence pair or the annealable linker nucleic acid sequence/primer binding segment pair and that upon cleavage by a restriction endonuclease produce termini that are compatible with termini produced by linearising the vector into which the DNA fragment is to be inserted. Alternatively, the DNA fragment can generated such that it contains such compatible termini and does not require additional digestion with a restriction endonuclease to produce the compatible termini. Upon ligation of the DNA fragment with the linearized vector to generate an assembly vector, the restriction sites used to generate the compatible termini may be preserved to serve as restriction sites RA and RB of the assembly vector. Alternatively, the ligation may remove the original restriction sites but additional restriction sites may be present in the linearised vector that can serve as restriction sites RA and RB of the assembly vector.

Exemplary methods for generating an assembly vector from an entry vector (i.e., a pRYSE vector) or from another vector (i.e., a pMULE vector) are provided in U.S. patent application Ser. No. 12/622,401 (Pub. No. 2010/0136633 A1), filed Nov. 19, 2009, which is hereby incorporated by reference in its entirety 5.14 Annealable Linker Nucleic Acid Sequences In another aspect, provided herein are annealable linker nucleic acid sequences that flank the DNA segment located within entry vectors and assembly vectors. Annealable linker nucleic acid sequences provide sequence overlap between adjacent component polynucleotides in an assembly reaction, and thus serve to prime a component polynucleotide for assembly into an assembled polynucleotide. Thus, in preferred embodiments, the annealable linker nucleic acid sequences LA and LB of the entry and assembly vectors are optimized to provide efficient and accurate priming to complementary annealable linker nucleic acid sequences during an assembly reaction.

In some embodiments, the length of an annealable linker nucleic acid sequence is long enough to provide adequate specificity with its complement annealable linker nucleic acid sequence, yet short enough to readily anneal to its complement annealable linker nucleic acid sequence at the annealing temperature of the assembly reaction. In some embodiments the length of an annealable linker nucleic acid sequence is long enough to allow for host cell mediated homologous recombination with its complement annealable linker nucleic acid sequence.

In some embodiments, the annealable linker nucleic acid sequence is about 5, 10, 15, 20, 25, 30, 35, 40, 45, 50, 55, 60, 65, 70, 75, or 80 nucleotides in length. In some embodiments, the annealable linker nucleic acid sequence is at least 10, 12, 14, 16, 18, 20, 22, 24, 26, 28, or 30 nucleotides in length. In some embodiments, the anealable linker nucleic acid sequence is greater than 30, 40, 50, 60, 70, 80, 90, 100, 500, 1000, 5000, or 10,000 nucleotides in length. In some embodiments, the annealable linker is at least 18 nucleotides in length and is a number divisible by three, so as to facilitate read-through transcription of the linker when ligated to an encoding DNA segment. In particular embodiments, the annealable linker is 18, 21, 24, 27, 30, 33, 36, 39, 42, 45, 48, 51, 54, 57, or 60 nucleotides in length.

In some embodiments, an annealable linker nucleic acid sequence has a relatively high melting temperature ($T_m$), i.e., the temperature at which one half of an annealed annealable linker nucleic acid sequence duplex will dissociate to become single stranded. The $T_m$ of an annealable linker can be calculated according to SantaLucia, PNAS, 95:-1460-1465 (1998) using a nearest neighbor algorithm. A relatively high $T_m$ may provide for more specific priming during an assembly reaction. A relatively high $T_m$ may also allow combination of the annealing and extension steps of PCR or reduce the amount of time needed to adjust temperatures between the annealing and extension steps of PCR and thus enable greater efficiency in using the assembly methods of the invention. Thus, in some embodiments, an annealable linker nucleic acid sequence duplex has a $T_m$ of about 60° C.-80° C. In some embodiments, an annealable linker nucleic acid sequence duplex has a $T_m$ of about 65° C.-75° C. In some embodiments, an annealable linker nucleic acid sequence duplex has a $T_m$ of greater than 50° C., 55° C., 60° C., 65° C., 70° C., 75° C., 80° C., 85° C., or 90° C.

In some embodiments, annealable linker nucleic acid sequences do not form appreciable secondary structures (e.g., hairpins, self-dimers) produced via intramolecular (i.e., within the same molecule) interactions under the conditions of the methods described herein, either at the DNA level or at the RNA level or at both the DNA and the RNA level. The presence of secondary structures in DNA can lead to poor or no assembled polynucleotide yield of the assembly reaction. The presence of secondary structures in RNA can lead to decreased translation efficiencies, which are of particular concern when the annealable linker nucleic acid sequence is used to assemble component polynucleotides comprising a promoter and a protein coding sequence inco a assembled polynucleotide in which the annealable linker nucleic acid sequence is positioned between the promoter and the protein coding sequence. Accordingly, annealable linker nucleic acid sequences useful in the assembly methods of the present disclosure are designed to not form secondary RNA and/or DNA structures. The ability of an annealable linker nucleic acid sequence to form secondary RNA or DNA structures can be determined using software tools such as, for example, IDT Oligo Analyzer (Integrated DNA Technologies, Coralville, Iowa), mFold (Zuker 2003 *Nucleic Acids Res.* 31 (13), 3406-15), or RNAfold (Hofacker & Stadler (2006) *Bioinformatics* 22 (10): 1172-6). In general, these tools calculate the Gibbs free energy ($\Delta G$) for transition of a sequence from the linear to the folded state. The larger $\Delta G$, the less likely that the sequence will form a secondary structure. Accordingly, in some embodiments, annealable linker nucleic acid sequences are designed to have large $\Delta G$ values for the transition from linear to folded states. In some embodiments, annealable linker nucleic acid sequences are designed to have $\Delta G$ values for the transition from linear to folded states that are equal to or greater than the $\Delta G$ values for the transition from linear to folded states of the n-bases that lie immediately upstream of the coding sequences of highly expressed genes in the *Saccharomyces cerevisiae* genome, where n represents an integer that corresponds to the number of bases in the annealable linker nucleic acid sequence. In some embodiments, annealable linker nucleic acid sequences are 36 bases long and have a $\Delta G$ value for the transition from linear to folded states of −1 or greater.

In some embodiments, annealable linker nucleic acid sequences are also designed to avoid unintended intermolecular interactions (e.g., between different molecules). Thus, in some embodiments, an annealable linker nucleic acid sequence does not anneal substantially with any other sequences within the assembly vector that contains the annealable linker nucleic acid sequence (e.g., vector backbone sequences) and/or with any other sequences within other assembly vectors of the assembly compositions aside from the complementary annealable linker nucleic acid sequences required for polynucleotide assembly by the methods provided herein. In some embodiments, an annealable linker nucleic acid sequence does not anneal substantially with other annealable linker nucleic acid sequences within assembly vectors of the assembly compositions provided herein.

In some embodiments, an annealable linker nucleic acid sequence has a high G-C content, i.e., the number of guanine and cytosine nucleotides in the annealable linker nucleic acid sequence as a percentage of the total number of bases in the annealable linker nucleic acid sequence. Annealable linker nucleic acid sequences that have a high G-C content are generally useful in the methods of the invention because a high G-C content generally provides for a high $T_m$, which in turn may provide for more specific priming during an assembly reaction and for time and process savings by allowing combination of the annealing and extension steps of SOE/PCR. In some embodiments, the G-C content of the annealable linker nucleic acid sequence is between about 20-80%. In some embodiments, the G-C content of the annealable linker nucleic acid sequence is between about 40-60%. In some embodiments, the G-C content of the annealable linker nucleic acid sequence is about 40, 45, 50, 55, 60, or 70%. In particular embodiments, an annealable linker nucleic acid sequence has a G-C content of greater than 70%. Illustrative examples of annealable linker nucleic acid sequences that have a high G-C content, do not form appreciable secondary DNA structures, and have a $T_m$ of 70° C. or greater are generally disclosed in U.S. patent application Ser. No. 12/622,401 (Pub. No. 2010/0136633 A1), filed Nov. 19, 2009, which is hereby incorporated by reference in its entirety, including SEQ ID NOS: 1 to 8 filed therein.

In some embodiments, an annealable linker nucleic acid sequence has a high A-T content, i.e., the number of adenine and thymine nucleotides in the annealable linker nucleic acid sequence as a percentage of the total number of bases in the annealable linker nucleic acid sequence. A high A-T content may provide for reduced propensity of the annealable linker nucleic acid sequence to form substantial secondary structures, which may be of particular concern when the annealable linker nucleic acid sequence is used to assemble component polynucleotides comprising a promoter and a protein coding sequence into a assembled polynucleotide in which the annealable linker nucleic acid sequence is positioned between the promoter and the protein coding sequence. In some embodiments, the A-T content of the annealable linker nucleic acid sequence is between about 20-80%. In some embodiments, the A-T content of the annealable linker nucleic acid sequence is between about 40-60%. In some embodiments, the A-T content of the annealable linker nucleic acid sequence is about 30, 35, 40, 45, 50, 55, or 60%. In some embodiments, the annealable linker nucleic acid sequence has an A-T content of greater than 30%. Illustrative examples of annealable linker nucleic acid sequences that comprise a preferred consensus motif, have a relatively high A-T content, do not form appreciable secondary RNA or DNA structures, and have a $T_m$ of 65° C. or greater are generally disclosed in U.S. patent application Ser. No. 12/622,401 (Pub. No. 2010/0136633 A1), filed Nov. 19, 2009, which is hereby incorporated by reference in its entirety, including SEQ ID NOS: 9 to 23 filed therein.

In some embodiments, an annealable linker nucleic acid sequence comprises one or more restriction sites. Incorporation of restriction sites into an annealable linker nucleic acid sequence allows for the excision of a DNA segment from an entry or assembly vector while maintaining the restriction sites RA and RB within the entry vector or assembly vector. Restriction sites within the annealable linker nucleic acid sequence also facilitate directional subcloning of DNA segments into other entry or assembly vectors. This feature facilitates the efficient construction of assembly vectors comprising the same DNA segment but having different annealable linker nucleic acid sequence pairs or primer binding segment/annealable linker nucleic acid sequence pairs, for instance, to generate a library of assembly vectors comprising different annealable linker nucleic acid sequence pairs as described below. This feature can also obviate the need to re-amplify and sequence a DNA segment to create additional assembly vectors comprising the DNA segment. Thus, in some embodiments, the annealable linker nucleic acid sequence comprises a unique restriction site. In some embodiments, the restriction site is a 7-base pair restriction site, i.e., is cleavable by a restriction endonuclease that recognizes a 7-base pair nucleotide sequence. In some embodiments, the restriction site is a 8-base pair restriction site. In particular embodiments, the restriction site within the annealable linker nucleic acid sequence is recognized and cleavable by MreI, FseI, SbfI, AsiSI, NotI, AscI, or BbvCI.

In some embodiments, the annealable linker nucleic acid sequence comprises a sequence that allows for read-through transcription once the linker is ligated to an encoding DNA segment. In some embodiments, an annealable linker nucleic acid sequence allows for read-through transcription in both the 5' to 3' and 3' to 5' orientation. In these embodiments, the length of the annealable linker nucleic acid sequence, preferably, is a number of nucleotides divisible by three (3).

In particular embodiments, an annealable linker nucleic acid sequence does not comprise codons that are rarely used in *Escherichia coli* (*E. coli*) or *Saccharomyces cerevisiae* (*S. cerevisiae*). Efficient expression of heterologous genes in *E. coli* or *S. cerevisiae* can be adversely affected by the presence of infrequently used codons, and expression levels of the heterologous protein often rise when rare codons are replaced by more common ones. See, e.g., Williams et al., *Nucleic Acids Res.* 16: 10453-10467, 1988 and Hoog et al., *Gene* 43: 13-21, 1986. Accordingly, an annealable linker nucleic acid sequence that comprises a read-through sequence preferably does not comprise rare codons used in *E. coli* or *S. cerevisiae*, so as to enable efficient expression of proteins encoded by a assembled polynucleotide comprising the annealable linker nucleic acid sequence.

In some embodiments, the set of annealable linker nucleic acid sequences are unique sequences that are not found in an intended host organism. In some embodiments, the set of annealable linker nucleic acid sequences are unique sequences that are not found in *E. coli*. In other embodiments, the set of annealable linker nucleic acid sequences are unique sequences that are not found in *S. cerevisiase*.

In some embodiments, suitable annealable linker nucleic acid sequences are identified in a test assembled polynucleotide. A test assembled polynucleotide comprises the annealable linker nucleic acid sequence to be tested and additional elements that permit testing of the annealable linker nucleic acid sequence. For example, to test whether an annealable linker is suitable for assembling a first component polynucleotide comprising a promoter sequence and a second component polynucleotide comprising a protein coding sequence to be put under the control of the promoter in the assembled polynucleotide, a test assembled polynucleotide can be assembled from the first component polynucleotide comprising, in a 5' to 3' orientation, a primer binding segment or an annealable linker nucleic acid sequence, a DNA segment comprising the promoter, and the annealable linker nucleic acid sequence to be tested, and the second component polynucleotide comprising, in a 5' to 3' orientation, the annealable linker nucleic acid sequence to be tested, a DNA segment encoding a reporter gene (e.g., green fluourescent protein (GFP)), and a primer binding segment or annealable linker nucleic acid sequence. The test assembled polynucleotide can be tested in vivo or in vitro for the efficiency of expression of the reporter gene. Similar test assembled polynucleotides can be assembled to test the suitability of annealable linker nucleic acid sequences for assembling component polynucleotides comprising DNA segments comprising other elements, such as an enhancer, terminator, poly-A tail, nuclear localization signal, mRNA stabilization signal, selectable marker, epitope tag coding sequence, degradation signal, and the like. The test assembled polynucleotide may comprise additional component polynucleotides that enable testing, such as for example, genomic targeting sequences and selectable markers that enable introduction of the test assembled polynucleotide into host cells and selection of positive transformants for in vivo testing.

6. INCORPORATION BY REFERENCE

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications can be made thereto without departing from the spirit or scope of the appended claims. The embodiments of the present invention described above are intended to be merely exemplary, and those skilled in the art will recognize, or be able to ascertain using no more than routine experimentation, numerous equivalents to the specific procedures described herein. All such equivalents are considered to be within the scope of the present invention and are covered by the following claims. Furthermore, as used in this specification and claims, the singular forms "a," "an" and "the" include plural forms unless the content clearly dictates otherwise.

What is claimed is:

1. A method of defining an engineered nucleic acid construct for integration into a genomic locus L of a target organism or a host cell, the method comprising:

(A) receiving a plurality of nucleic acid requests $\{NR_1, \ldots, NR_n\}$, wherein n is a positive integer greater than 1, each nucleic acid request $NR_i$ in $\{NR_1, \ldots, NR_n\}$ specifying a genetic change to L;

(B) expanding each $NR_i$ in $\{NR_1, \ldots, NR_n\}$ into a corresponding component polynucleotide, thereby forming a plurality of component polynucleotides;

(C) arranging the plurality of component polynucleotides into a contiguous arrangement $AR_i$, wherein the arranging uses linker nucleic acid sequences from a predetermined library of linker nucleic acid sequences to combine component polynucleotides in the plurality of component polynucleotides into the contiguous arrangement $AR_i$;

(D) repeating the arranging (C) until a set of $\{AR_1, \ldots, AR_m\}$ contiguous arrangements are formed, wherein m is a positive integer greater than 1, the set of $\{AR_1, \ldots, AR_m\}$ contiguous arrangements representing a plurality of different contiguous arrangements of the component polynucleotides in the plurality of component polynucleotides;

(E) determining a score $S_i$ for each respective contiguous arrangement $AR_i$ in $\{AR_1, \ldots, AR_m\}$, wherein, for each respective contiguous arrangement $AR_i$, a contribution to the score $S_i$ is made when one or more source constructs are identified as being physically present in a freezer store, wherein each of the one or more physically present source constructs encodes one or more of the component polynucleotides, and wherein a 3' or 5' terminus, or both the 3' and 5' termini, of each respective component polynucleotide in the one or more component polynucleotides encoded by the one or more physically present source constructs is bound to a corresponding linker nucleic acid sequence that was used for the corresponding component polynucleotide in the arranging (C) to form the $AR_i$;

(F) selecting a final contiguous arrangement $AR_f$ in $\{AR_1, \ldots, AR_m\}$ having a score $S_i$ that meets a selection criterion as an optimal contiguous arrangement; and (G) calculating, in response to selection of the $AR_f$, one or more primer pairs based upon the $AR_f$, wherein each primer pair in the one or more primer pairs is capable of amplifying a portion of the $AR_f$ not represented in any identified one or more physically present source constructs identified for the $AR_f$, wherein the portions of the contiguous arrangement $AR_f$ amplified by the one or more primer pairs and the one or more component polynucleotides in any identified one or more physically present source constructs identified for the $AR_f$, in the order specified in the $AR_f$, collectively define the engineered nucleic acid construct, wherein at least one of the receiving (A), expanding (B), arranging (C), repeating (D), determining (E), selecting (F), and calculating (G) is performed using one or more suitably programmed computers.

2. The method of claim 1, wherein the arranging (C) comprises inserting a selectable marker having a nucleic acid sequence into the contiguous arrangement $AR_i$, and the set of contiguous arrangements $\{AR_1, \ldots, AR_m\}$ represents a plurality of different contiguous arrangements of the component polynucleotides in the plurality of component polynucleotides and the selectable marker with respect to each other.

3. The method of claim 1, wherein the score $S_i$ for each respective $AR_i$ is a function of a number of component polynucleotides already arranged according to the contiguous arrangement specified by $AR_i$ in the one or more physically present constructs selected by $AR_i$ by the determining (E).

4. The method of claim 1, wherein a nucleic acid request in the plurality of nucleic acid requests specifies insertion of an insertion sequence at L.

5. The method of claim 4, wherein the insertion sequence comprises a promoter and a gene to be expressed by the promoter.

6. The method of claim 4, wherein the insertion sequence comprises a divergent promoter and a first gene and a second gene driven by the divergent promoter.

7. The method of claim 4, wherein the insertion sequence comprises a promoter, a gene, a terminator, an open reading frame, a codon substitution, a nucleic acid substitution, a point mutation, an insertion mutation, or a deletion mutation.

8. The method of claim 4, wherein the insertion sequence comprises a fusable open reading frame without a stop codon.

9. The method of claim 4, wherein the nucleic acid request specifies that the entire genomic locus L is to be replaced by the insertion sequence.

10. The method of claim 4, wherein the nucleic acid request specifies that a promoter and a gene at L is to be replaced by the insertion sequence.

11. The method of claim 4, wherein the nucleic acid request specifies that a divergent promoter and a first gene and a second gene driven by the divergent promoter at L is to be replaced by the insertion sequence.

12. The method of claim 11, wherein the divergent promoter is a back-to-back divergent promoter, an overlapping divergent promoter, or a face-to-face divergent promoter.

13. The method of claim 4, wherein the nucleic acid request specifies that a promoter, a gene, a terminator, an open reading frame, a codon substitution, a nucleic acid substitution, a point mutation, an insertion mutation, or a deletion mutation at L is to be replaced by the insertion sequence.

14. The method of claim 4, wherein the nucleic acid request specifies that a fusible open reading frame without a stop codon is to be replaced by the insertion sequence.

15. The method of claim 4, wherein the insertion sequence includes a first copy of a gene in a 3' to 5' orientation and a second copy of the gene in a 5' to 3' orientation, and a bi-directional promoter between the first copy and the second copy.

16. The method of claim 1, wherein the arranging (C) comprises barring an $AR_i$ that would cause a repeat sequence of greater than a predetermined number of bases to arise in the engineered nucleic acid construct.

17. The method of claim 1, wherein the calculating (G) comprises applying at least one design rule to identify primers in the one or more primer pairs.

18. The method of claim 17, wherein the at least one design rule is (i) avoidance of hair pin termini, (ii) avoidance of self-dimerization, (iii) primer length between 17 and 28 bases, (iv) percent G+C content between fifty and sixty percent, (v) melting temperature between 55° C. and 80° C., or (vi) avoidance of runs of three or more Cs or Gs at the 3' terminus.

19. The method of claim 1, wherein a first component polynucleotide is identical to a second component polynucleotide in the plurality of component polynucleotides and wherein the arranging (C) comprises barring a contiguous arrangement that would cause the first component polynucleotide and the second component polynucleotide to run in the same direction in the engineered nucleic acid construct.

20. The method of claim 2, wherein an identity of the selectable marker is received with the plurality of nucleic acid requests in the receiving (A).

21. The method of claim 2, wherein an identity of the selectable marker is determined without human intervention from a predetermined list of selectable markers by the arranging (C).

22. The method of claim 1, wherein the calculating (G) comprises encoding a linker nucleic acid sequence specified for contiguous arrangement $AR_f$ by the arranging (C) into a primer in the one or more primer pairs calculated for $AR_f$.

23. The method of claim 1, wherein the expanding (B) comprises expanding a first nucleic acid request in $\{NR_1, \ldots, NR_n\}$ into a first component polynucleotide and a second component polynucleotide, wherein the first component polynucleotide is a promoter and the second component polynucleotide is a gene.

24. The method of claim 1, wherein the determining (E) comprises determining whether a source construct having all or a subset of the plurality of component polynucleotides, in the contiguous order specified by the contiguous arrangement $AR_i$, is present in the freezer store, and a contribution the source construct makes to the score $S_i$ for the contiguous arrangement $AR_i$ is dependent upon a number of component polynucleotides in the source construct that are in the contiguous order specified by the contiguous arrangement $AR_i$.

25. The method of claim 1, wherein each source construct in the freezer store comprises a linker nucleic acid sequence, selected from the predetermined library of linker nucleic acid sequences, bound to a 3' end or a 5' end of a component polynucleotide.

26. The method of claim 1, wherein
the determining (E) comprises identifying a first source construct in the freezer store, the first source construct having a first subset of the plurality of component polynucleotides, in the contiguous order specified by the contiguous arrangement $AR_i$,
the determining (E) comprises identifying a second source construct in the freezer store, the second source construct having a second subset of the plurality of component polynucleotides, in the contiguous order specified by the contiguous arrangement $AR_i$,
there is no overlap between the first subset and the second subset,
a first contribution to the score $S_i$ for the contiguous arrangement $AR_i$ is based upon a number of component polynucleotides in the first source construct that are in the contiguous order specified by the contiguous arrangement $AR_i$, and
a second contribution to the score $S_i$ for the contiguous arrangement $AR_i$ is based upon a number of component polynucleotides in the second source construct that are in the contiguous order specified by the contiguous arrangement $AR_i$.

27. The method of claim 1, wherein:
the determining (E) comprises identifying a set of $\{C_1, \ldots, C_q\}$ source constructs in the freezer store, wherein q is a positive integer greater than 1, for a contiguous arrangement $Ar_i$ in the set of contiguous arrangements $\{AR_1, \ldots, AR_m\}$, each respective source construct $C_i$ in $\{C_1, \ldots, C_q\}$ having a corresponding subset $S_i$ of component polynucleotides in the plurality of component polynucleotides, in the contiguous order specified by the contiguous arrangement $Ar_i$, wherein the corresponding subset $S_i$ of component polynucleotides is not found in any other source construct in $\{C_1, \ldots, C_q\}$, and
a contribution to the score $S_i$ for $AR_i$ from each respective $C_i$ in $\{C_1, \ldots, C_q\}$ is based upon a number of component polynucleotides in $C_i$ that are in a contiguous order specified by $AR_i$.

28. An apparatus comprising one or more memories and one or more processors, wherein the one or more memories and the one or more processors are in electronic communication with each other, the one or more memories tangibly encoding a set of instructions for defining an engineered nucleic acid construct for integration into a genomic locus L of a target organism or a host cell using the one or more processors, the set of instructions comprising:
(A) instructions for receiving a plurality of nucleic acid requests $\{NR_1, \ldots, NR_n\}$, wherein n is a positive integer greater than 1, each nucleic acid request $NR_i$ in $\{NR_1, \ldots, NR_n\}$ specifying a genetic change to L;
(B) instructions for expanding each $NR_i$ in $\{NR_1, \ldots, NR_n\}$ into a corresponding component polynucleotide, thereby forming a plurality of component polynucleotides;
(C) instructions for arranging the plurality of component polynucleotides into a contiguous arrangement $AR_i$, wherein the arranging (C) uses linker nucleic acid sequences from a predetermined library of linker nucleic acid sequences to combine component polynucleotides in the plurality of component polynucleotides into a contiguous arrangement $AR_i$;
(D) instructions for repeating the instructions for arranging (C) until a set of $\{AR_1, \ldots, AR_m\}$ contiguous arrangements are formed, wherein m is a positive integer greater than 1, the set of $\{AR_1, \ldots, AR_m\}$ contiguous arrangements representing a plurality of different contiguous arrangements of the component polynucleotides in the plurality of component polynucleotides;
(E) instructions for determining a score $S_i$ for each respective contiguous arrangement $AR_i$ in $\{AR_1, \ldots, AR_m\}$, wherein, for each respective contiguous arrangement $AR_i$, a contribution to the score $S_i$ is made when one or more source constructs are identified as being physically present in a freezer store, wherein each of the one or more physically present source constructs encodes one or more of the component polynucleotides, and wherein a 3' or 5' terminus, or both the 3' and 5' termini, of each respective component polynucleotide in the one or more component polynucleotides encoded by the one or more physically present source constructs is bound to a corresponding linker that was used for the corresponding component polynucleotide in the arranging (C) to form $AR_i$;
(F) instructions for selecting a final contiguous arrangement $AR_f$ in $\{AR_1, \ldots, AR_m\}$ having a score $S_i$ that meets a selection criterion as an optimal contiguous arrangement; and
(G) instructions for calculating, in response to completion of the instructions for selecting, one or more primer pairs based upon the final $AR_f$, wherein each primer pair in the one or more primer pairs is capable of amplifying a portion of the $AR_f$ not represented in any identified one or more physically present source constructs identified for the $AR_f$, wherein the portions of the contiguous arrangement amplified by the one or more primer pairs and the one or more component polynucleotides in any identified one or more physically present source constructs identified for $AR_f$, in the order specified in the contiguous arrangement $AR_f$, collectively define the engineered nucleic acid construct.

29. A method of defining an engineered nucleic acid construct for integration into a genomic locus L of a target organism or a host cell, the method comprising:
(A) receiving a plurality of nucleic acid requests $\{NR_1, \ldots, NR_n\}$, wherein n is a positive integer greater than 1, each nucleic acid request $NR_i$ in $\{NR_1, \ldots, NR_n\}$ specifying a genetic change to L;
(B) expanding each $NR_i$ in $\{NR_1, \ldots, NR_n\}$ into a corresponding component polynucleotide, thereby forming a plurality of component polynucleotides;
(C) arranging the plurality of component polynucleotides into a contiguous arrangement $AR_i$, wherein the arranging (C) uses linker nucleic acid sequences from a predetermined library of linker nucleic acid sequences to combine component polynucleotides in the plurality of component polynucleotides into the $AR_i$;
(D) selecting, in response to the arranging, one or more source constructs from a plurality of source constructs physically present in a freezer store, wherein each of the one or more physically present source constructs encode one or more of the component polynucleotides, and wherein a 3' or 5' terminus, or both the 3' and 5' termini, of each respective component polynucleotide in the one or more component polynucleotides encoded by the one or more physically present source constructs is bound to a corresponding linker that was used for the corresponding component polynucleotide in the arranging (C) to form the $AR_i$; and
(E) calculating one or more primer pairs based upon $AR_i$, wherein each primer pair is capable of amplifying a portion of $AR_i$ not represented in the one or more physically present source constructs identified for $AR_i$, wherein the portions of the $AR_i$ amplified by the one or more primer pairs and the one or more component polynucleotides in the one or more physically present source constructs identified for the $AR_i$, in the order specified by the $AR_i$, collectively define the engineered nucleic acid construct, wherein at least one of the expanding (B), arranging (C), selecting (D), and calculating (E) is performed using one or more suitably programmed computers.

30. A non-transitory computer readable storage medium storing one or more programs configured for execution by one or more processors of a system, the one or more programs for defining an engineered nucleic acid construct for integration into a genomic locus L of a target organism or a host cell, the one or more programs comprising:

(A) instructions for receiving a plurality of nucleic acid requests $\{NR_1, \ldots, NR_n\}$, wherein n is a positive integer greater than 1, each nucleic acid request $NR_i$ in $\{NR_1, \ldots, NR_n\}$ specifying a genetic change to L;

(B) instructions for expanding each $NR_i$ in $\{NR_1, \ldots, NR_n\}$ into a corresponding component polynucleotide, thereby forming a plurality of component polynucleotides;

(C) instructions for arranging the plurality of component polynucleotides into a contiguous arrangement $AR_i$, wherein the arranging (C) uses linker nucleic acid sequences from a predetermined library of linker nucleic acid sequences to combine component polynucleotides in the plurality of component polynucleotides into a contiguous arrangement $AR_i$;

(D) instructions for repeating the instructions for arranging (C) until a set of $\{AR_1, \ldots, AR_m\}$ contiguous arrangements are formed, wherein m is a positive integer greater than 1, the set of $\{AR1, \ldots, ARm\}$ contiguous arrangements representing a plurality of different contiguous arrangements of the component polynucleotides in the plurality of component polynucleotides;

(E) instructions for determining a score $S_i$ for each respective contiguous arrangement $AR_i$ in $\{AR_1, \ldots, AR_m\}$, wherein, for each respective contiguous arrangement $AR_i$, a contribution to the score $S_i$ is made when one or more source constructs are identified as being physically present in a freezer store, wherein each of the one or more physically present source constructs encodes one or more of the component polynucleotides, and wherein a 3' or 5' terminus, or both the 3' and 5' termini, of each respective component polynucleotide in the one or more component polynucleotides encoded by the one or more physically present source constructs is bound to a corresponding linker that was used for the corresponding component polynucleotide in the arranging (C) to form $AR_i$;

(F) instructions for selecting a final contiguous arrangement $AR_f$ in $\{AR_1, \ldots, AR_m\}$ having a score $S_i$ that meets a selection criterion as an optimal contiguous arrangement; and (G) instructions for calculating, in response to completion of the instructions for selecting, one or more primer pairs based upon the final $AR_f$, wherein each primer pair in the one or more primer pairs is capable of amplifying a portion of the $AR_f$ not represented in any identified one or more physically present source constructs identified for the $AR_f$, wherein the portions of the contiguous arrangement amplified by the one or more primer pairs and the one or more component polynucleotides in any identified one or more physically present source constructs identified for $AR_f$, in the order specified in the contiguous arrangement $AR_f$, collectively define the engineered nucleic acid construct.

* * * * *

SEQUENCE LISTING

<160> NUMBER OF SEQ ID NOS: 3

<210> SEQ ID NO 1
<211> LENGTH: 102
<212> TYPE: PRT
<213> ORGANISM: Saccharomyces cerevisiae

<400> SEQUENCE: 1

-continued

```
Met Pro Pro Lys Lys Phe Lys Asp Leu Asn Ser Phe Leu Asp Asp Gln
1               5                   10                  15

Pro Lys Asp Pro Asn Ile Val Ala Ser Pro Phe Gly Gly Tyr Phe Phe
                20                  25                  30

Lys Asn Pro Ala Ala Asp Ala Gly Ser Asn Asn Ala Ser Lys Lys Ser
            35                  40                  45

Ser Tyr Gln Gln Gln Arg Asn Trp Lys Gln Gln Gly Gly Asn Tyr Gln
    50                  55                  60

Gln Gly Gly Tyr Gln Ser Tyr Asn Ser Asn Tyr Asn Asn Tyr Asn Asn
65              70                  75                  80

Tyr Asn Asn Tyr Asn Asn Tyr Asn Asn Tyr Asn Asn Tyr Asn Lys Phe
                85                  90                  95

His Gly Gln Gly Tyr Gln
            100
```

<210> SEQ ID NO 2
<211> LENGTH: 300
<212> TYPE: DNA
<213> ORGANISM: Homo sapiens

<400> SEQUENCE: 2

```
atgcctccaa agaagtttaa ggatctaaac tcttccttga cgaccaacca aaggacccaa      60
atctagtcgc ttctcccttc cggtggttat tttaaaaacc ctgctgctga tgccggtagt     120
aataacgctt ccaaaaaaag tagctaccaa caacagcgta attggaaaca ggggggcaac     180
taccaacaag gtggttacca atcgtataac agtaattaca acaattacaa caactacaac     240
aactacaaca attataacaa ctacaataac tataataaat acaatggcca gggctatcaa     300
```

<210> SEQ ID NO 3
<211> LENGTH: 300
<212> TYPE: DNA
<213> ORGANISM: Homo sapiens

<400> SEQUENCE: 3

```
atgcctccaa agaagtttaa ggatctaaac tctttccttg acgaccaacc aaaggaccca      60
aatctagtcg cttctccctt cggtggttat tttaaaaacc ctgctgctga tgccggtagt     120
aataacgctt ccaaaaaaag tagctaccaa caacagcgta attggaaaca ggggggcaac     180
taccaacaag gtggttacca atcgtataac agtaattaca acaattacaa caactacaac     240
aactacaaca attataacaa ctacaataac tataataaat acaatggcca gggctatcaa     300
```